United States Patent
Georgopoulos et al.

(10) Patent No.: US 10,940,182 B2
(45) Date of Patent: *Mar. 9, 2021

(54) USE OF MODIFIED VASOACTIVE INTESTINAL PEPTIDES IN THE TREATMENT OF HYPERTENSION

(71) Applicant: PhaseBio Pharmaceuticals, Inc., Malvern, PA (US)

(72) Inventors: Lynne M. Georgopoulos, Malvern, PA (US); Susan Arnold, Malvern, PA (US)

(73) Assignee: PHASEBIO PHARMACEUTICALS, INC., Malvern, PA (US)

( * ) Notice: Subject to any disclaimer, the term of this patent is extended or adjusted under 35 U.S.C. 154(b) by 164 days.

This patent is subject to a terminal disclaimer.

(21) Appl. No.: 15/276,151

(22) Filed: Sep. 26, 2016

(65) Prior Publication Data

US 2017/0072021 A1   Mar. 16, 2017

Related U.S. Application Data

(63) Continuation of application No. 14/124,612, filed as application No. PCT/US2012/041092 on Jun. 6, 2012, now Pat. No. 9,561,262.

(60) Provisional application No. 61/493,845, filed on Jun. 6, 2011.

(51) Int. Cl.
| | |
|---|---|
| A61K 38/22 | (2006.01) |
| C07K 14/575 | (2006.01) |
| C07K 14/78 | (2006.01) |
| A61K 45/06 | (2006.01) |
| A61K 31/403 | (2006.01) |
| A61K 31/165 | (2006.01) |
| A61K 31/4045 | (2006.01) |
| A61K 31/4418 | (2006.01) |
| A61K 38/39 | (2006.01) |
| A61K 38/00 | (2006.01) |

(52) U.S. Cl.
CPC ........ *A61K 38/2278* (2013.01); *A61K 31/165* (2013.01); *A61K 31/403* (2013.01); *A61K 31/4045* (2013.01); *A61K 31/4418* (2013.01); *A61K 38/39* (2013.01); *A61K 45/06* (2013.01); *C07K 14/57563* (2013.01); *C07K 14/78* (2013.01); *A61K 38/00* (2013.01); *C07K 2319/00* (2013.01)

(58) Field of Classification Search
CPC .............. A61K 38/2278; A61K 31/165; A61K 2300/00; A61K 31/403; A61K 31/4045; A61K 31/4418; A61K 38/00; A61K 38/39; A61K 45/06; A61P 31/10; A61P 9/12; C07K 14/57563; C07K 14/78; C07K 2319/00

See application file for complete search history.

(56) References Cited

U.S. PATENT DOCUMENTS

| | | |
|---|---|---|
| 4,132,746 A | 1/1979 | Urry et al. |
| 4,187,852 A | 2/1980 | Urry et al. |
| 4,474,851 A | 10/1984 | Urry |
| 4,500,700 A | 2/1985 | Urry |
| 4,589,882 A | 5/1986 | Urry |
| 4,605,641 A | 8/1986 | Bolin et al. |
| 4,749,647 A | 6/1988 | Thomas et al. |
| 4,752,638 A | 6/1988 | Nowinski et al. |
| 4,783,523 A | 11/1988 | Urry et al. |
| 4,870,055 A | 9/1989 | Urry et al. |
| 4,898,926 A | 2/1990 | Urry |
| 5,147,855 A | 9/1992 | Gozes et al. |
| 5,234,907 A | 8/1993 | Bolin |
| 5,235,041 A | 8/1993 | Cappello et al. |
| 5,236,904 A | 8/1993 | Gerstenberg et al. |
| 5,243,038 A | 9/1993 | Ferrari et al. |
| 5,288,514 A | 2/1994 | Ellman |
| 5,376,637 A | 12/1994 | Sawai et al. |
| 5,428,015 A | 6/1995 | Kurono et al. |
| 5,445,934 A | 8/1995 | Fodor et al. |
| 5,447,912 A | 9/1995 | Gerstenberg et al. |
| 5,496,712 A | 3/1996 | Cappello et al. |
| 5,506,120 A | 4/1996 | Yamamoto et al. |
| 5,514,581 A | 5/1996 | Ferrari et al. |
| 5,519,004 A | 5/1996 | Urry |
| 5,520,672 A | 5/1996 | Urry |
| 5,527,610 A | 6/1996 | Urry |
| 5,545,617 A | 8/1996 | Dartt et al. |
| 5,624,711 A | 4/1997 | Sundberg et al. |

(Continued)

FOREIGN PATENT DOCUMENTS

| | | |
|---|---|---|
| JP | 2009-525946 A | 7/2009 |
| WO | WO 1996/032406 A1 | 10/1996 |

(Continued)

OTHER PUBLICATIONS

Massodi, Application of Thermally Responsive Elastin-like Polypeptide Fused to a Lactoferrin-derived Peptide for Treatment of Pancreatic Cancer, Molecules 2009, 14, 1999-2015 (Year: 2009).*

(Continued)

*Primary Examiner* — Marcela M Cordero Garcia

(74) *Attorney, Agent, or Firm* — Cooley LLP

(57) ABSTRACT

The present invention is based on the discovery that a VIP having a binding preference for VPAC2 can provide long-acting blood pressure control synergistically with concomitant anti-hypertensive therapies. Accordingly, methods and compositions useful for the treatment and/or amelioration of hypertension are provided.

19 Claims, 18 Drawing Sheets

Specification includes a Sequence Listing.

(56) References Cited

U.S. PATENT DOCUMENTS

| | | | |
|---|---|---|---|
| 5,641,648 A | 6/1997 | Ferrari et al. | |
| 5,681,816 A | 10/1997 | Korman | |
| 5,702,717 A | 12/1997 | Cha et al. | |
| 5,747,646 A | 5/1998 | Hakimi et al. | |
| 5,770,570 A | 6/1998 | Paul et al. | |
| 5,770,697 A | 6/1998 | Ferrari et al. | |
| 5,773,249 A | 6/1998 | Cappello et al. | |
| 5,816,259 A | 10/1998 | Rose | |
| 5,830,713 A | 11/1998 | Ferrari et al. | |
| 5,854,387 A | 12/1998 | Urry et al. | |
| 5,900,405 A | 5/1999 | Urry | |
| 5,958,881 A | 9/1999 | Korman | |
| 5,972,406 A | 10/1999 | Urry et al. | |
| 5,972,883 A | 10/1999 | Gozes et al. | |
| 5,998,588 A | 12/1999 | Hoffman et al. | |
| 6,004,782 A | 12/1999 | Daniell et al. | |
| 6,018,030 A | 1/2000 | Ferrari et al. | |
| 6,037,321 A | 3/2000 | Cox et al. | |
| 6,063,061 A | 5/2000 | Wallace et al. | |
| 6,140,072 A | 10/2000 | Ferrari et al. | |
| 6,153,655 A | 11/2000 | Martinez et al. | |
| 6,184,348 B1 | 2/2001 | Ferrari et al. | |
| 6,200,598 B1 | 3/2001 | Needham | |
| 6,258,562 B1 | 7/2001 | Salfield et al. | |
| 6,328,996 B1 | 12/2001 | Urry | |
| 6,329,209 B1 | 12/2001 | Wagner et al. | |
| 6,355,776 B1 | 3/2002 | Ferrari et al. | |
| 6,380,154 B1 | 4/2002 | Cappello et al. | |
| 6,429,188 B1 | 8/2002 | Perez et al. | |
| 6,503,534 B1 | 1/2003 | Pellet et al. | |
| 6,537,521 B2 | 3/2003 | Uzgiris | |
| 6,541,033 B1 | 4/2003 | Shah | |
| 6,582,926 B1 | 6/2003 | Chilkoti | |
| 6,593,394 B1 | 7/2003 | Li et al. | |
| 6,699,294 B2 | 3/2004 | Urry | |
| 6,852,834 B2 | 2/2005 | Chilkoti | |
| 6,998,387 B1 | 2/2006 | Goke et al. | |
| 7,084,243 B2 | 8/2006 | Glaesner et al. | |
| 7,094,755 B2 | 8/2006 | Burman et al. | |
| 7,101,843 B2 | 9/2006 | Glaesner et al. | |
| 7,138,486 B2 | 11/2006 | Habener et al. | |
| 7,141,547 B2 | 11/2006 | Rosen et al. | |
| 7,144,863 B2 | 12/2006 | DeFelippis et al. | |
| 7,176,278 B2 | 2/2007 | Prior | |
| 7,226,910 B2 | 6/2007 | Wilson et al. | |
| 7,232,879 B2 | 6/2007 | Galloway et al. | |
| 7,259,233 B2 | 8/2007 | Dodd et al. | |
| 7,271,149 B2 | 9/2007 | Glaesner et al. | |
| 7,332,473 B2 | 2/2008 | Onoue et al. | |
| 7,364,859 B2 | 4/2008 | Chilkoti | |
| 7,429,458 B2 | 9/2008 | Chilkoti | |
| 7,442,680 B2 | 10/2008 | Yong et al. | |
| 7,459,441 B2 | 12/2008 | Minagawa et al. | |
| 7,468,353 B2 | 12/2008 | Bevec | |
| 7,566,691 B2 | 7/2009 | Nestor | |
| 7,582,608 B2 | 9/2009 | Bokvist et al. | |
| 7,709,227 B2 | 5/2010 | Dagher | |
| 7,723,472 B2 | 5/2010 | Szoka | |
| 7,776,815 B2 | 8/2010 | Vanderby et al. | |
| 8,178,495 B2 | 5/2012 | Chilkoti | |
| 8,334,257 B2 | 12/2012 | Chilkoti | |
| 8,367,626 B2 | 2/2013 | Furgeson et al. | |
| 8,729,018 B2 | 5/2014 | Chilkoti | |
| 9,029,505 B2 | 5/2015 | Sadeghi et al. | |
| 9,458,218 B2 | 10/2016 | Chilkoti | |
| 9,561,262 B2 | 2/2017 | Georgopoulos et al. | |
| 9,700,598 B2 | 7/2017 | Sadeghi et al. | |
| 9,919,032 B2 * | 3/2018 | Arnold | A61K 9/0019 |
| 10,688,156 B2 * | 6/2020 | Georgopoulos | A61K 47/02 |
| 2001/0034050 A1 | 10/2001 | Chilkoti | |
| 2002/0045567 A1 | 4/2002 | Cappello et al. | |
| 2002/0099003 A1 | 7/2002 | Wilson et al. | |
| 2002/0151458 A1 | 10/2002 | Gomariz et al. | |
| 2003/0059840 A1 | 3/2003 | Chilkoti | |
| 2003/0059841 A1 | 3/2003 | Chilkoti | |
| 2003/0158092 A1 | 8/2003 | Kai et al. | |
| 2004/0063631 A1 | 4/2004 | Block | |
| 2004/0110296 A1 | 6/2004 | Vargeese et al. | |
| 2004/0234609 A1 | 11/2004 | Collier et al. | |
| 2005/0118109 A1 | 6/2005 | Block et al. | |
| 2005/0203009 A1 | 9/2005 | Pan et al. | |
| 2005/0255554 A1 | 11/2005 | Chilkoti | |
| 2006/0247156 A1 | 11/2006 | Vanderby et al. | |
| 2007/0009602 A1 | 1/2007 | Setton et al. | |
| 2007/0265197 A1 | 11/2007 | Furgeson et al. | |
| 2008/0085860 A1 | 4/2008 | Bokvist et al. | |
| 2008/0096811 A1 | 4/2008 | Bokvist et al. | |
| 2008/0108573 A1 | 5/2008 | Duggan | |
| 2008/0207492 A1 | 8/2008 | Polt et al. | |
| 2008/0221041 A1 * | 9/2008 | Block | C07K 14/57563 514/6.9 |
| 2008/0261863 A1 | 10/2008 | Whelan et al. | |
| 2008/0274961 A1 | 11/2008 | Bevec | |
| 2008/0312156 A1 | 12/2008 | Setton et al. | |
| 2008/0318845 A1 | 12/2008 | Bokvist et al. | |
| 2008/0318865 A1 | 12/2008 | Juul-Mortensen | |
| 2009/0004104 A1 | 1/2009 | Chilkoti | |
| 2009/0005315 A1 | 1/2009 | Duggan | |
| 2009/0092582 A1 | 4/2009 | Bogin et al. | |
| 2009/0175821 A1 | 7/2009 | Bridon et al. | |
| 2009/0220455 A1 | 9/2009 | Chilkoti | |
| 2009/0270317 A1 | 10/2009 | Chilkoti | |
| 2010/0016212 A1 | 1/2010 | Rubin et al. | |
| 2010/0022455 A1 | 1/2010 | Chilkoti | |
| 2010/0184651 A1 | 7/2010 | Maithal et al. | |
| 2010/0256044 A1 | 10/2010 | Roth-chiarello | |
| 2011/0039776 A1 | 2/2011 | Chilkoti | |
| 2011/0053854 A1 | 3/2011 | Fallon et al. | |
| 2011/0110916 A1 | 5/2011 | Worman et al. | |
| 2011/0123487 A1 | 5/2011 | Chilkoti | |
| 2011/0178017 A1 | 7/2011 | Sadeghi et al. | |
| 2011/0219462 A1 | 9/2011 | Delbeck et al. | |
| 2011/0236384 A1 | 9/2011 | Setton et al. | |
| 2013/0065816 A1 | 3/2013 | Coy et al. | |
| 2013/0079277 A1 | 3/2013 | Chilkoti | |
| 2013/0085099 A1 | 4/2013 | Chilkoti | |
| 2013/0116184 A1 | 5/2013 | Nichols et al. | |
| 2013/0143802 A1 | 6/2013 | Chilkoti | |
| 2013/0150291 A1 | 6/2013 | Jowett et al. | |
| 2013/0172274 A1 | 7/2013 | Chilkoti | |
| 2013/0230581 A1 | 9/2013 | Feng et al. | |
| 2013/0310329 A1 | 11/2013 | Maiuri et al. | |
| 2013/0310538 A1 | 11/2013 | Chilkoti | |
| 2013/0315878 A1 | 11/2013 | Feng et al. | |
| 2014/0024600 A1 | 1/2014 | Chilkoti et al. | |
| 2014/0039053 A1 | 2/2014 | Ohnishi | |
| 2014/0073667 A1 | 3/2014 | Morgan | |
| 2014/0088141 A1 | 3/2014 | Binch et al. | |
| 2014/0100155 A1 | 4/2014 | Madden et al. | |
| 2014/0171370 A1 | 6/2014 | Arnold et al. | |
| 2014/0213516 A1 | 7/2014 | Chilkoti | |
| 2014/0364371 A1 | 12/2014 | Setton et al. | |
| 2015/0111829 A1 | 4/2015 | Georgopoulos et al. | |
| 2016/0220642 A1 | 8/2016 | Sadeghi et al. | |
| 2017/0182130 A1 | 6/2017 | Arnold et al. | |
| 2018/0008677 A1 | 1/2018 | Sadeghi et al. | |
| 2018/0333467 A1 | 11/2018 | Georgopoulos et al. | |

FOREIGN PATENT DOCUMENTS

| | | | | |
|---|---|---|---|---|
| WO | WO 2007/057922 A1 | 5/2007 | | |
| WO | WO 2007/065226 A1 | 6/2007 | | |
| WO | WO 2007/073486 A2 | 6/2007 | | |
| WO | WO 2008/030968 A2 | 3/2008 | | |
| WO | WO 2010/080578 A1 | 7/2010 | | |
| WO | WO 2011/020091 A1 | 2/2011 | | |
| WO | WO-2011020091 A1 * | 2/2011 | | A61K 38/2278 |
| WO | WO 2012/170524 A1 | 12/2012 | | |
| WO | WO 2013/177428 A1 | 11/2013 | | |
| WO | WO 2014/081849 A1 | 5/2014 | | |
| WO | WO 2014/113434 A1 | 7/2014 | | |
| WO | WO 2015/172046 A1 | 11/2015 | | |

(56) References Cited

FOREIGN PATENT DOCUMENTS

| WO | WO 2016/081884 A2 | 5/2016 |
|---|---|---|
| WO | WO 2016/130518 A2 | 8/2016 |

OTHER PUBLICATIONS

Tan, Recent developments in liposomes, microparticles and nanoparticles for protein and peptide drug delivery, Peptides 2009 31: 184-193 (Year: 2009).*

Massodi (Application of Thermally Responsive Elastin-like Polypeptide Fused to a Lactoferrin-derived Peptide for Treatment of Pancreatic Cancer, Molecules 2009, 14: 1999-2015, of record) (Year: 2009).*

Frottin (The Proteomics of N-terminal Methionine Cleavage, Molecular & Cellular Proteomics 2006, 5:2336-2349) (Year: 2006).*

Delgado et al., "The significance of vasoactive intestinal peptide in immunomodulation", Pharmacological Reviews, 56(2): 249-290 (2004).

Domschke et al., "Vasoactive Intestinal Peptide in Man: Pharmacokinetics, Metabolic and Circulatory Effects," Gut, 19: 1049-1053 (1978).

Duggan, K.D. et al., "Effects of enalapril on vasoactive intestinal peptide metabolism and tissue levels", European Journal of Pharmacology, 358(1): 25-30 (1998).

Dvoráková, Magdalena Chottová. "Cardioprotective role of the VIP signaling system." Drug News Perspect (2005); 18(6): 387-391.

EP Application No. EP 10808864.1, Extended European Search Report dated Feb. 21, 2013, 6 pages.

EP Application No. EP 12796397.3, Extended European Search Report, dated Dec. 11, 2014, 9 pages.

Free et al. "A Phase 1, Multi-center, Randomized, Double-blind, Placebo Controlled Study to Evaluate the Safety/Tolerability, Pharmacokinetic and Hemodynamic Response Following Single Ascending Subcutaneous Doses of PB 1046 (Vasomera™) in Subjects with Essential Hypertension (Trial Registry No. NCT01523067)," PhaseBio Pharmaceuticals, p. 1, Nov. 2014. Retrieved from the Internet:<http://phasebio.com/wp-content/uploads/2014/12/AHAPresentation-FINAL-V1-12NOV2014.pdf> on Aug. 7, 2015 (Aug. 7, 2015). entire document, 1 page.

Gourlet et al., "Vasoactive Intestinal Peptide (VIP) and Pituitary Adenylate Cyclase-Activating Peptide (PACAP-27, but not PACAP-38) Degradation by the Neutral Endopeptidase EC 3.4.24.11," Biochemical Pharmacology, 54: 509-515 (1997).

Izumi et al., "Effect of Amino Terminal Methionine Residue on the Physicochemical Properties and Biological Activity of Recombinant Methionyl Human Interleukin-2 (S-6820)", Basic and Clinical Researches, vol. 24, No. 2, pp. 151-175 (and English Summary) (1990).

Kalfin et al., "Protective role of intracoronary vasoactive intestinal peptide in ischemic and reperfused myocardium." J Pharmacol Exp Ther. (1994); 268(2): 952-958.

Kobayashi et al., "Degradation of Vasoactive Intestinal Polypeptide by Rabbit Gastric Smooth Muscle Membranes," Peptides, 15(2): 323-332 (1994).

Meyer et al. "Purification of Recombinant Proteins by Fusion with Thermally-Responsive Polypeptides", Nature Biotechnology, 17: 1112-1115 (1999).

Meyer et al., "Drug targeting using thermally responsive polymers and local hyperthermia," Journal of Controlled Release, 74: 213-224 (2001).

Meyer et al., "Polypeptide Fusion Tag for Thermal Purification of Recombinant Proteins," Abstracts of Papers, 217th ACS National Meeting, Anaheim, CA, US, Mar. 21-25, 1999, BIOT-078, see abstract.

Meyer et al., "Protein Purification by Fusion with an Environmentally Responsive Elastin-Like Polypeptide: Effect of Polypeptide Length on the Purification of Thioredoxin", Biotechnology Progress, 17: 720-728 (2001).

Meyer et al., "Targeting a Genetically Engineered Elastin-like Polypeptide to Solid Tumors by Local Hypothermia," Cancer Res. , 61(4): 1548-1554 (2001).

Mori et al., "Decreases in substance P and vasoactive intestinal peptide concentrations in plasma of stroke-prone spontaneously hypertensive rats." Japanese Heart Journal (1993); 34(6): 785-794.

Mow et al. "PhaseBio Pharmaceuticals Inc," pp. 1-28, Jun. 2013, entire document. Article Retrieved from the Internet:<http://phasebio.com/wp-content/uploads/2013/12/PhaseBio-Noncon-Jefferies-Presentation-2013.pdf> on Aug. 7, 2015 (Aug. 7, 2015). entire document, 28 pages.

Onoue et al., "Long-active analague of Vasoactive Intestinal Peptide, [R15, 20, 21, L17]-VIP-GRR (IK212532), Protects Rat Alveolar L2 Cells from the Cytotoxicity of Cigarette Smoke," Regulatory Peptides, 123: 193-199 (2004).

Onoue et al., "Physicochemical and pharmacological characterization of novel vasoactive intestinal peptide derivatives with improved stability." European Journal of Pharmaceutics and Biopharmaceutics (2009); 73(1): 95-101.

Onyüksel et al., "A Novel Formulation of VIP in Sterically Stabilized Micelles Amplifies Vasodilation In Vivo," Pharmaceutical Research, 16(1): 155-160 (1999).

Önyüksel et al., "Human VIP-α: A long-acting, biocompatible and biodegradable peptide nanomedicine for essential hypertension," Peptides, 27: 2271-2275 (2006).

PCT/US2010/045605, International Preliminary Report on Patentability dated Feb. 14, 2012, 7 pages.

PCT/US2010/045605, International Search Report dated Jan. 5, 2011, 7 pages.

PCT/US2010/045605, Written Opinion dated Jan. 5, 2011, 6 pages.

PCT/US2012/041092, International Preliminary Report on Patentability, dated Dec. 10, 2013, 5 pages.

PCT/US2012/041092, International Search Report and Written Opinion, dated Sep. 21, 2012, 7 pages.

PCT/US2015/029926, International Preliminary Report on Patentability, dated Nov. 8, 2016, 8 pages.

PCT/US2015/029926, International Search Report and Written Opinion, dated Aug. 25, 2015, 11 pages.

Petkov et al., "Vasoactive intestinal peptide as a new drug for treatment of primary pulmonary hypertension." The Journal of Clinical Investigation (2003); 111(9): 1339-1346.

Pozo et al., "Tuning Immune Tolerance With Vasoactive Intestinal Peptide: A New Therapeutic Approach for Immune Disorders", Peptides, 28(9): 1833-1846 (2007).

Rubinstein et al., "Intratracheal and subcutaneous liposomal VIPl normalizes arterial pressure in spontaneously hypertensive hamsters," International Journal of Pharmaceutics, 316: 144-147 (2006).

Said et al., "Moderate pulmonary arterial hypertension in male mice lacking the vasoactive intestinal peptide gene." Circulation (2007); 115(10): 1260-1268.

Sejourne et al., "Development of a Novel Bioactive Formulation of Vasoactive Intestinal Peptide in Sterically Stabilized Liposomes," Pharmaceutical Research, 14(3): 362-365 (1997).

Suzuki et al., "Encapsulation of VIP into liposomes restores vasorelaxation in hypertension in situ," Am. J. Physiol., 271(40): H282-H287 (1996).

Unverferth et al., "Human and canine ventricular vasoactive intestinal polypeptide: decrease with heart failure." The Journal of Laboratory and Clinical Medicine (1986), 108(1): 11-16.

Uversky et al., "Structure and stability of recombinant protein depend on the extra N-terminal methionine residue: S6 permutein from direct and fusion expression systems", Biochimica et Biophysica Acta (BBA)—Protein Structure and Molecular Enzymology, 1432(2): 324-332 (1999).

Victor, Z. C., et al. "Vasopeptidase inhibition reverses myocardial vasoactive intestinal peptide depletion and decreases fibrosis in salt sensitive hypertension." European Journal of Pharmacology (2004); 485(1): 235-242.

Yang et al., "Enhanced Inhibition of Human Immunodeficiency Virus Type 1 by Met-Stromal-Derived Factor 1β Correlates with Down-Modulation of CXCR4", Journal of Virology, 73(6): 4582-4589 (1999).

(56) References Cited

OTHER PUBLICATIONS

Ye, V. Z. C., et al. "Myocardial vasoactive intestinal peptide and fibrosis induced by nitric oxide synthase inhibition in the rat." Acta Physiologica Scandinavica (2003); 179(4): 353-360.
Ameen and Robson, "Experimental Models of Duchenne Muscular Dystrophy: Relationship with Cardiovascular Disease." Open Cardiovasc Med J. (2010); 4: 265-277.
EP Application No. EP 15789718.2, Extended European Search Report dated Oct. 27, 2017, 8 pages.
EP Application No. 17163446.2, Extended European Search Report dated Feb. 21, 2018, 7 pages.
Hinkle, et al., "Activation of the vasoactive intestinal peptide 2 receptor modulates normal and atrophying skeletal muscle mass and force." Journal of Applied Physiology (2005); 98(2): 655-662.
Kowalczyk, T., et al., "Elastin-like polypeptides as a promising family of genetically-engineered protein based polymers." World Journal of Microbiology and Biotechnology (2014); 30(8): 2141-2152.
PCT/US2016/017102, International Preliminary Report on Patentability, dated Aug. 15, 2017, 14 pages.
PCT/US2016/017102, International Search Report and Written Opinion, dated Aug. 11, 2016, 19 pages.
Rafferty, et al., "Rescue of Functional F508del Cystic Fibrosis Transmembrane Conductance Regulator by Vasoactive Intestinal Peptide in the Human Nasal Epithelial Cell Line JME/CF15." Journal of Pharmacology and Experimental Therapeutics (2009); 331(1): 2-13.
Miyazaki et al., "Segmental Myocardial Strain of the Left Ventricle in Patients With Duchenne Muscular Dystrophy Using Two-Dimensional Speckle Tracking Echocardiography," J. Echocardiogr., (2008) vol. 6, No. 4, pp. 100-108.
Alcolado, et al., "VIP-dependent increase in F508del-CFTR membrane localization is mediated by PKCε," Am J Physiol Cell Physiol (2011); 301(1): C53-C65.
Amruthwar and Janorkar, "Preparation and characterization of elastin-like polypeptide scaffolds for local delivery of antibiotics and proteins," J Mater Sci: Mater Med (2012); 23(12): 2903-2912.
Chappe, et al., "Vasoactive Intestinal Peptide Increases Cystic Fibrosis Transmembrane Conductance Regulator Levels in the Apical Membrane of Calu-3 Cells through a Protein Kinase C-Dependent Mechanism," The Journal of Pharmacology and Experimental Therapeutics (2008); 327(1): 226-238.
Chastre, et al., "Vasoactive intestinal peptide and its receptors in fetuses with cystic fibrosis," Am J Physiol (1989); 257(4pt1): G561-G569.
Choi, et al., "Synergistic airway gland mucus secretion in response to vasoactive intestinal peptide and carbachol is lost in cystic fibrosis," The Journal of Clinical Investigation (2007); 117(10): 3118-3127.
Christensen, et al., "Predicting Transition Temperatures of Elastin-Like Polypeptide Fusion Proteins," Biomacromolecules (2013); 14(5): 1514-1519.
Extended European Search Report for European Application No. 16749691.8, dated Jul. 20, 2018, 17 pages.
Mathioudakis, et al. "Vasoactive Intestinal Peptide Inhaled Agonists: Potential Role in Respiratory Therapeutics," Hippokratia (2013); 17(1): 12-16.
"PhaseBio Announces Promising Pre-clinical Results for PB1046 in Models of Duchenne Muscular Dystrophy," Apr. 22, 2015, XP002781492, retrieved from https://phasebio.com/phasebio-announces-promising-pre-clinicalresults-for-pb1046-in-models-of-duchenne-muscular-dystrophy/ [retrieved on May 29, 2018].
Qu, et al "Activation of CFTR Trafficking and Gating by Vasoactive Intestinal Peptide in Human Bronchial Epithelial Cells," Journal of Cellular Biochemistry (2011); 112(3): 902-908.
Savage, et al., "Cystic fibrosis, vasoactive intestinal polypeptide, and active cutaneous vasodilation," J Appl Physiol (1990); 69(6):2149-2154.

* cited by examiner

FIGURE 1

SEQ ID NO. 14

<u>M-VIP ELP1-120</u> (M added to N terminus of VIP)

```
MHSDAVFTDNYTRLRKOMAVKKYLNSILN
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGWP (SEQ ID NO: 14)
```

ELP1-120 = $(VPGXG)_{120}$ where X = $V_5G_3A_2$

FIGURE 2

SEQ ID NO. 15

MAA-VIP ELP1-120 (before processing, MAA added to N terminus of VIP)

MAAHSDAVFTDNYTRLRKOMAVKKYLNSILN
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGWP (SEQ ID NO: 15)

ELP1-120 = $(VPGXG)_{120}$ where $X = V_5G_3A_2$

FIGURE 4

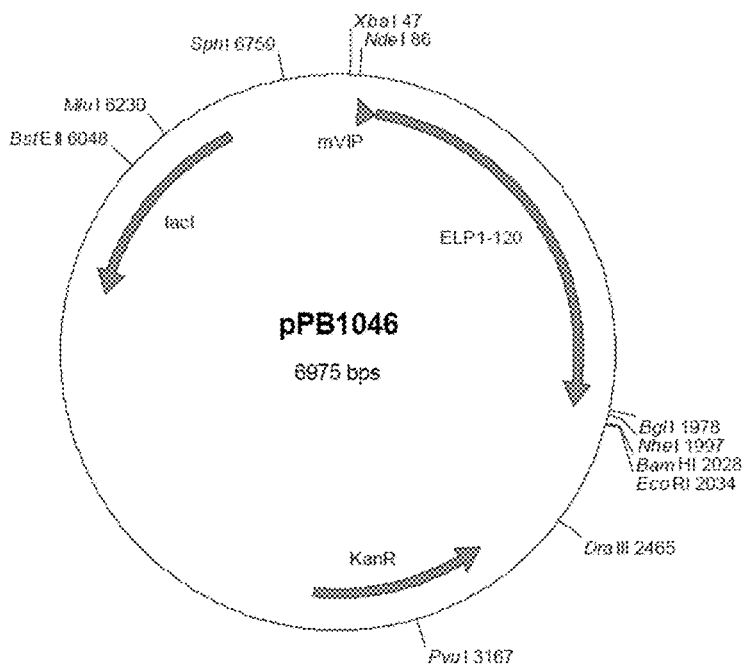

```
                                                    XbaI
                                                    -+------
                                                         P0045
                                              aattctcta gaaataattt
   1  taatacgact cactataggg gaattgtgag cggataacaa ttcccctcta gaaataattt
      attatgctga gtgatatccc cttaacactc gcctattgtt aagggagat ctttattaaa NdeI
                             ---+-----

P0064
                                              ctgttttca ctgacaacta
                      P0045 >
           tgtttaactt taaaaggag atatacatat gcactctgac g
  61  tgtttaactt taagaaggag atatacatat gcactctgac gctgttttca ctgacaacta
      acaaattgaa attcttcctc tatatgtata cgtgagactg cgacaaaagt gactgttgat
                                                      P0064
                                          >>>..........mVIP..............>
                                              m  h  s  d  a  v  f  t  d  n P0064 >
           cactctgctg cgtaaacaga tggctgttaa aaagtacctg aactctatcc tgaacgtac
 121  cactgtctg cgtaaacaga tggctgttaa aaagtacctg aactctatcc tgaacgtacc
      gtgagcagac gcatttgtct accgacaatt tttcatggac ttgagatagg acttgcatgg P0064
           >.........mVIP.......................>>>>..
               y  t  r  l  r  k  q  m  a  v  k  k  y  l  n  s  i  l  n  v 181  gggtgtgggt gttccgggcg tgggtgttcc gggtggcggt gtccgggcg caggtgttcc
      cccacaccca caaggcccgc acccacaagg cccaccgcca caggcccgc gtccacaagg
      >>............................ELP1-120...............................>
          p  g  v  g  v  p  g  v  g  v  p  g  g  g  v  p  g  a  g  v
```

FIGURE 12
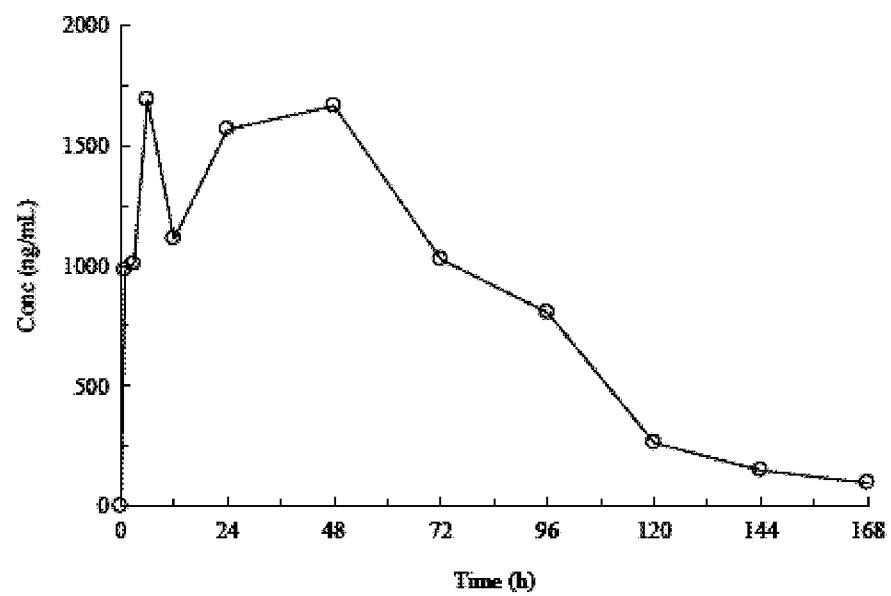
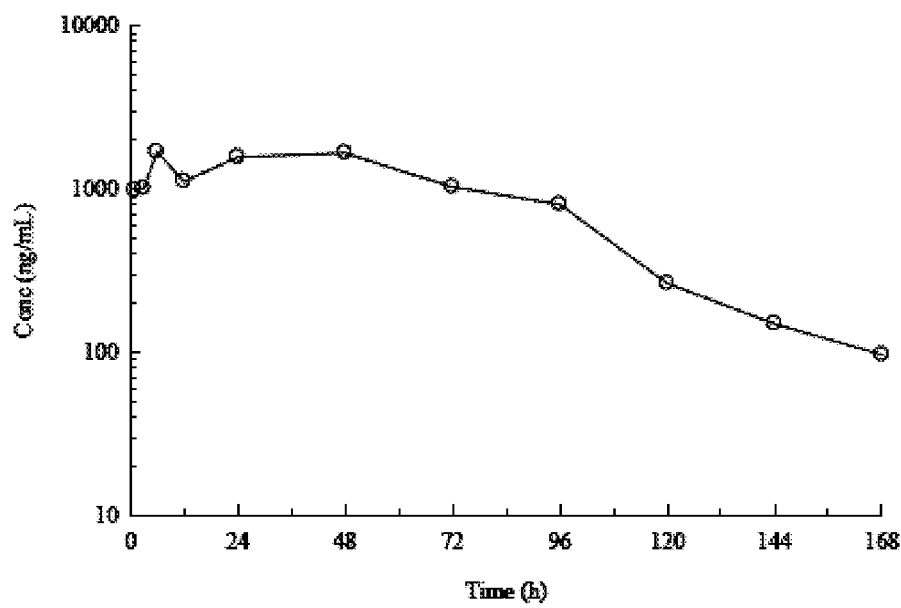

USE OF MODIFIED VASOACTIVE INTESTINAL PEPTIDES IN THE TREATMENT OF HYPERTENSION

CROSS-REFERENCE TO RELATED APPLICATIONS

This application is a continuation of U.S. Utility Application No. 14/124,612, filed Nov. 4, 2014, which is a U.S. National Phase application of PCT/US2012/041092, filed Jun. 6, 2012 and claims priority to and the benefit of U.S. Provisional Application No. 61/493,845, filed Jun. 6, 2011, which is herein incorporated by reference in its entirety.

FIELD OF THE INVENTION

The present invention relates to methods and pharmaceutical compositions for treating hypertension. More particularly, the present invention relates to treatment of hypertension using a combination of a modified vasoactive intestinal peptide (VIP) having a binding preference for the VPAC2 receptor and at least one anti-hypertensive drug.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: PHAS_022_02US_SeqList_ST25.txt, date recorded Sep. 26, 2016, file size 104 kb).

BACKGROUND

Hypertension is a prevalent medical condition characterized by abnormally high blood pressure in the arteries. Approximately 65 million adults in the United States are affected by hypertension. See Egan et al., 2010, *JAMA* 303(20): 2043-2050. The condition also affects children and teens. Clinically, hypertension is defined as a systolic pressure of 140 mm Hg or higher and a diastolic pressure of 90 mm Hg or higher. Left untreated, high blood pressure increases the risk of cardiovascular complications such as aneurysm, heart attack, heart failure, as well as renal failure.

Current treatments for hypertension include lifestyle changes as well as drug therapy. The major classes of anti-hypertensive drugs include, for example, angiotensin converting enzyme (ACE) inhibitors, β1 receptor antagonists (beta adrenergic antagonists), calcium channel blockers, and diuretics. However, a significant number of hypertensive patients are resistant and do not respond to such drugs. Accordingly, there remains a continuing need for new methods of treating hypertension.

SUMMARY OF THE INVENTION

The present invention is based in-part on the discovery that a modified vasoactive peptide (VIP) having a binding preference for VPAC2 can provide long-acting blood pressure control synergistically with concomitant anti-hypertensive therapies. Accordingly, the present invention provides methods and compositions for treating hypertension comprising administering to a patient a VIP having a binding preference for VPAC2 and at least one anti-hypertensive drug.

In one aspect, the invention provides a method of treating hypertension in a patient, comprising administering to the patient a VIP having a binding preference for VPAC2 and at least one anti-hypertensive drug selected from a β1 receptor antagonist, an ACE inhibitor, and a calcium channel blocker. The present invention is useful in treating, for example, pulmonary hypertension, uncontrolled essential hypertension, or resistant hypertension. In some embodiments, the patient has chronic heart failure, and the modified VIP is an adjunctive therapy. In some embodiments, the invention comprises administering the VIP having a binding preference for VPAC2 to a patient under going treatment for hypertension, including treatment with one or more of a β1 receptor antagonist, an ACE inhibitor, and a calcium channel blocker.

The present invention contemplates the use of a modified VIP having a binding preference for VPAC2. In an embodiment, the modified VIP induces vasorelaxation in a patient. In another embodiment, the VIP having a binding preference for VPAC2 induces decrease of any one of systolic pressure, diastolic pressure, and mean arterial pressure.

The VIP having a binding preference for VPAC2 may further have one or more of the following features. For example, the disclosed VIP may be recombinantly or chemically modified at the N- and/or C-termini by addition of one or more amino acids, and/or by fusion to heterologous amino acid sequences. Such modifications may function to provide a modified receptor binding profile, a longer circulatory half-life or persistence in the body, and/or enhanced biological potency, when compared to the native 28 amino acid mature VIP.

In an embodiment, the disclosed VIP includes an N-terminal moiety that provides binding preference to VPAC2. For example, the modified VIP may include additional N-terminal amino acids, such as a single amino acid at the N-terminus (e.g., Met). In an embodiment, the disclosed VIP comprises the sequence MHS-DAVFTDNYTRLRKOMAVKKYLNSILN (SEQ ID NO: 13). The disclosed VIP may alternatively have from 1 to 5 amino acid insertions, deletions, and/or substitutions (collectively with respect to SEQ ID NO:13).

In certain embodiments, the VIP having a binding preference for VPAC2 may include a heterologous fusion partner. In an embodiment, the disclosed VIP may be fused to at least one Elastin-Like-Peptide (ELP) component, which are described in detail herein. For example, the modified VIP may be fused (e.g., by recombinant means) to the N-terminus of an ELP.

In the treatment methods, the VIP having a binding preference for VPAC2 may be administered using any suitable route of administration, such as by subcutaneous injection. In certain embodiments, the modified VIP is administered about once per day or about once per week. In an embodiment, where the modified VIP has the amino acid sequence of SEQ ID NO:14, the modified VIP is administered at a dose of about 1 microgram to about 100 milligram per kilogram of body weight. In another embodiment, the modified VIP is administered at a dose of about 10 microgram to about 10 milligram per kilogram of body weight.

The present invention contemplates the use of one of more anti-hypertensive drugs in combination with a VIP having a binding preference for VPAC2. In an embodiment, the anti-hypertensive drug and the disclosed VIP are administered separately. The anti-hypertensive drug may be a β1 receptor antagonist, an ACE inhibitor, and/or a calcium channel blocker. In an embodiment, the β1 receptor antagonist is atenolol. In another embodiment, the ACE inhibitor is ramipril. In a further embodiment, the calcium channel blocker is amlodipine.

In various embodiments, it is contemplated that co-treatment of the VIP having a binding preference for VPAC2 and the anti-hypertensive drug produces synergistic, or additive effects, or otherwise unexpected therapeutic advantages.

In a further aspect, the present invention provides a pharmaceutical composition comprising a VIP having a binding preference for VPAC2 and at least one hypertensive drug selected from a β1 receptor antagonist, an ACE inhibitor, and a calcium channel blocker. In a specific embodiment, the composition is formulated for once per day dosing. In another embodiment, the composition is formulated for once per week dosing.

DESCRIPTION OF THE FIGURES

FIG. 1 shows the amino acid sequence of a modified VIP-ELP fusion protein (M-VIP-ELP1-120, SEQ ID NO: 14) having Met at the N-terminus and 120 ELP1 units (VPGXG, SEQ ID NO: 3) fused to the VIP at the C-terminus.

FIG. 2 shows the amino acid sequence of a modified VIP-ELP fusion protein (MAA-VIP-ELP1-120, SEQ ID NO: 15) having Met-Ala-Ala at the N-terminus, which is activatable to the natural mature VIP peptide, and 120 ELP1 units (VPGXG, SEQ ID NO: 3) fused to the VIP at the C-terminus.

FIG. 4 depicts pPB1046 encoding an M-VIP-ELP1-120 (SEQ ID NO: 23) fusion protein. Primers (P0045, SEQ ID NO: 16, P0048, SEQ ID NO: 17, and P0065, SEQ ID NO: 18) for construction of the recombinant gene are shown.

FIG. 12A shows the pharmacokinetic profile of the VIP-ELP fusion protein PB1120 in monkeys (n=3) following single subcutaneous injection of 3 mg/kg with linear axes. FIG. 12B shows the pharmacokinetic profile of the VIP-ELP fusion protein PB1120 with semi-logarithmic axes.

DETAILED DESCRIPTION OF THE INVENTION

Figure 3:
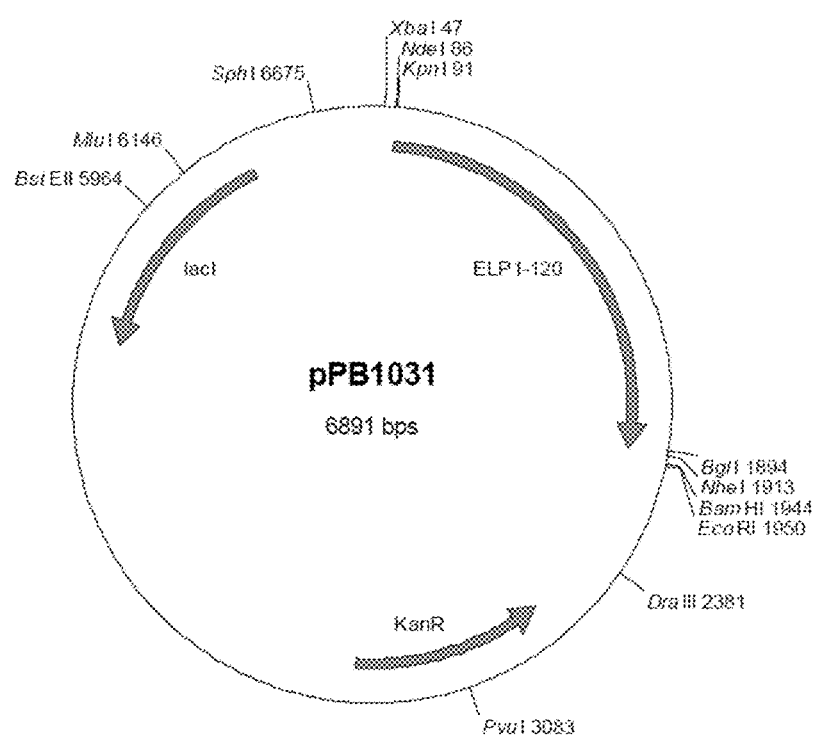
FIG. 3 is a plasmid map of pPB1031, which encodes ELP1-120 for convenient production of recombinant fusions.

The present invention relates to methods and compositions that are useful in treating hypertension. More specifically, the present invention is based in part on the discovery that a VIP having a binding preference for VPAC2 can provide synergistic blood pressure control with concomitant anti-hypertensive therapies. Accordingly, the present invention provides specific advantages for treating hypertension such as sustained blood pressure control, enhanced efficacy of treatment, and/or reduced side effects. In some embodiments, the patient has congestive heart failure, and the VIP is an adjunctive therapy.

Vasoactive intestinal peptide (VIP) is a peptide hormone containing 28 amino acid residues. VIP exhibits a wide variety of biological actions including, for example, systemic vasodilation, hypotension, coronary dilation, bronchodilation, and increased cardiac output in animals and humans. More specifically, VIP has a beneficial effect on blood and pulmonary pressure and has great potential as a therapeutic agent for hypertension.

There are at least two receptors for VIP, including the Vasoactive Intestinal Peptide Receptor 1 (VPAC1) and the Vasoactive Intestinal Peptide Receptor 2 (VPAC2). These receptors bind both VIP and the related molecule pituitary adenylate cyclase-activating polypeptide (PACAP). Both receptors are members of the seven-transmembrane G-protein coupled receptor family. VPAC1 is distributed, for example, in the central nervous system (CNS), liver, lung, intestine and T-lymphocytes. VPAC2 is found, for example, in the CNS, pancreas, skeletal muscle, heart, kidney, adipose tissue, testis, and stomach.

Nonetheless, the short half-life of VIP renders the natural peptide impractical as a pharmaceutical agent. See Pozo D, et al., *Peptides* 28(9):1833-1846 (2007). Indeed, studies have shown that the half-life of VIP in blood is less than two minutes (Domschke et al., 1978, *Gut* 19: 1049-53; Burhol et al., 1978, *Scand J Gastroent* 13: 807-813). Further, the multitude of biological effects of VIP may complicate its development for any particular indication.

In various embodiments described herein, the present invention provides methods of treating hypertension in a patient, comprising administering an effective amount of a VIP having a binding preference for VPAC2 and one or more anti-hypertensive drugs, or administering a VIP having binding preference for VPAC2 to a patient undergoing treatment with one or more of a β1 receptor antagonist, an ACE inhibitor, and a calcium channel blocker. Forms of hypertension treatable with the present invention include pulmonary hypertension, uncontrolled essential hypertension, and resistant hypertension.

Pulmonary hypertension is a relatively rare but highly fatal disease characterized by progressive pulmonary arterial hypertension and increased thickening of smaller pulmonary arteries and arterioles, culminating in right ventricular (RV) failure (Said et al., 2007, *Circulation* 115: 1260-8). VIP has been linked to pulmonary and systemic circulation. With respect to the pulmonary vascular bed and its alterations in pulmonary hypertension, VIP relaxes pulmonary vascular smooth muscle from several mammalian species in vitro, neutralizes or attenuates the actions of endothelin and other vasoconstrictors, reduces hypoxic pulmonary vasoconstriction, and inhibits the proliferation of pulmonary vascular smooth muscle from patients with pulmonary hypertension. Furthermore, VIP is a cotransmitter of the physiological nonadrenergic, noncholinergic system of pulmonary vascular smooth muscle relaxation.

Uncontrolled essential hypertension is blood pressure that is consistently higher than normal when no cause for the high blood pressure can be found. Essential hypertension is the most prevalent hypertension type, affecting 90-95% of hypertensive patients (Carretero et al., 2000, *Circulation* 101: 329-35). Concentrations of VIP are decreased in stroke-prone, essential hypertensive rats (Mori et al., 1993, *Jpn Heart J.* 34: 785-94) and use of human VIP with sterically stabilized liposomes can normalize systemic arterial pressure in spontaneously hypertensive hamsters (Onyuksel et al., 2006, *Peptides* 27: 2271-5).

Resistant hypertension is a form of high blood pressure that does not respond to treatment (i.e., blood pressure remains high even when a combination of drugs is administered). The causes of poor blood pressure control are numerous. The most likely causes are volume overload either due to excess sodium intake, intolerance to medications, noncompliance and secondary hypertension (Graves J W, 2000, *Mayo Clin Prac* 75: 278-84).

Current treatments for hypertension include lifestyle changes as well as drug therapy. Of the non-pharmacological treatments for hypertension, weight reduction and salt restriction have been considered to be the most successful. However, a number of medications are available for those patients whose blood pressure cannot be maintained in an acceptable range by non-pharmacological means. The major classes of anti-hypertensive drugs include, for example, angiotensin converting enzyme (ACE) inhibitors, β1 receptor antagonists (beta adrenergic antagonists), calcium channel blockers, and diuretics.

Angiotensin Converting Enzyme (ACE) inhibitors block the production of angiotensin II, a hormone that normally causes vasoconstriction. As a result, the blood vessels dilate, and blood pressure is reduced. In addition, angiotensin II stimulates the release of aldosterone, a hormone which is responsible for sodium retention. Accordingly, ACE inhibitors also lower blood pressure by mimicking the effect of diuretics. Examples of ACE inhibitors include, for example, enalapril, captopril, fosinopril, lisinopril, moexipril, perindopril, quinapril, ramipril, and trandolapril.

β1 receptor antagonists (beta adrenergic antagonists) block norepinephrine and epinephrine (adrenaline) from binding to beta receptors on nerves, thereby reducing heart rate. As a result, the heart beats more slowly and with less force and blood pressure is reduced. In addition, β1 receptor antagonists also cause vasodilation, thus further reducing blood pressure. Examples of β1 receptor antagonists include acebutolol, atenolol, bisoprolol, metoprolol, nadolol, nebivolol, and propranolol.

Calcium channel blockers keep calcium from entering the muscle cells of the heart and blood vessels, resulting in lowered blood pressure. More specifically, calcium channel blockers relax and dilate blood vessels by affecting the muscle cells in the arterial walls. Calcium channel blockers include, for example, amlodipine, diltiazem, felodipine, isradipine, nicardipine, nifedipine, nisoldipine, and verapamil.

Diuretics cause the body to excrete water and salt. This leads to a reduction in plasma volume, thereby lowering systemic blood pressure. Diuretics include, for example, furosemide, hydrochlorothiazide, and spironolactone.

All of the aforementioned hypertensive drugs have side effects. Further, a significant number of hypertensive patients are resistant and do not respond to such drugs. The present invention is based on the discovery that an increase in efficacy of treatment and/or reduction of side effects can be achieved by co-treatment with a modified vasoactive intestinal peptide having a binding preference for VPAC2 and one of more anti-hypertensive drugs such as an angiotensin converting enzyme (ACE) inhibitor, a beta adrenergic antagonists, and a calcium channel blocker.

Vasoactive intestinal peptide (VIP) is a peptide hormone containing 28 amino acid residues and is produced in many areas of the human body including the gut, pancreas and suprachiasmatic nuclei of the hypothalamus in the brain. VIP exhibits a wide variety of biological actions including systemic vasodilation, hypotension, increased cardiac output, respiratory stimulation, hyperglycemia, coronary dilation, bronchodilation in animals and humans. VIP also affects the balance of the immune system.

VIP has an effect on several parts of the body. With respect to the digestive system, VIP may induce smooth muscle relaxation (lower esophageal sphincter, stomach, gallbladder), stimulate the secretion of water into pancreatic juice and bile, and cause inhibition of gastric acid secretion and absorption from the intestinal lumen. Its role in the intestine is to stimulate secretion of water and electrolytes, as well as dilating intestinal smooth muscle, dilating peripheral blood vessels, stimulating pancreatic bicarbonate secretion, and inhibiting gastrin-stimulated gastric acid secretion. These effects work together to increase motility. VIP has the function of stimulating pepsinogen secretion by chief cells.

VIP has been found in the heart and has significant effects on the cardiovascular system. It causes coronary vasodilation, as well as having a positive inotropic and chronotropic effect.

Mature VIP has 28 amino acid residues with the following sequence: HSDAVFTDNYTRLRKQMAVKKYLNSILN (SEQ ID NO: 22). VIP results from processing of the 170-amino acid precursor molecule prepro-VIP. Structures of VIP and exemplary analogs have been described in U.S. Pat. Nos. 4,835,252, 4,939,224, 5,141,924, 4,734,400, 4,605,641, 6,080,837, 6,316,593, 5,677,419, 5,972,883, 6,489,297, 7,094,755, and 6,608,174, each of which is hereby incorporated by reference in its entirety for all purposes.

A number of mutations to improve peptide stability against proteases etc. are detailed in the literature (see Onune et al., *Eur. J. Pharm. Biopharm.* 2009, which is hereby incorporated by reference in its entirety for all purposes). These modified VIP peptides may have an M17L substitution to prevent oxidation of Met, one or more substitutions selected from K15R, K20R and K21R to increase proteolytic stability, and/or a substitution selected from N24A and S25A to increase proteolytic/thermal stability. The present invention provides modified VIP peptides that include one or more of these modifications, and with additional VIP modifications described herein.

In various embodiments described herein, a modified VIP (e.g., comprising SEQ ID NO: 13) (or a functional analog as described herein) is provided. Generally, functional analogs of VIP, include functional fragments truncated at the N- or C-terminus by from 1 to 10 amino acids, including by 1, 2, 3, or up to about 5 amino acids (with respect to SEQ ID NO:

13). Such functional analogs may contain from 1 to 5 amino acid insertions, deletions, and/or substitutions (collectively) with respect to the native sequence (e.g., SEQ ID NO: 22), and in each case retaining the activity of the peptide (e.g., through VPAC2 binding). Such activity may be confirmed or assayed using any available assay, including an assay described herein, and including any suitable assay to determine or quantify an activity described in Delgado et al., 2004, *Pharmacol. Reviews* 56(2):249-290. In these or other embodiments, the VIP component of the modified VIP of the invention has at least about 50%, 75%, 80%, 85%, 90%, 95%, or 97% identity with the native mature sequence (SEQ ID NO: 13). The determination of sequence identity between two sequences (e.g., between a native sequence and a functional analog) can be accomplished using any alignment tool, including that described in Tatusova et al., 1999, *FEMS Microbiol Lett.* 174:247-250.

In one aspect, the present invention provides a modified VIP molecule having receptor preference for VPAC2, as compared to unmodified VIP (e.g., a peptide consisting of the amino acid sequence of SEQ ID NO: 22). For example, the modified VIP may have a relative binding preference for VPAC2 over VPAC1 of at least about 2:1, about 5:1, about 10:1, about 25:1, about 50:1, about 100:1, about 500:1 or more. For example, in certain embodiments, the modified VIP activates the VPAC2 receptor substantially as mature, unmodified, human VIP, that is, with an EC50 within a factor of about 2 of mature, unmodified, human VIP (SEQ ID NO: 22). However, this same modified VIP is 50- or 100-fold or more less effective than mature, unmodified, human VIP in activating the VPAC1 receptor.

Such modified VIP molecules may contain modified N-terminal regions, such as an addition of from 1 to about 500 amino acids to the N-terminal histidine of VIP, which may include heterologous mammalian amino acid sequence. For example, the modified VIP may contain a single methionine at the N-terminal side of the natural N-terminal histidine of mature VIP. This molecule is also conveniently prepared in *E. coli* or other bacterial expression system, since the methionine will not be removed by *E. coli* when the adjacent amino acid is histidine. Alternatively, the N-terminal amino acid may be any of the naturally-occurring amino acids, namely alanine, arginine, asparagine, aspartic acid, cysteine, glutamic acid, glutamine, glycine, histidine, isoleucine, leucine, lysine, methionine, phenylalanine, serine, threonine, tryptophan, tyrosine, valine, and proline.

The additional sequence added to the N-terminus of VIP may be of any sequence, including biologically active and biologically inert sequences of from 1 to about 100, 1 to about 50, 1 to about 20, 1 to about 10, and 1 to about 5 amino acids.

The N-terminus of the modified VIP may have the structure M-N, where M is methionine, and N is the N-terminus of the VIP molecule (e.g., SEQ ID No. 14, FIG. 1). This methionine supports translation of the protein in a bacterial or eukaryotic host cell. Thus, the modified VIP can be made in a biological system, including bacterial and yeast expression systems (e.g., *E. coli*). While methionine can sometimes be removed by methionine aminopeptidase (MA) in bacterial expression systems, histidine (H) is one of the least favored residues at position 2 for MA.

In still other embodiments, the N-terminus is modified by fusion with a mammalian heterologous protein, such as a mammalian protein effective for extending half-life of therapeutic molecules. Such sequences may be mammalian sequences, such as albumin, transferrin, or antibody Fc sequences. Such sequences are described in, for example, U.S. Pat. No. 7,238,667 (particularly with respect to albumin conjugates), U.S. Pat. No. 7,176,278 (particularly with respect to transferrin conjugates), and U.S. Pat. No. 5,766,883, which are each hereby incorporated by reference in their entireties.

In these or other embodiments, N-terminal chemical modifications to the VIP N-terminus may provide receptor preference. Chemical modification of proteins and methods thereof are well known in the art. Non-limiting exemplary chemical modifications are PEGylation, methylglyoxalation, reductive alkylation, performic acid oxidation, succinylation, aminoethylation, and lipidation (Clifton, New Protein Techniques, New Jersey: Humana Press (1985) ISBX. 0-89603-126-8. Volume. 3 of. Methods in Molecular Biology). Chemical groups, such as PEGylation, may be attached by modifications of cysteine, methionine, histidine, lysine, arginine, tryptophan, tyrosine, and carboxyl groups, and have been described previously (see Lundblad, Techniques in Protein Modification, CRC Press (1995)).

Fusions to Bioelastic Polymers

In some embodiments, the VIP of the invention contains an N-terminal and/or C-terminal bioelastic polymer component. A "bioelastic polymer" may exhibit an inverse temperature transition. Bioelastic polymers are known and described in, for example, U.S. Pat. No. 5,520,672 to Urry et al. Bioelastic polymers may be polypeptides comprising elastomeric units of pentapeptides, tetrapeptides, and/or nonapeptides (e.g. "elastin-like peptides"). Bioelastic polymers that may be used to carry out the present invention are set forth in U.S. Pat. No. 4,474,851, which describes a number of tetrapeptide and pentapeptide repeating units that can be used to form a bioelastic polymer. Specific bioelastic polymers are also described in U.S. Pat. Nos. 4,132,746; 4,187,852; 4,500,700; 4,589,882; and 4,870,055. Still other examples of bioelastic polymers are set forth in U.S. Pat. No. 6,699,294, U.S. Pat. No. 6,753,311, and U.S. Pat. No. 6,063,061. The structures of such bioelastic polymers are hereby incorporated by reference.

In one embodiment, the bioelastic polymers are polypeptides of the general formula $(VPGXG)_m$ where X is any amino acid (e.g., Ala, Leu, Phe) and m is from about 20 to about 2000, or about 50 to about 180. In exemplary embodiments, m is 60, 90, 120, 150, or 180. The frequency of the various amino acids as the fourth amino acid can be changed, as well as the identity of X.

For example, bioelastic polymers may comprise repeating elastomeric units selected from bioelastic pentapeptides and tetrapeptides, where the repeating units comprise amino acid residues selected from the group consisting of hydrophobic amino acid and glycine residues and where the repeating units exist in a conformation having a beta-turn of the formula:

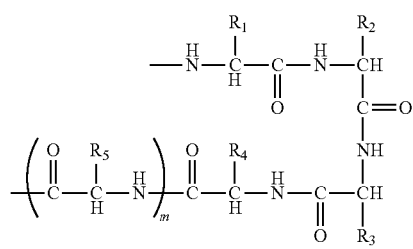

wherein $R_1$-$R_5$ represent side chains of amino acid residues 1-5, and m is 0 when the repeating unit is a tetrapeptide or 1 when the repeating unit is a pentapeptide. Nonapeptide repeating units generally consist of sequential tetra- and pentapeptides. Hydrophobic amino acid residues are selected from alanine, valine, leucine, isoleucine, proline, phenylalanine, tryptophan, and methionine. In many cases, the first amino acid residue of the repeating unit is a residue of valine, leucine, isoleucine or phenylalanine; the second amino acid residue is a residue of proline; the third amino acid residue is a residue of glycine; and the fourth amino acid residue is glycine or a very hydrophobic residue such as tryptophan, phenylalanine or tyrosine. Particular examples include the tetrapeptide Val-Pro-Gly-Gly, the tetrapeptide GGVP, the tetrapeptide GGFP, the tetrapeptide GGAP, the pentapeptide Val-Pro-Gly-Val-Gly, the pentapeptide GVGVP, the pentapeptide GKGVP, the pentapeptide GVGFP, the pentapeptide GFGFP, the pentapeptide GEGVP, the pentapeptide GFGVP, and the pentapeptide GVGIP. See, e.g., U.S. Pat. No. 6,699,294.

In certain exemplary embodiments, the VIP of the invention contains an N-terminal and/or C-terminal ELP component. The ELP component comprises or consists of structural peptide units or sequences that are related to, or derived from, the elastin protein. Such sequences are useful for improving the properties of therapeutic proteins in one or more of bioavailability, therapeutically effective dose and/or administration frequency, biological action, formulation compatibility, resistance to proteolysis, solubility, half-life or other measure of persistence in the body subsequent to administration, and/or rate of clearance from the body. See, for example, International Patent Publication No. WO 2008/030968 which is hereby incorporated by reference in its entirety.

When the ELP is positioned at the C-terminus of VIP, additional modifications may be made at the VIP N-terminus, such as the addition of one or more amino acids, as described above. In alternative embodiments, there are no such modifications at the VIP N-terminus.

The ELP component is constructed from structural units of from three to about twenty amino acids, or in some embodiments, from four to ten amino acids, such as five or six amino acids. The length of the individual structural units, in a particular ELP component, may vary or may be uniform. In certain embodiments, the ELP component is constructed of a polytetra-, polypenta-, polyhexa-, polyhepta-, polyocta-, and polynonapeptide motif of repeating structural units. Exemplary structural units include units defined by SEQ ID NOS: 1-12 (see below), which may be employed as repeating structural units, including tandem-repeating units, or may be employed in some combination, to create an ELP effective for improving the properties of the therapeutic component. Thus, the ELP component may comprise or consist essentially of structural unit(s) selected from SEQ ID NOS: 1-12, as defined below.

The ELP component, comprising such structural units, may be of varying sizes. For example, the ELP component may comprise or consist essentially of from about 10 to about 500 structural units, or in certain embodiments about 20 to about 200 structural units, or in certain embodiments from about 50 to about 150 structural units, or from about 75 to about 130 structural units, including one or a combination of units defined by SEQ ID NOS: 1-12. The ELP component may comprise about 120 structural units, such as repeats of structural units defined by SEQ ID NO: 3 (defined below). Thus, the ELP component may have a length of from about 50 to about 2000 amino acid residues, or from about 100 to about 600 amino acid residues, or from about 200 to about 500 amino acid residues, or from about 200 to about 400 amino acid residues.

In some embodiments, the ELP component, or in some cases the therapeutic agent, has a size of less than about 150 kDa, or less than about 100 kDa, or less than about 55 kDa, or less than about 50 kDa, or less than about 40 kDa, or less than about 30 or 25 kDa.

In some embodiments, the ELP component in the untransitioned state may have an extended, relatively unstructured and non-globular form so as to escape kidney filtration. In such embodiments, the therapeutic agents of the invention have a molecular weight of less than the generally recognized cut-off for filtration through the kidney, such as less than about 60 kDa, or in some embodiments less than about 55, 50, 45, 40, 30, or 25 kDa, and nevertheless persist in the body by at least 2-fold, 3-fold, 4-fold, 5-fold, 10-fold, 20-fold, or 100-fold longer than an uncoupled (e.g., unfused or unconjugated) therapeutic counterpart.

In these or other embodiments, the ELP component does not substantially or significantly impact the biological action of the therapeutic peptide. Thus, the VIP with ELP fusion of the present invention may exhibit a potency (biological action) that is the same or similar to its unfused counterpart. The VIP with ELP fusion of the present invention may exhibit a potency or level of biological action (e.g., as tested in vitro or in vivo) of from 10-100% of that exhibited by the unfused counterpart in the same assay. In various embodiments, the (activated) VIP with ELP fusion of the present invention may exhibit a potency or level of biological action (e.g., as tested in vitro or in vivo) of at least 50%, 60%, 75%, 80%, 90%, 95% or more of that exhibited by the unfused counterpart.

In certain embodiments, the ELP component undergoes a reversible inverse phase transition. That is, the ELP components are structurally disordered and highly soluble in water below a transition temperature (Tt), but exhibit a sharp (2-3° C. range) disorder-to-order phase transition when the temperature is raised above the Tt, leading to desolvation and aggregation of the ELP components. For example, the ELP forms insoluble polymers, when reaching sufficient size, which can be readily removed and isolated from solution by centrifugation. Such phase transition is reversible, and isolated insoluble ELPs can be completely resolubilized in buffer solution when the temperature is returned below the Tt of the ELPs. Thus, the therapeutic agents of the invention can, in some embodiments, be separated from other contaminating proteins to high purity using inverse transition cycling procedures, e.g., utilizing the temperature-dependent solubility of the therapeutic agent, or salt addition to the medium. Successive inverse phase transition cycles can be used to obtain a high degree of purity. In addition to temperature and ionic strength, other environmental variables useful for modulating the inverse transition of the therapeutic agents include pH, the addition of inorganic and organic solutes and solvents, side-chain ionization or chemical modification, and pressure.

In certain embodiments, the ELP component does not undergo a reversible inverse phase transition, or does not undergo such a transition at a biologically relevant Tt, and thus the improvements in the biological and/or physiological properties of the molecule (as described elsewhere herein), may be entirely or substantially independent of any phase transition properties. Nevertheless, such phase transition properties may impart additional practical advantages, for example, in relation to the recovery and purification of such molecules.

In the practice of the present invention, the ELP component functions to stabilize or otherwise improve the VIP component in the therapeutic composition. Subsequent to administration of the coupled VIP-ELP construct to the patient in need of the VIP therapeutic agent, the VIP component and the ELP remain coupled with one another while the VIP is therapeutically active, e.g., for the treatment and/or amelioration of hypertension.

In certain embodiments, the ELP component(s) may be formed of structural units, including but not limited to:
(a) the tetrapeptide Val-Pro-Gly-Gly, or VPGG (SEQ ID NO: 1);
(b) the tetrapeptide Ile-Pro-Gly-Gly, or IPGG (SEQ ID NO: 2);
(c) the pentapeptide Val-Pro-Gly-X-Gly (SEQ ID NO: 3), or VPGXG, where X is any natural or non-natural amino acid residue, and where X optionally varies among polymeric or oligomeric repeats;
(d) the pentapeptide Ala-Val-Gly-Val-Pro, or AVGVP (SEQ ID NO: 4);
(e) the pentapeptide Ile-Pro-Gly-X-Gly, or IPGXG (SEQ ID NO: 5), where X is any natural or non-natural amino acid residue, and where X optionally varies among polymeric or oligomeric repeats;
(e) the pentapeptide Ile-Pro-Gly-Val-Gly, or IPGVG (SEQ ID NO: 6);
(f) the pentapeptide Leu-Pro-Gly-X-Gly, or LPGXG (SEQ ID NO: 7), where X is any natural or non-natural amino acid residue, and where X optionally varies among polymeric or oligomeric repeats;
(g) the pentapeptide Leu-Pro-Gly-Val-Gly, or LPGVG (SEQ ID NO: 8);
(h) the hexapeptide Val-Ala-Pro-Gly-Val-Gly, or VAPGVG (SEQ ID NO: 9);
(I) the octapeptide Gly-Val-Gly-Val-Pro-Gly-Val-Gly, or GVGVPGVG (SEQ ID NO: 10);
(J) the nonapeptide Val-Pro-Gly-Phe-Gly-Val-Gly-Ala-Gly, or VPGFGVGAG (SEQ ID NO: 11); and
(K) the nonapeptides Val-Pro-Gly-Val-Gly-Val-Pro-Gly-Gly, or VPGVGVPGG (SEQ ID NO: 12).

Such structural units defined by SEQ ID NOS:1-12 may form structural repeat units, or may be used in combination to form an ELP component in accordance with the invention. In some embodiments, the ELP component is formed entirely (or almost entirely) of one or a combination of (e.g., 2, 3 or 4) structural units selected from SEQ ID NOS: 1-12. In other embodiments, at least 75%, or at least 80%, or at least 90% of the ELP component is formed from one or a combination of structural units selected from SEQ ID NOS: 1-12, and which may be present as repeating units.

In certain embodiments, the ELP component(s) contain repeating units, including tandem repeating units, of the pentapeptide Val-Pro-Gly-X-Gly (SEQ ID NO: 3), where X is as defined above, and where the percentage of Val-Pro-Gly-X-Gly (SEQ ID NO: 3) pentapeptide units taken with respect to the entire ELP component (which may comprise structural units other than VPGXG (SEQ ID NO: 3)) is greater than about 75%, or greater than about 85%, or greater than about 95% of the ELP component. The ELP component may contain motifs having a 5 to 15-unit repeat (e.g. about 10-unit or about 12-unit repeat) of the pentapeptide of SEQ ID NO: 3, with the guest residue X varying among at least 2 or at least 3 of the structural units within each repeat. The guest residues may be independently selected, such as from the amino acids Val, Ile, Leu, Ala, Gly, and Trp (and may be selected so as to retain a desired inverse phase transition property). Exemplary motifs include VPGXG (SEQ ID NO: 3), where the guest residues are Val (which may be present in from 40% to 60% of structural units), Gly (which may be present in 20% to 40% of structural units, and Ala (which may be present in 10% to 30% of structural units). The repeat motif itself may be repeated, for example, from about 5 to about 20 times, such as about 8 to 15 times (e.g., about 12 times), to create an exemplary ELP component. The ELP component as described in this paragraph may of course be constructed from any one of the structural units defined by SEQ ID NOS: 1-12, or a combination thereof. An exemplary ELP component is shown in FIG. 1 fused to the C-terminus of VIP.

In some embodiments, the ELP units may form a β-turn structure that provides an elastin-like property (e.g., inverse phase transition). Exemplary peptide sequences suitable for creating a β-turn structure are described in International Patent Publication No. WO 1996/032406, which is hereby incorporated by reference in its entirety. For example, the fourth residue (X) in the elastin pentapeptide sequence, VPGXG (SEQ ID NO: 3), can be altered without eliminating the formation of a β-turn.

In certain embodiments, the ELP components include polymeric or oligomeric repeats of the pentapeptide VPGXG (SEQ ID NO: 3), where the guest residue X is any amino acid. X may be a naturally occurring or non-naturally occurring amino acid. In some embodiments, X is selected from alanine, arginine, asparagine, aspartic acid, cysteine, glutamic acid, glutamine, glycine, histidine, isoleucine, leucine, lysine, methionine, phenylalanine, serine, threonine, tryptophan, tyrosine and valine. In some embodiments, X is a natural amino acid other than proline or cysteine.

The guest residue X (e.g., with respect to SEQ ID NO: 3, or other ELP structural unit) may be a non-classical (non-genetically encoded) amino acid. Examples of non-classical amino acids include: D-isomers of the common amino acids, 2,4-diaminobutyric acid, α-amino isobutyric acid, A-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general.

Selection of X may be independent in each ELP structural unit (e.g., for each structural unit defined herein having a guest residue X). For example, X may be independently selected for each structural unit as an amino acid having a positively charged side chain, an amino acid having a negatively charged side chain, or an amino acid having a neutral side chain, including in some embodiments, a hydrophobic side chain.

In still other embodiments, the ELP component(s) may include polymeric or oligomeric repeats of the pentapeptides VPGXG (SEQ ID NO:3), IPGXG (SEQ ID NO:5) or LPGXG (SEQ ID NO:7), or a combination thereof, where X is as defined above.

In each embodiment, the structural units, or in some cases polymeric or oligomeric repeats, of the ELP sequences may be separated by one or more amino acid residues that do not eliminate the overall effect of the molecule, that is, in imparting certain improvements to the therapeutic component as described herein. In certain embodiments, such one or more amino acids also do not eliminate or substantially affect the phase transition properties of the ELP component (relative to the deletion of such one or more amino acids).

The structure of the resulting ELP components may be described using the notation ELPk [$X_iY_j$-n], where k designates a particular ELP repeat unit, the bracketed capital letters are single letter amino acid codes and their corresponding subscripts designate the relative ratio of each guest residue X in the structural units (where applicable), and n describes the total length of the ELP in number of the structural repeats. For example, ELP1 [$V_5A_2G_3$-10] designates an ELP component containing 10 repeating units of the pentapeptide VPGXG (SEQ ID NO:3), where X is valine, alanine, and glycine at a relative ratio of 5:2:3; ELP1 [$K_1V_2F_1$-4] designates an ELP component containing 4 repeating units of the pentapeptide VPGXG (SEQ ID NO:3), where X is lysine, valine, and phenylalanine at a relative ratio of 1:2:1; ELP1 [$K_1V_7F_1$-9] designates a polypeptide containing 9 repeating units of the pentapeptide VPGXG (SEQ ID NO:3), where X is lysine, valine, and phenylalanine at a relative ratio of 1:7:1; ELP1 [$V_1A_8G_7$-10] designates an ELP component containing 10 repeating units of the pentapeptide VPGXG (SEQ ID NO:3), where X is valine, alanine, and glycine at a relative ratio of 1:8:7; ELP1 [V-5] designates a polypeptide containing 5 repeating units of the pentapeptide VPGXG (SEQ ID NO:3), where X is exclusively valine; ELP1 [V-20] designates a polypeptide containing 20 repeating units of the pentapeptide VPGXG (SEQ ID NO:3), where X is exclusively valine; ELP2 [5] designates a polypeptide containing 5 repeating units of the pentapeptide AVGVP (SEQ ID NO:4); ELP3 [V-5] designates a polypeptide containing 5 repeating units of the pentapeptide IPGXG (SEQ ID NO:5), where X is exclusively valine; ELP4 [V-5] designates a polypeptide containing 5 repeating units of the pentapeptide LPGXG (SEQ ID NO:7), where X is exclusively valine. Such ELP components as described in this paragraph may be used in connection with the present invention to increase the therapeutic properties of the therapeutic component.

Further, the Tt is a function of the hydrophobicity of the guest residue. Thus, by varying the identity of the guest residue(s) and their mole fraction(s), ELPs can be synthesized that exhibit an inverse transition over a 0-100° C. range. Thus, the Tt at a given ELP length may be decreased by incorporating a larger fraction of hydrophobic guest residues in the ELP sequence. Examples of suitable hydrophobic guest residues include valine, leucine, isoleucine, phenylalanine, tryptophan and methionine. Tyrosine, which is moderately hydrophobic, may also be used. Conversely, the Tt may be increased by incorporating residues, such as those selected from the group consisting of: glutamic acid, cysteine, lysine, aspartate, alanine, asparagine, serine, threonine, glycine, arginine, and glutamine; preferably selected from alanine, serine, threonine and glutamic acid.

The ELP component in some embodiments is selected or designed to provide a Tt (under physiological conditions) ranging from about 10° C. to about 80° C., such as from about 35° C. to about 60° C., or from about 38° C. to about 45° C. In some embodiments, the Tt is greater than about 40° C. or greater than about 42° C., or greater than about 45° C., or greater than about 50° C. The transition temperature, in some embodiments, is above the body temperature of the subject or patient (e.g., >37° C.) thereby remaining soluble in vivo, or in other embodiments, the Tt is below the body temperature (e.g., <37° C.) to provide alternative advantages, such as in vivo formation of a drug depot for sustained release of the therapeutic agent. See, for example, US Patent Publication No. US 2007/0009602, which is hereby incorporated by reference in its entirety.

The Tt of the ELP component can be modified by varying ELP chain length, as the Tt generally increases with decreasing molecular weight (MW). For polypeptides having a molecular weight of >100,000, the hydrophobicity scale developed by Urry et al. (International Patent Publication No. WO 1996/032406, which is hereby incorporated by reference in its entirety) provides one means for predicting the approximate Tt of a specific ELP sequence. However, in some embodiments, ELP component length can be kept relatively small, while maintaining a target Tt, by incorporating a larger fraction of hydrophobic guest residues (e.g., amino acid residues having hydrophobic side chains) in the ELP sequence. For polypeptides having a molecular weight of <100,000, the Tt may be predicted or determined by the following quadratic function: $Tt = M_0 + M_1X + M_2X^2$ where X is the MW of the fusion protein, and $M_0 = 116.21$; $M_1 = -1.7499$; $M_2 = 0.010349$.

While the Tt of the ELP component, and therefore of the ELP component coupled to a therapeutic component, is affected by the identity and hydrophobicity of the guest residue, X, additional properties of the molecule may also be affected. Such properties include, but are not limited to solubility, bioavailability, persistence, half-life, potency and safety of the molecule.

In the Examples section below, it is seen that the ELP-coupled VIP agent retains a significant amount of the native VIP's biological activity, relative to unfused forms of VIP. Additionally, it is shown that ELPs exhibit long half-lives. Correspondingly, ELPs can be used in accordance with the invention to substantially increase (e.g. by greater than 10%, 20%, 30%, 50%, 100%, 200% or more, in specific embodiments) the half-life of VIP, as conjugated with an ELP, in comparison to the half-life of the free (unconjugated) form of the therapeutic agent. The modified VIP having extended circulatory half-life may be administered from 1 to about 10 times per week, such as from 1 to about 5 times per week, or 1 to about 3 times per week. The modified VIP or pharmaceutical composition comprising the same may be administered about once daily, or about every other day, or about every third day, or about once a week (i.e. once weekly dosing).

A recombinantly-produced VIP fusion protein, in accordance with certain embodiments of the invention, includes the fusion component (e.g., ELP) and a VIP or an analog of VIP associated with one another by genetic fusion. For example, the fusion protein may be generated by translation of a polynucleotide encoding VIP or an analog of VIP cloned in-frame with the ELP component.

In certain embodiments, the ELP component and VIP or an analog of VIP can be fused using a linker peptide of various lengths to provide greater physical separation and allow more spatial mobility between the fused portions, and thus maximize the accessibility of VIP or an analog of VIP, for instance, for binding to its cognate receptor. The linker peptide may consist of amino acids that are flexible or more rigid. For example, a flexible linker may include amino acids having relatively small side chains, and which may be hydrophilic. Without limitation, the flexible linker may comprise glycine and/or serine residues. More rigid linkers may contain, for example, more sterically hindering amino acid side chains, such as (without limitation) tyrosine or histidine. The linker may be less than about 50, 40, 30, 20, 10, or 5 amino acid residues. The linker can be covalently linked to and between VIP or an analog of VIP and an ELP component, for example, via recombinant fusion.

The linker or peptide spacer may be protease-cleavable or non-cleavable. By way of example, cleavable peptide spacers include, without limitation, a peptide sequence recognized by proteases (in vitro or in vivo) of varying type, such as Tev, thrombin, factor Xa, plasmin (blood proteases), metalloproteases, cathepsins, and proteases found in other corporeal compartments. In some embodiments employing cleavable linkers, the fusion protein may be inactive, less active, or less potent as a fusion, which is then activated upon cleavage of the spacer in vivo. Alternatively, where the therapeutic agent is sufficiently active as a fusion, a non-cleavable spacer may be employed. The non-cleavable spacer may be of any suitable type, including, for example, non-cleavable spacer moieties having the formula $[(Gly)_n\text{-}Ser]_m$, where n is from 1 to 4, inclusive, and m is from 1 to 4, inclusive. Alternatively, a short ELP sequence different than the backbone ELP could be employed instead of a linker or spacer, while accomplishing the necessary effect.

In still other embodiments, the therapeutic agent is a recombinant fusion having a therapeutic component flanked on each terminus by an ELP component. At least one of said ELP components may be attached via a cleavable spacer, such that the therapeutic component is inactive, but activated in vivo by proteolytic removal of a single ELP component. The resulting single ELP fusion being active, and having an enhanced half-life (or other property described herein) in vivo.

In other embodiments, the present invention provides chemical conjugates of a VIP or an analog of VIP and the ELP component. The conjugates can be made by chemically coupling an ELP component to VIP or an analog of VIP by any number of methods well known in the art (See e.g., Nilsson et al., 2005, *Ann Rev Biophys Bio Structure* 34: 91-118). In some embodiments, the chemical conjugate can be formed by covalently linking VIP or an analog of VIP to the ELP component, directly or through a short or long linker moiety, through one or more functional groups on the therapeutic proteinacious component, e.g., amine, carboxyl, phenyl, thiol or hydroxyl groups, to form a covalent conjugate. Various conventional linkers can be used, e.g., diisocyanates, diisothiocyanates, carbodiimides, bis (hydroxysuccinimide) esters, maleimide-hydroxysuccinimide esters, glutaraldehyde and the like.

Non-peptide chemical spacers can additionally be of any suitable type, including, for example, by functional linkers described in Bioconjugate Techniques, Greg T. Hermanson, published by Academic Press, Inc., 1995, and those specified in the Cross-Linking Reagents Technical Handbook, available from Pierce Biotechnology, Inc. (Rockford, Ill.), the disclosures of which are hereby incorporated by reference, in their respective entireties. Illustrative chemical spacers include homobifunctional linkers that can attach to amine groups of Lys, as well as heterobifunctional linkers that can attach to Cys at one terminus, and to Lys at the other terminus.

In certain embodiments, relatively small ELP components (e.g., ELP components of less than about 30 kDa, 25 kDa, 20 kDa, 15 kDa, or 10 kDa), that do not transition at room temperature (or human body temperature, e.g., Tt >37° C.), are chemically coupled or crosslinked. For example, two relatively small ELP components, having the same or different properties, may be chemically coupled. Such coupling, in some embodiments, may take place in vivo, by the addition of a single cysteine residue at or around the C-terminus of the ELP. Such ELP components may each be fused to one or more therapeutic components, so as to increase activity or avidity at the target.

The present invention further provides pharmaceutical compositions comprising an effective amount of a modified VIP having a binding preference for VPAC2 and at least one anti-hypertensive drug, together with a pharmaceutically acceptable carrier, diluent, or excipient. Such pharmaceutical compositions are effective for treating or ameliorating hypertension, as described herein.

It is contemplated that each of the therapeutic agents may be administered per se as well as in various forms including pharmaceutically acceptable esters, salts, and other physiologically functional derivatives thereof. It is further contemplated that the therapeutic agents may be formulated solely, or together with other therapeutic agents. For example, the modified VIP having a binding preference for VPAC2 and the one or more anti-hypertensive drugs may be administered as a single formulation or as separation formulations.

The formulations of the therapeutic agent include those suitable for parenteral as well as non-parenteral administration. Exemplary administration modalities include oral, buccal, topical, nasal, pulmonary, subcutaneous, intramuscular, and intravenous, among others. Formulations suitable for parenteral administration are preferred.

The formulations comprising the therapeutic agent of the present invention may conveniently be presented in unit dosage forms and may be prepared by any of the methods well known in the art of pharmacy. Such methods generally include the step of bringing the therapeutic agents into association with a carrier which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation.

Formulations suitable for parenteral administration conveniently comprise a sterile aqueous preparation of the therapeutic agent, which preferably is isotonic with the blood of the recipient (e.g., physiological saline solution). Such formulations may include suspending agents and thickening agents or other microparticulate systems which are designed to target the therapeutic agent to the circulation or one or more organs. The formulations may be presented in unit-dose or multi-dose form.

In addition to the aforementioned ingredients, the formulations of this invention may further include one or more accessory ingredient(s) selected from diluents, buffers, flavoring agents, disintegrants, surface active agents, thickeners, lubricants, preservatives (including antioxidants), and the like.

While one of skill in the art can determine the desirable dose in each case (including a unit dose for depot administration), a suitable dose of the therapeutic agent having the amino acid sequence of SEQ ID NO:14 be in a range of about 1 microgram (µg) to about 100 milligrams (mg) per kilogram body weight of the recipient, or in a range of about 10 µg to about 50 mg per kilogram body weight, or in a range of about 10 µg to about 10 mg per kilogram body weight. The desired dose may be presented as one dose or two or more sub-doses administered at appropriate intervals throughout the dosing period (e.g., one week, two weeks, etc). These sub-doses can be administered in unit dosage forms, for example, containing from about 10 µg to about 500 mg, or from about 50 µg to about 200 mg, or from about 50 µg to about 100 mg of active ingredient per unit dosage form. Alternatively, if the condition of the recipient so requires, the doses may be administered as a continuous infusion.

The mode of administration and dosage forms will of course affect the therapeutic amount of the peptide active therapeutic agent that is desirable and efficacious for a given treatment application. For example, orally administered dosages can be at least twice, e.g., 2-10 times, the dosage levels used in parenteral administration methods. Depot formulations will also allow for significantly more therapeutic agent to be delivered, such that the agent will have a sustained release over time.

In accordance with certain embodiments of the invention, the VIP may be administered from 1 to about 10 times per week, such as from 1 to about 5 times per week, or 1 to about 3 times per week. The modified VIP or pharmaceutical composition comprising the same may be administered about once daily, or about every other day, or about every third day, or about once a week.

In certain embodiments, the modified VIP is administered parenterally, such as by subcutaneous or intramuscular injection. The administration may be a unit dose of the modified VIP as described herein.

The modified VIP, when administered parenterally, may be administered once per day, or once or twice per week, or from once to five times per month. In these embodiments, the modified VIP may be administered as a soluble fusion peptide, that persists in the circulation, as described herein, to provide sustained activity with relatively infrequent administration. The modified VIP may be administered as a drug depot, as also described herein, to provide a sustained release of fusion peptide into the circulation over time. See US Patent Application Publication No. 2007/0009602, which is hereby incorporated by reference.

The present invention provides methods of treating and/or ameliorating hypertension in a patient. In certain aspects, the invention is for use in combination therapy, whereby a modified vasoactive intestinal peptide having a binding preference for VPAC2 is administered to a patient undergoing therapy with one or more anti-hypertensive drugs such as an angiotensin converting enzyme (ACE) inhibitor, a β1 receptor antagonist, and/or a calcium channel blocker.

Co-administration of the modified VIP and the one or more anti-hypertensive drugs can be by concomitant administration of a single formulation or of separate formulations, e.g., a modified VIP formulation and a formulation of one or more anti-hypertensive drugs. Co-administration does not require the therapeutic agents to be administered simultaneously. Administration of separate formulations is considered "concomitant" if the timing of their administration is such that the pharmacological activities of the modified VIP and the one or more anti-hypertensive drugs overlap in time, thereby exerting a combined anti-hypertensive effect in the patient. Accordingly, the modified VIP with a binding preference for VPAC2 may be administered prior to, at the same time, or after the administration of the one or more anti-hypertensive drugs. Co-administration also does not require the therapeutic agents to be administered by the same route of administration. Rather, each therapeutic agent can be effected by any appropriate route. For example, the modified VIP may be administered subcutaneously while the calcium channel blocker may be administered orally.

The co-administration of the modified VIP with a binding preference for VPAC2 and the one or more anti-hypertensive drugs provides beneficial effects derived from the co-action of these therapeutic agents. It is contemplated that a VIP having a binding preference for VPAC2 can provide long-acting blood pressure control synergistically with concomitant anti-hypertensive therapies. Accordingly, the invention provides specific advantages such as sustained blood pressure control, enhanced efficacy of treatment, and/or reduced side effects.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Example 1

Cloning of VIP-ELP Constructs

The DNA sequence for the VIP peptide was as described in Simoncsits et al. (*Eur. J. Biochem.* 1988, 178(2):343-350, which is herein incorporated by reference in its entirety for all purposes), except that residue 17 was the native methionine and did not have either of the described C-terminal extensions.

Two initial variants were made, one with a methionine at the N-terminus, due to the required ATG start codon, (PB1046) and one with the tripeptide MAA at the N-terminus (PB1047). The methionine on PB1046 would normally be removed by methionine aminopeptidase (MA) but as histidine is the second residue and one of the least favored amino acids at this position for MA, the methionine is not removed. The methionine on PB1047 was removed to leave AA, which can then be removed in vitro or in vivo by DPPIV to give the histidine as the N-terminal residue. The VIP DNA sequence was cloned into vector pPB1031 (see FIG. 3) carrying the ELP1-120 DNA sequence to give an expression cassette under the control of the T7 promoter.

The synthetic oligonucleotides P0045, P0048, P0064 and P0065 were annealed together, digested with the restriction enzyme XbaI and ligated into the plasmid pPB1031 which had been digested with the restriction enzymes XbaI/KpnI to give expression plasmid pPB1046 (see FIG. 4).

Figure 5:
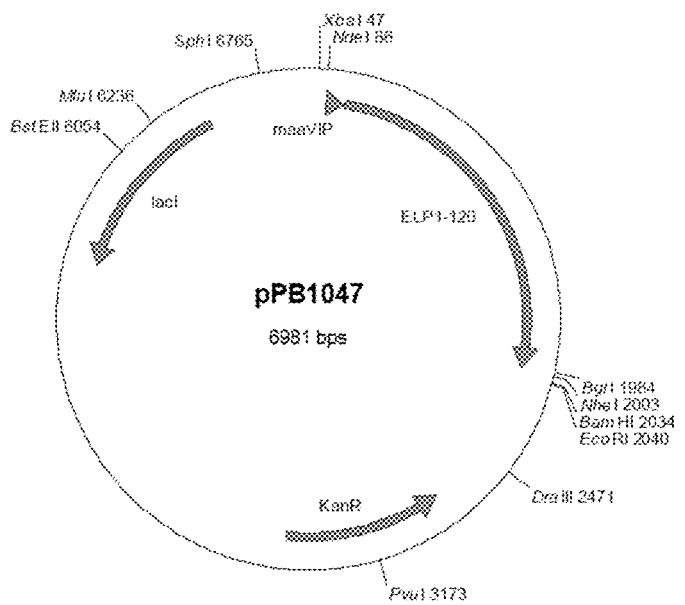
FIG. 5 depicts pPB1047 encoding an MAA-VIP-ELP1-120 (SEQ ID NO: 24) fusion protein. Primers (P0066, SEQ ID NO: 19, P0064, SEQ ID NO: 20, and P0067, SEQ ID NO: 21) for construction of the recombinant gene are shown.

The synthetic oligonucleotides P0066, P0064, P0067 and P0065 were annealed together, digested with the restriction enzyme XbaI and ligated into the plasmid pPB1031 which had been digested with the restriction enzymes XbaI/KpnI to give expression plasmid pPB1047 (see FIG. 5).

Example 2

Activity of Modified VIP-ELP Fusion Protein In Vitro

To measure the in vitro biological activity and potency of VIP or VIP-ELP fusion proteins, a cell-based bioassay was used. The assay measures the increase in intracellular cyclic adenosine monophosphate (cAMP) concentration in response to treatment with VIP or VIP-ELP fusion proteins in Chinese Hamster Ovary (CHO) cells that have been engineered to express either the human Vasoactive Intestinal Peptide Receptor 2 (VPAC2) or the human Vasoactive Intestinal Peptide Receptor 1 (VPAC1). Both VIP and VIP-ELP fusion proteins can stimulate production of cAMP in these cells, indicating that the fusion proteins retain the ability to bind and activate the receptor. Since the amount of cAMP accumulation in cells after receptor-mediated ligand binding and activation is directly proportional to the amount of intact peptide or fusion protein present, the assay can be used to determine bioactivity and relative potency.

Figure 6:
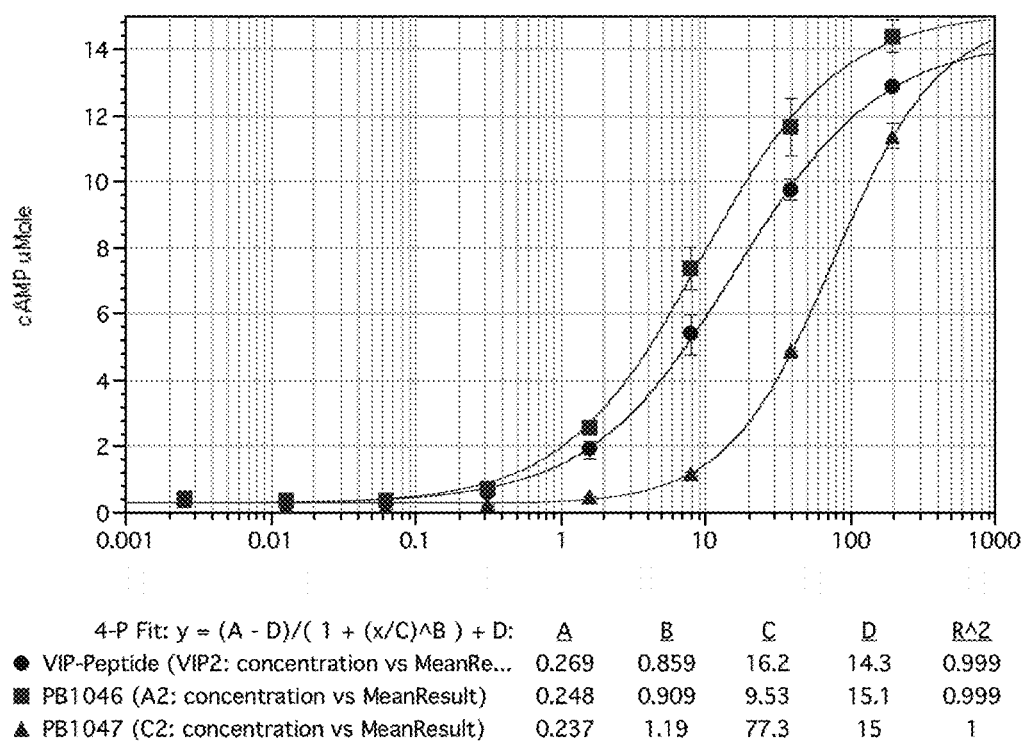
FIG. 6 shows the in vitro activity of native VIP and VIP-ELP fusion proteins PB1046 and PB1047 for VPAC2 receptor.

In this example, the activity of VIP-ELP fusion proteins PB1046 and PB1047 was tested. Construct PB1046 contains VIP with a Met at the N-terminus and construct PB1047 contains VIP with Ala-Ala at its N-terminus. Both constructs have ELP(1-120) at their C-terminus. In the first experiment, the activity of the constructs was tested using CHO cells expressing the VIP receptor VPAC2. After 30 minute incubations of various concentrations of the fusion proteins with the cell, the cells were lysed and the amount of cAMP produced was measured using a commercial kit. PB1047 was DPP-IV treated prior to the addition to the cells. FIG. 6 shows the result. As shown, modified VIP fusion protein PB1046 is somewhat more active than native VIP protein, while PB1047 is less active.

Figure 7:
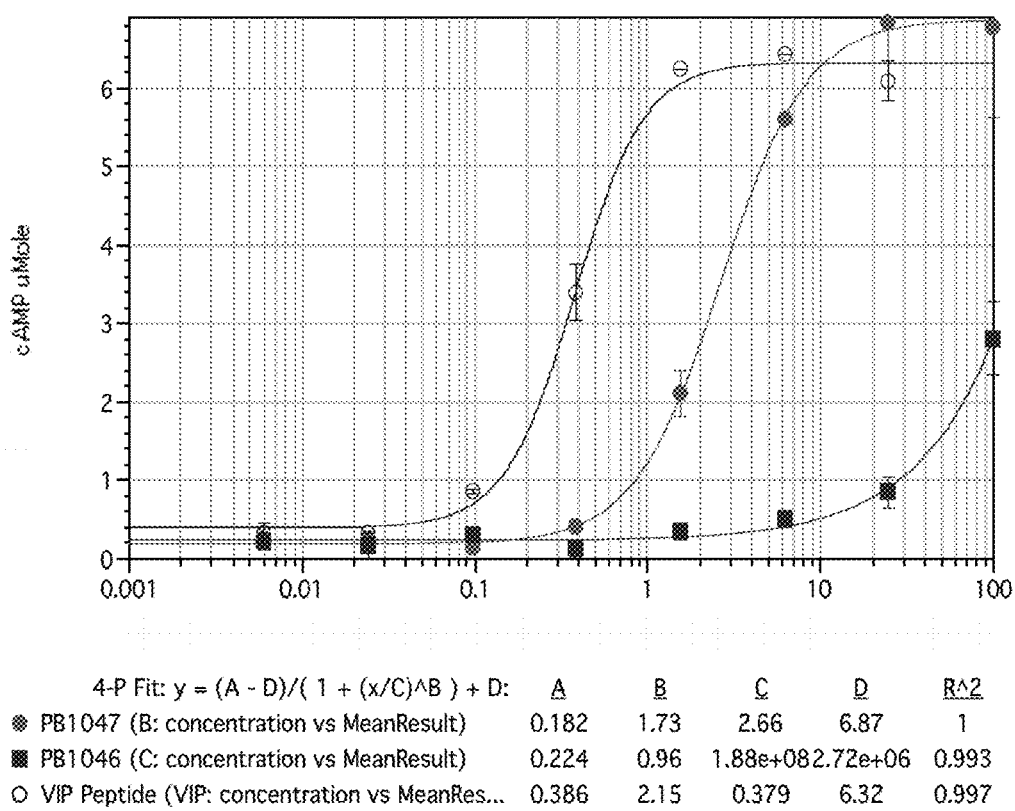
FIG. 7 shows the in vitro activity of native VIP and VIP-ELP fusion proteins PB1046 and PB1047 for VPAC1 receptor.

The activity of PB1046 and PB1047 was also tested using CHO cells expressing the VIP receptor VPAC1. After 30 minute incubations of various concentrations of the fusion proteins with CHO cells, cells were lysed and the amount of cAMP produced was measured using a commercial kit. PB1047 was DPP-IV treated prior to the addition to the cells. FIG. 7 shows the result. This time, modified VIP fusion protein PB1046 is much less active than native VIP protein, while the relative activity of PB1047 against native VIP is about the same as it was in the test for VPAC2 receptor. These results suggest that PB1046 selectively activates VPAC2 receptor over VPAC1 receptor.

Example 3

Blood Pressure Effect of VIP-ELP Fusion Protein

Figure 8:
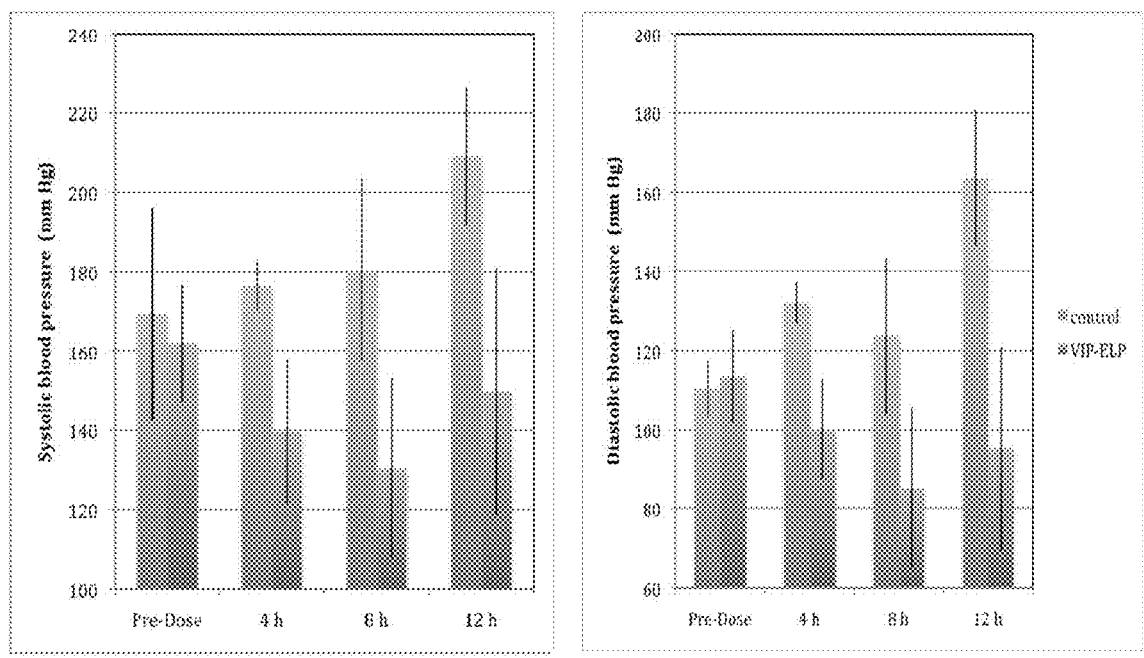
FIG. 8 shows the in vivo effect of PB1047 on rat blood pressure. Left panel shows systolic blood pressure. Right panel shows diastolic blood pressure. VIP-ELP lowers blood pressure for over a 12 hour period.

The activity of the modified VIP-ELP fusion protein PB1047 was also tested in vivo. Specifically, effects of VIP-ELP fusion protein on blood pressure were tested. Spontaneously hypertensive rats were treated subcutaneous with PB1047 (10 mg/kg) or buffer control and their blood pressures were measured at several points after administration of the fusion protein. Five animals were used for each group and the graphs show the average and the standard deviation. PB1047 significantly reduced systolic and diastolic blood pressure in these animals for at least 12 hours post administration (see FIG. 8), indicating that the VIP-ELP fusion protein is active, and can be potentially used as pharmaceuticals in treating VIP-related diseases.

Example 4

Cloning, Expression, and Analysis of an Additional VIP-ELP Fusion Protein, PB1120

Figure 9:
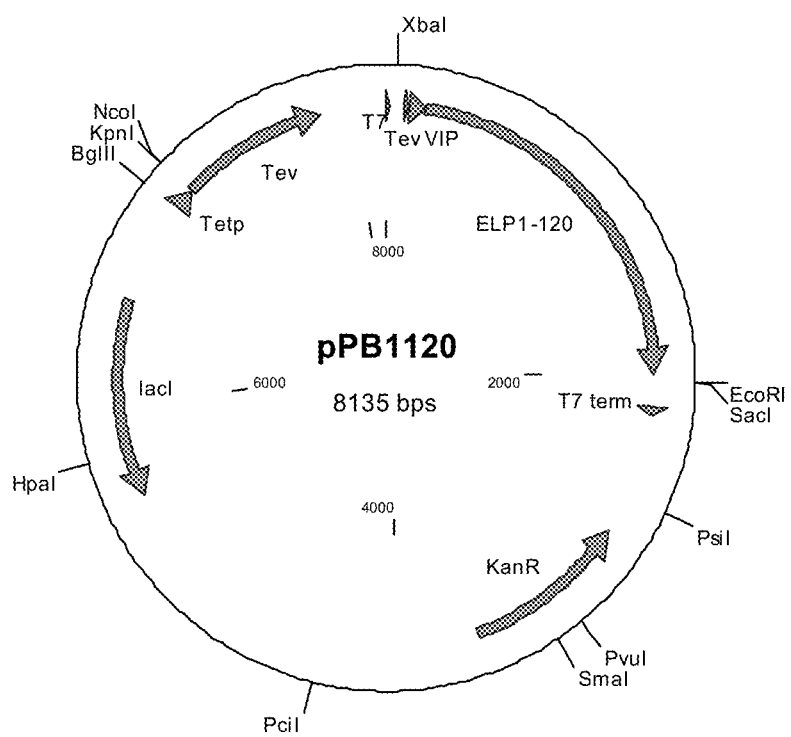
FIG. 9 is a plasmid map of pPB1120, which encodes VIP-ELP1-120.

The VIP DNA sequence was cloned into vector pPB1120 (see FIG. 9) carrying the ELP1-120 DNA sequence to give an expression cassette under the control of the T7 promoter. Next, the *E. coli* production strain BLR was transformed with the pPB1120 plasmid and grown in rich medium as described above. Samples of the resulting VIP-ELP1-120 fusion peptide, PB1120, were purified and analyzed via SDS-PAGE.

Figure 10:
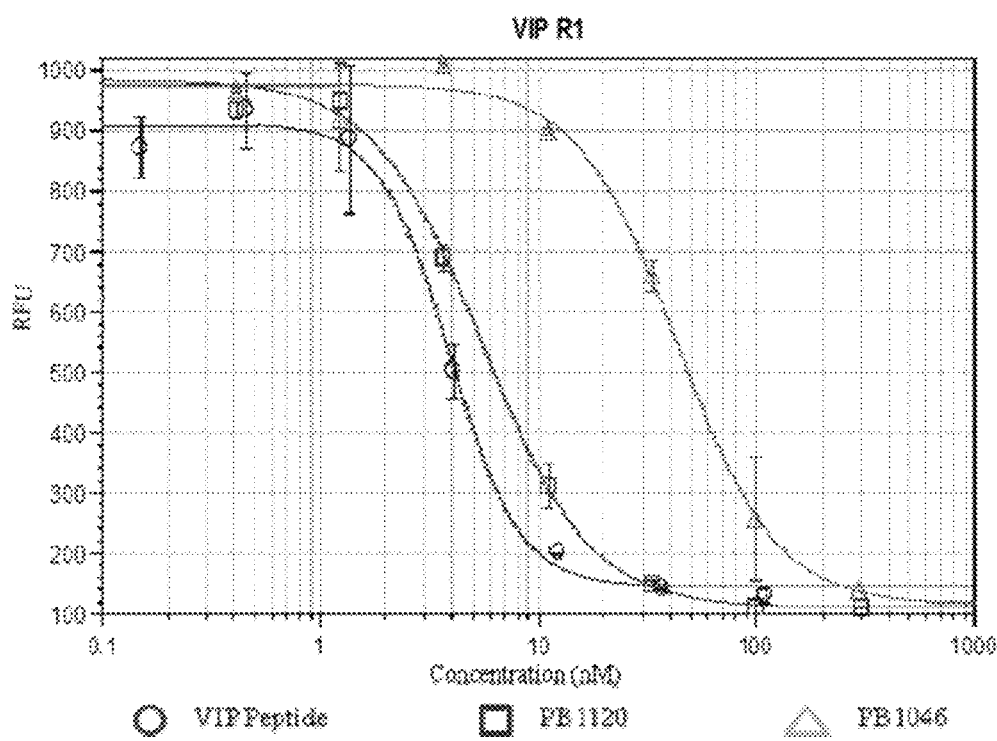
FIG. 10 shows the in vitro activity of native VIP and VIP-ELP fusion proteins PB1120 and PB1046 for VPAC1 receptor.

The activity of the PB1120 fusion peptide was tested in vitro. The activity was tested using an assay utilizing CHO cells expressing VIP receptor (VPAC1) as described above in Example 3. As FIG. 10 demonstrates, PB1120 was approximately 1.4 fold less active than the native VIP peptide on the VPAC1 receptor. By comparison, the construct PB1046 which contains an N-terminal methionine residue was approximately 11-fold less active than the native VIP peptide. Over the course of multiple experiments, PB1120 was anywhere from 1.4- to 6-fold less active than the native VIP peptide on the VPAC1 receptor.

Figure 11:
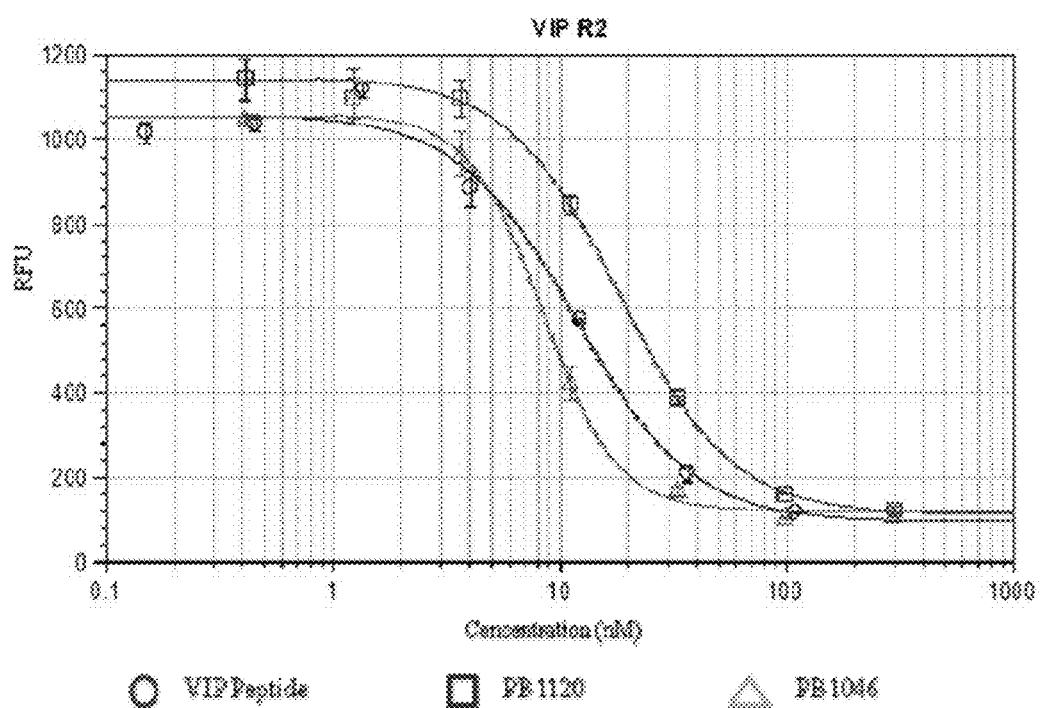
FIG. 11 shows the in vitro activity of native VIP and VIP-ELP fusion proteins PB1120 and PB1046 for VPAC2 receptor.

FIG. 11 illustrates the activity of PB1120 for the VPAC2 receptor. Like the results seen for the VPAC1 receptor, PB1120 show slightly less activity (~1.5 fold less) than the native VIP peptide for VPAC2. However, in contrast to the results seen with VPAC1, PB1046 was equipotent for VPAC2 as compared to the native peptide. Over the course of multiple experiments, PB1120 was anywhere from 1.5- to 7-fold less active than the native VIP peptide on the VPAC2 receptor.

Example 5

Pharmacokinetic Profile of Modified VIP-ELP Fusion Protein PB1120

In addition to the biological potency assays described above, the pharmacokinetic profile of the VIP-ELP fusion protein PB1120 was also examined. Monkeys were given single subcutaneous (SC) injections (dosed at 3 mg/kg) of PB1120 and plasma drug concentrations were measured daily over the course of one week. Three animals were used and the graphs show the average and the standard deviation. More than half of the initial dose of PB1120 remained in the circulation to day 4 (see FIGS. 12A and 12B, which illustrate the mean plasma concentrations of PB1120 after SC administration using linear and semi-logarithmic axes, respectively).

Based upon this data, there appears to be a prolonged absorption phase after subcutaneous administration of PB1120, consistent with slow absorption from the site of administration. The apparent elimination half-life ($t\frac{1}{2}$), based on the decay of plasma concentrations, ranged from 9.9 to 45.8 h and likely reflects the slow absorption rather than true elimination. These data indicate that the VIP-ELP fusion protein has a dramatically extended half-life in comparison to native VIP and can potentially be administered at extended intervals (e.g. may be administered about once daily, about every other day, about every third day, or about once weekly).

Example 6

Effects of Modified VIP-ELP Fusion Protein PB1120 on Blood Pressure

Figure 13A:
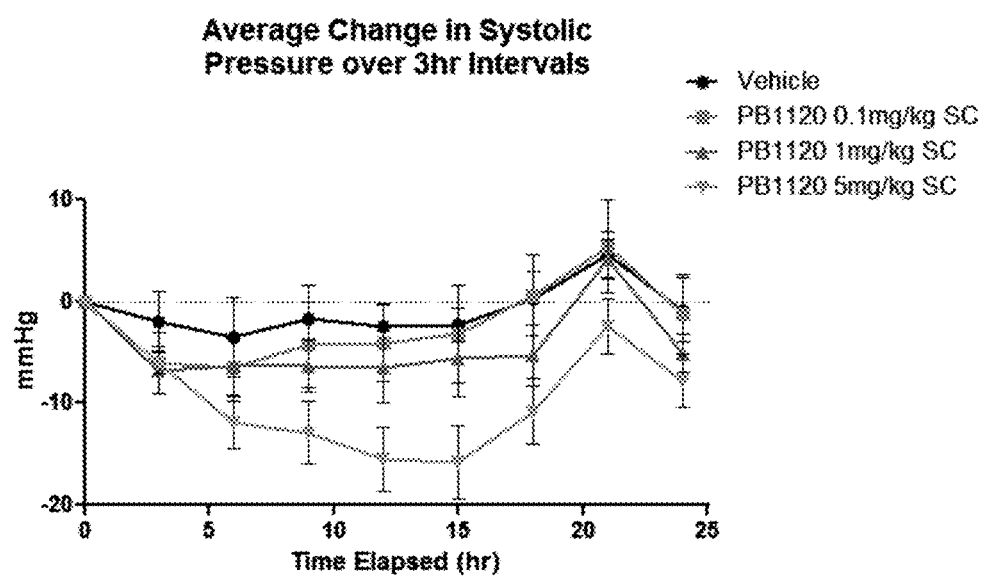
FIGS. 13A, 13B, and 13C show the average change in systolic, diastolic, and mean arterial pressure, respectively over 3 hr intervals in rats injected subcutaneously with PB1120 at 0.1 mg/kg, 1 mg/kg, or 5 mg/kg dosages.
Figure 13B:
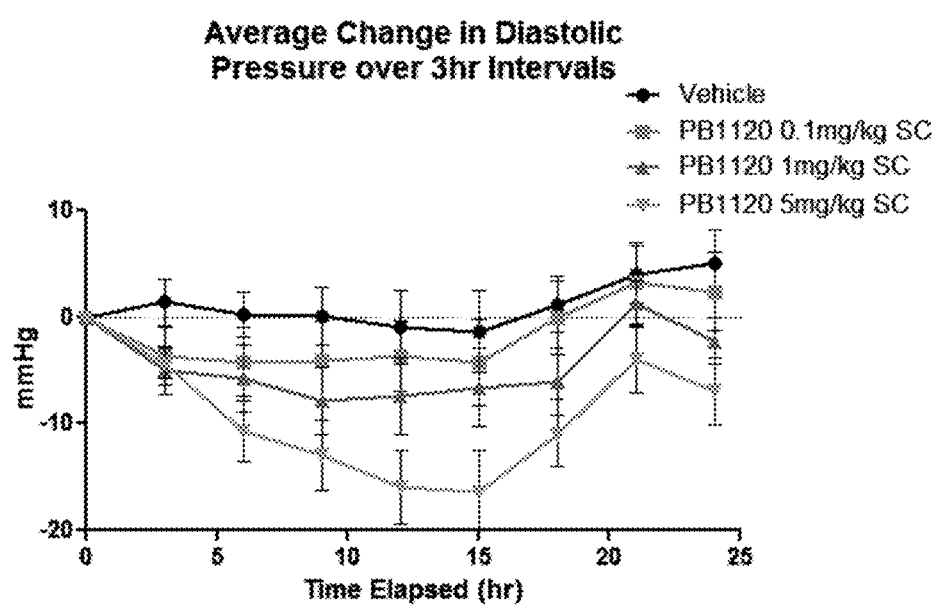
Figure 13C:
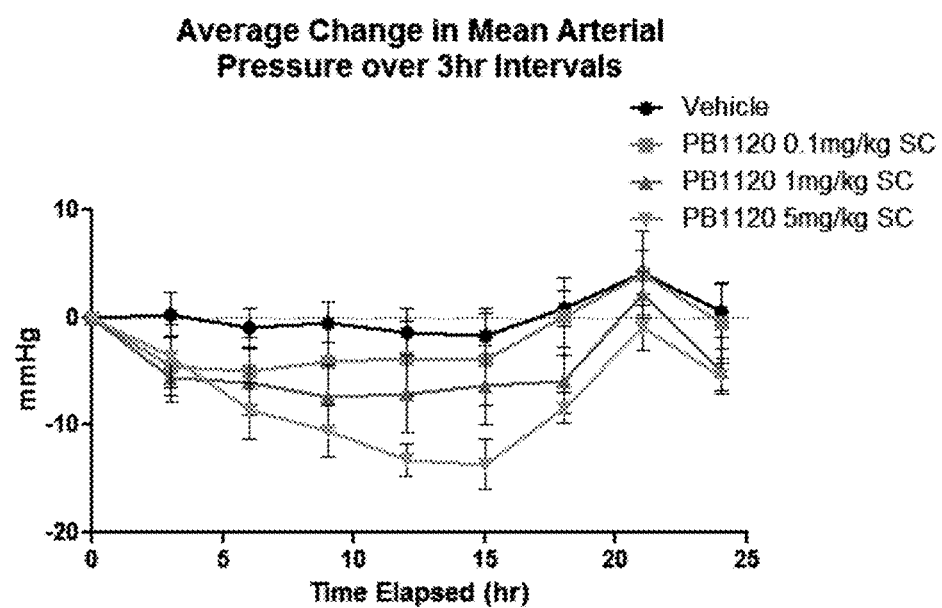
Figure 13D:
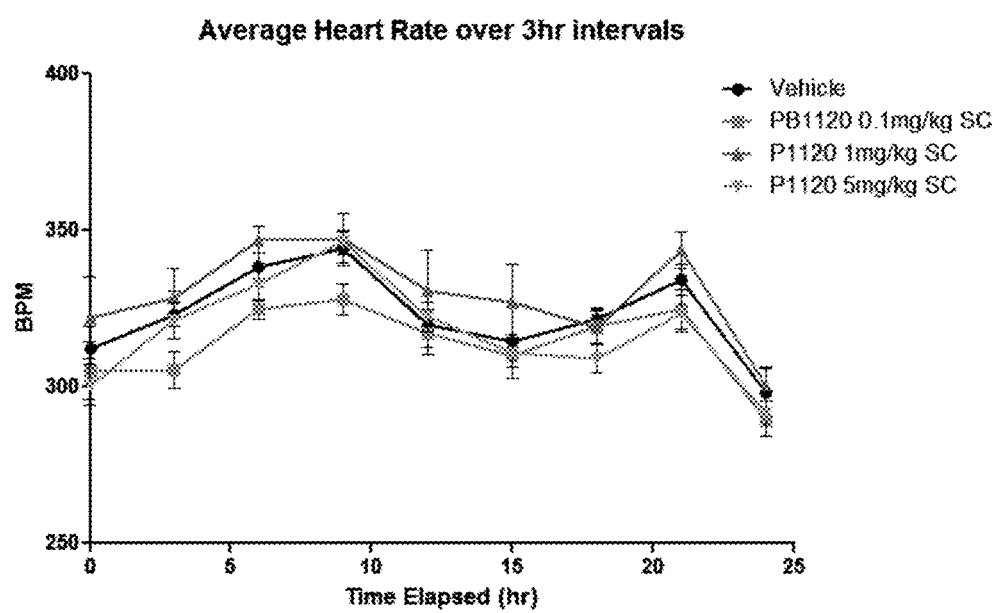
FIG. 13D shows the average heart rate of the subject rats over 3 hour intervals following administration of PB1120.

To measure the effects of the modified VIP-ELP fusion protein PB1120 on systolic, diastolic, and mean arterial blood pressure, rats were given single, subcutaneous injections of 0.1 mg/kg, 1 mg/kg, or 5 mg/kg of PB1120 and evaluated over 3-hr intervals. FIGS. 13A, 13B, and 13C show the average change in systolic, diastolic, and mean arterial pressure, respectively. FIG. 13D shows the average heart rate over 3 hr intervals following administration of PB1120. As FIGS. 13A-C demonstrate, rats injected with either 1 mg/kg or 5 mg/kg of PB1120 showed significant reductions in systolic, diastolic, and mean arterial pressure 9 hrs post-injection, indicating that VIP-ELP fusion protein PB1120 can potentially be administered for the purpose of treating or preventing hypertension in afflicted individuals.

Example 7

Blood Pressure Control with VPAC2-Selective VIP is Independent of β-AR Function

The natural vasoactive intestinal peptide (VIP) triggers potent vasodilatation by activating the G-protein-coupled VPAC1 and VPAC2 receptors; however, VIP's clinical utility is limited due to its short half-life and VPAC1-mediated side-effects. Here, the effects of PB 1046 (Vasomera™) when given as a single-dose SQ bolus to conscious spontaneously hypertensive rats (SHR) was tested.

SHR rats (351±4 g, n=8) were instrumented for telemetric blood pressure and ECG monitoring. Via a Latin-Square design, the effects of Vasomera (1, 3, and 9 mg/kg SQ) as well as of vehicle (VEH, SQ) were evaluated. Finally, Vasomera™ (9 mg/kg SQ) was assayed during concomitant β-adrenergic receptor blockade (BB, atenolol 20 mg/kg/day PO). Changes in mean arterial pressure (MAP) and heart rate (HR) were measured.

Figure 14:
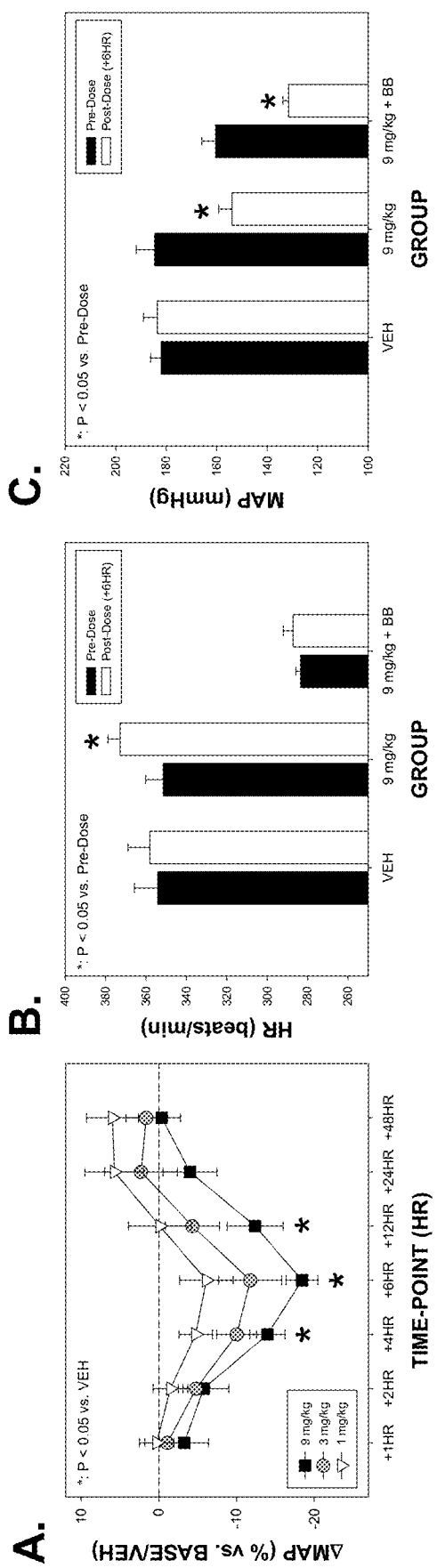
FIGS. 14A, 14B, and 14C show that dose-dependent sustained blood pressure control with PB1046 (Vasomera™) is independent of β adrenergic receptor function in spontaneously hypertensive rats.

Vasomera™ induced dose-dependent decreases in blood pressure that were sustained for up to 12 hours post-dosing (see FIG. 14A). For instance, at 9 mg/kg (177 nmol/kg), Vasomera™ lowered MAP by 16±3% (154±5 mmHg vs. 184±6 in VEH @+6 hr, P<0.05). Concomitantly, Vasomera™ triggered moderate cardio-acceleration (370±15 bpm at 9 mg/kg vs. 322±10 bpm in VEH @+2 hr, P<0.05). Notably, β-adrenergic receptor blockade blunted Vasomera™'s chronotropic effects (308±3 bpm @ +2 hr) while preserving/enhancing vaso-relaxation (MAP: 131±3 mmHg @ +6 hr) (see FIGS. 14B and 13C). No adverse clinical effects were noted.

These data suggest that Vasomera™ can provide long-acting blood pressure control synergistically with concomitant therapies (such as β-adrenergic receptor blockade) and may represent a novel adjunct therapeutic agent for resistant/uncontrolled hypertensive patients.

Example 8

Blood Pressure Control with VPAC2-Selective VIP in Conjunction with Anti-Hypertensives The hemodynamic effects of Vasomera™ when given as a single-dose SQ bolus to conscious spontaneously hypertensive rats (SHR) pretreated with three common anti-hypertensives were tested.

SHR rats (351±4 g, n=8) were instrumented for telemetric BP and ECG monitoring. First, both Vasomera™ (9 mg [177 nmol]/kg, SQ) and placebo (VEH) were assayed in untreated animals. Then, the effects of Vasomera™ were tested during concomitant oral β-adrenergic receptor blockade (+BB, atenolol 20 mg/kg/day), calcium-channel blockade (+CCB, amlodipine 5 mg/kg/day) and ACE-inhibition (+ACE, ramipril 1 mg/kg/day). Mean arterial pressure (MAP) and heart rate (HR) were measured/averaged over 24 hours both pre- and post-dosing.

Figure 15:
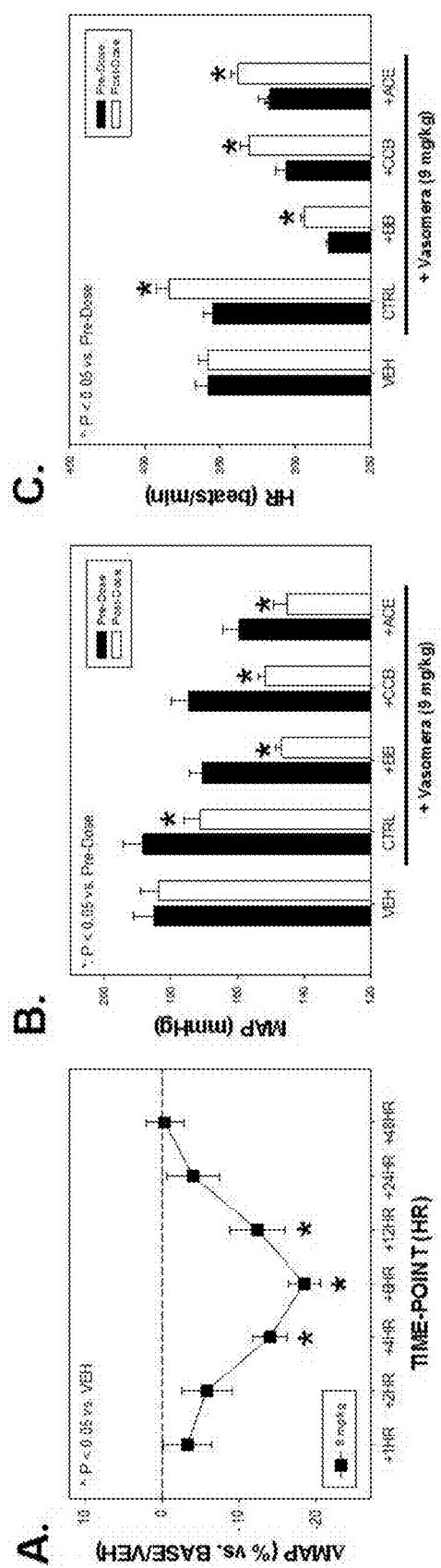
FIGS. 15A, 15B, and 15C show that co-administration of PB1046 (Vasomera™) and the anti-hypertensives—atenolol, amlodipine, or ramipril results in enhanced therapeutic effects.

Vasomera™ induced potent decreases in blood pressure that were sustained for up to 12 hours post-dosing (see FIG. 15A). On average, Vasomera™ lowered MAP by 9±1% (188±6 to 171±5 mmHg, P<0.05). Vasomera™'s vasorelaxation was preserved/enhanced in rats pre-treated with either atenolol (−14±1%, P<0.05), amlodipine (−13±2%, P<0.05), and/or ramipril (−9±2%, P<0.05) (see FIG. 15B). Vasomera™ triggered moderate cardio-acceleration in untreated rats (+8±1%, 355±6 to 384±8 bpm, P <0.05); such chronotropy was blunted under β-adrenergic receptor blockade (+6±1%, 278±2 to 294±2 bpm), but was unaffected by amlodipine or ramipril (see FIG. 15C). In all cases, heart rates were lower than in controls, and no adverse clinical effects were noted.

These results demonstrate that co-administration of Vasomera™ with concomitant anti-hypertensive therapies (e.g., β-adrenergic receptor blockade) can provide enhanced long-acting blood pressure control as well as reduced side effects.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The invention claimed is:

1. A method for treating hypertension in a patient, comprising administering to the patient: a vasoactive intestinal peptide (VIP) and at least one anti-hypertensive drug selected from a β1 receptor antagonist, an ACE inhibitor, and a calcium channel blocker, wherein the VIP comprises the amino acid sequence of SEQ ID NO: 13 with the N-terminal His at position 2, an N-terminal methionine, and an elastin-like peptide (ELP) at the C-terminus, wherein the ELP comprises at least 90 repeats of VPGXG (SEQ ID NO: 3), and wherein X is V, A, and G in a ratio of about V5, A2, and G3, and wherein the co-administration of the VIP and the anti-hypertensive drug produces reduced side effects compared to administering VIP alone.

2. The method of claim 1, wherein said hypertension is selected from pulmonary hypertension, uncontrolled essential hypertension, pulmonary arterial hypertension, and resistant hypertension.

3. The method of claim 1, wherein said vasoactive intestinal peptide induces vaso-relaxation.

4. The method of claim 1, wherein said vasoactive intestinal peptide induces a decrease of at least one of systolic pressure, diastolic pressure, and mean arterial pressure.

5. The method of claim 1, wherein said elastin-like peptide comprises 120 repeating units of VPGXG (SEQ ID NO: 3).

6. The method of claim 5, wherein said vasoactive intestinal peptide has the amino acid sequence of SEQ ID NO: 14.

7. The method of claim 1, wherein said vasoactive intestinal peptide and said anti-hypertensive drug are administered separately.

8. The method of claim 1, wherein said vasoactive intestinal peptide is administered parenterally.

9. The method of claim 8, wherein said vasoactive intestinal peptide is administered subcutaneously.

10. The method of claim 1, wherein said vasoactive intestinal peptide is administered about once per day.

11. The method of claim 1, wherein said vasoactive intestinal peptide is administered about once per week.

12. The method of claim 1, wherein said vasoactive intestinal peptide has the amino acid sequence of SEQ ID NO: 14 and is administered at a dose of about 1 microgram to about 100 milligrams per kilogram of body weight.

13. The method of claim 12, wherein said vasoactive intestinal peptide is administered at a dose of about 10 micrograms to about 10 milligrams per kilogram of body weight.

14. The method of claim 1, wherein said patient is a human patient.

15. A pharmaceutical composition comprising a vasoactive intestinal peptide (VIP) and at least one anti-hypertensive drug selected from a β1 receptor antagonist, an ACE inhibitor, and a calcium channel blocker, wherein the VIP comprises the amino acid sequence of SEQ ID NO: 13 with the N-terminal His at position 2, an N-terminal methionine, and an elastin-like peptide (ELP) at the C-terminus, and wherein the ELP comprises at least 90 repeats of VPGXG (SEQ ID NO: 3), and wherein the co-administration of the VIP and the anti-hypertensive drug produces reduced side effects compared to administering VIP alone.

16. The pharmaceutical composition of claim 15, wherein the composition is formulated for once per day dosing.

17. The pharmaceutical composition of claim 15, wherein the composition is formulated for once per week dosing.

18. The method of claim 1, wherein the VIP has a binding preference for the Vasoactive Intestinal Peptide Receptor 2 (VPAC2).

19. The pharmaceutical composition of claim 15, wherein the VIP has a binding preference for the Vasoactive Intestinal Peptide Receptor 2 (VPAC2).

* * * * *

SEQUENCE LISTING

```
<160> NUMBER OF SEQ ID NOS: 27

<210> SEQ ID NO 1
<211> LENGTH: 4
<212> TYPE: PRT
<213> ORGANISM: Artificial Sequence
<220> FEATURE:
<223> OTHER INFORMATION: ELP tetrapeptide

<400> SEQUENCE: 1

Val Pro Gly Gly
1

<210> SEQ ID NO 2
<211> LENGTH: 4
<212> TYPE: PRT
```

```
<213> ORGANISM: Artificial Sequence
<220> FEATURE:
<223> OTHER INFORMATION: ELP tetrapeptide

<400> SEQUENCE: 2

Ile Pro Gly Gly
1

<210> SEQ ID NO 3
<211> LENGTH: 5
<212> TYPE: PRT
<213> ORGANISM: Artificial Sequence
<220> FEATURE:
<223> OTHER INFORMATION: ELP pentapeptide
<220> FEATURE:
<221> NAME/KEY: MISC_FEATURE
<222> LOCATION: (4)..(4)
<223> OTHER INFORMATION: Xaa may be any natural or non-natural amino
      acid residue

<400> SEQUENCE: 3

Val Pro Gly Xaa Gly
1               5

<210> SEQ ID NO 4
<211> LENGTH: 5
<212> TYPE: PRT
<213> ORGANISM: Artificial Sequence
<220> FEATURE:
<223> OTHER INFORMATION: ELP pentapeptide

<400> SEQUENCE: 4

Ala Val Gly Val Pro
1               5

<210> SEQ ID NO 5
<211> LENGTH: 5
<212> TYPE: PRT
<213> ORGANISM: Artificial Sequence
<220> FEATURE:
<223> OTHER INFORMATION: ELP pentapeptide
<220> FEATURE:
<221> NAME/KEY: MISC_FEATURE
<222> LOCATION: (4)..(4)
<223> OTHER INFORMATION: Xaa may be any natural or non-natural amino
      acid residue

<400> SEQUENCE: 5

Ile Pro Gly Xaa Gly
1               5

<210> SEQ ID NO 6
<211> LENGTH: 5
<212> TYPE: PRT
<213> ORGANISM: Artificial Sequence
<220> FEATURE:
<223> OTHER INFORMATION: ELP pentapeptide

<400> SEQUENCE: 6

Ile Pro Gly Val Gly
1               5

<210> SEQ ID NO 7
<211> LENGTH: 5
<212> TYPE: PRT
<213> ORGANISM: Artificial Sequence
<220> FEATURE:
<223> OTHER INFORMATION: ELP pentapeptide
<220> FEATURE:
```

```
<221> NAME/KEY: misc_feature
<222> LOCATION: (4)..(4)
<223> OTHER INFORMATION: Xaa may be any natural or non-natural amino
      acid residue

<400> SEQUENCE: 7

Leu Pro Gly Xaa Gly
1               5

<210> SEQ ID NO 8
<211> LENGTH: 5
<212> TYPE: PRT
<213> ORGANISM: Artificial Sequence
<220> FEATURE:
<223> OTHER INFORMATION: ELP pentapeptide

<400> SEQUENCE: 8

Leu Pro Gly Val Gly
1               5

<210> SEQ ID NO 9
<211> LENGTH: 6
<212> TYPE: PRT
<213> ORGANISM: Artificial Sequence
<220> FEATURE:
<223> OTHER INFORMATION: ELP hexapeptide

<400> SEQUENCE: 9

Val Ala Pro Gly Val Gly
1               5

<210> SEQ ID NO 10
<211> LENGTH: 8
<212> TYPE: PRT
<213> ORGANISM: Artificial Sequence
<220> FEATURE:
<223> OTHER INFORMATION: ELP octapeptide

<400> SEQUENCE: 10

Gly Val Gly Val Pro Gly Val Gly
1               5

<210> SEQ ID NO 11
<211> LENGTH: 9
<212> TYPE: PRT
<213> ORGANISM: Artificial Sequence
<220> FEATURE:
<223> OTHER INFORMATION: ELP nonapeptide

<400> SEQUENCE: 11

Val Pro Gly Phe Gly Val Gly Ala Gly
1               5

<210> SEQ ID NO 12
<211> LENGTH: 9
<212> TYPE: PRT
<213> ORGANISM: Artificial Sequence
<220> FEATURE:
<223> OTHER INFORMATION: ELP nonapeptide

<400> SEQUENCE: 12

Val Pro Gly Val Gly Val Pro Gly Gly
1               5

<210> SEQ ID NO 13
<211> LENGTH: 29
<212> TYPE: PRT
```

<213> ORGANISM: Artificial Sequence
<220> FEATURE:
<223> OTHER INFORMATION: M-VIP

<400> SEQUENCE: 13

```
Met His Ser Asp Ala Val Phe Thr Asp Asn Tyr Thr Arg Leu Arg Lys
1               5                   10                  15

Gln Met Ala Val Lys Lys Tyr Leu Asn Ser Ile Leu Asn
            20                  25
```

<210> SEQ ID NO 14
<211> LENGTH: 634
<212> TYPE: PRT
<213> ORGANISM: Artificial Sequence
<220> FEATURE:
<223> OTHER INFORMATION: M-VIP ELP1-120

<400> SEQUENCE: 14

```
Met His Ser Asp Ala Val Phe Thr Asp Asn Tyr Thr Arg Leu Arg Lys
1               5                   10                  15

Gln Met Ala Val Lys Lys Tyr Leu Asn Ser Ile Leu Asn Val Pro Gly
            20                  25                  30

Val Gly Val Pro Gly Val Gly Val Pro Gly Gly Val Pro Gly Ala
        35                  40                  45

Gly Val Pro Gly Val Gly Val Pro Gly Val Gly Val Pro Gly Val Gly
        50                  55                  60

Val Pro Gly Gly Gly Val Pro Gly Ala Gly Val Pro Gly Gly Val
65                  70                  75                  80

Pro Gly Val Gly Val Pro Gly Val Gly Val Pro Gly Gly Val Pro
                85                  90                  95

Gly Ala Gly Val Pro Gly Val Gly Val Pro Gly Val Gly Val Pro Gly
            100                 105                 110

Val Gly Val Pro Gly Gly Gly Val Pro Gly Ala Gly Val Pro Gly Gly
        115                 120                 125

Gly Val Pro Gly Val Gly Val Pro Gly Val Gly Val Pro Gly Gly Gly
        130                 135                 140

Val Pro Gly Ala Gly Val Pro Gly Val Gly Val Pro Gly Val Gly Val
145                 150                 155                 160

Pro Gly Val Gly Val Pro Gly Gly Gly Val Pro Gly Ala Gly Val Pro
                165                 170                 175

Gly Gly Gly Val Pro Gly Val Gly Val Pro Gly Val Gly Val Pro Gly
            180                 185                 190

Gly Gly Val Pro Gly Ala Gly Val Pro Gly Val Gly Val Pro Gly Val
        195                 200                 205

Gly Val Pro Gly Val Gly Val Pro Gly Gly Val Pro Gly Ala Gly
        210                 215                 220

Val Pro Gly Gly Gly Val Pro Gly Val Gly Val Pro Gly Val Gly Val
225                 230                 235                 240

Pro Gly Gly Gly Val Pro Gly Ala Gly Val Pro Gly Val Gly Val Pro
                245                 250                 255

Gly Val Gly Val Pro Gly Val Gly Val Pro Gly Gly Gly Val Pro Gly
            260                 265                 270

Ala Gly Val Pro Gly Gly Gly Val Pro Gly Gly Val Pro Gly Val
        275                 280                 285

Gly Val Pro Gly Gly Gly Val Pro Gly Ala Gly Val Pro Gly Val Gly
        290                 295                 300
```

Val Pro Gly Val Gly Val Pro Gly Val Gly Val Pro Gly Gly Gly Val
305                 310                 315                 320

Pro Gly Ala Gly Val Pro Gly Gly Val Pro Gly Val Gly Val Pro
            325                 330                 335

Gly Val Gly Val Pro Gly Gly Val Pro Gly Ala Gly Val Pro Gly
            340                 345                 350

Val Gly Val Pro Gly Val Gly Val Pro Gly Val Gly Val Pro Gly Gly
            355                 360                 365

Gly Val Pro Gly Ala Gly Val Pro Gly Gly Val Pro Gly Val Gly
        370                 375                 380

Val Pro Gly Val Gly Val Pro Gly Gly Val Pro Gly Ala Gly Val
385                 390                 395                 400

Pro Gly Val Gly Val Pro Gly Val Gly Val Pro Gly Val Gly Val Pro
                405                 410                 415

Gly Gly Gly Val Pro Gly Ala Gly Val Pro Gly Gly Gly Val Pro Gly
                420                 425                 430

Val Gly Val Pro Gly Val Gly Val Pro Gly Gly Gly Val Pro Gly Ala
            435                 440                 445

Gly Val Pro Gly Val Gly Val Pro Gly Val Gly Val Pro Gly Val Gly
        450                 455                 460

Val Pro Gly Gly Gly Val Pro Gly Ala Gly Val Pro Gly Gly Gly Val
465                 470                 475                 480

Pro Gly Val Gly Val Pro Gly Val Gly Val Pro Gly Gly Gly Val Pro
                485                 490                 495

Gly Ala Gly Val Pro Gly Val Gly Val Pro Gly Val Gly Val Pro Gly
            500                 505                 510

Val Gly Val Pro Gly Gly Gly Val Pro Gly Ala Gly Val Pro Gly Gly
        515                 520                 525

Gly Val Pro Gly Val Gly Val Pro Gly Val Gly Val Pro Gly Gly Gly
    530                 535                 540

Val Pro Gly Ala Gly Val Pro Gly Val Gly Val Pro Gly Val Gly Val
545                 550                 555                 560

Pro Gly Val Gly Val Pro Gly Gly Gly Val Pro Gly Ala Gly Val Pro
                565                 570                 575

Gly Gly Gly Val Pro Gly Val Gly Val Pro Gly Val Gly Val Pro Gly
                580                 585                 590

Gly Gly Val Pro Gly Ala Gly Val Pro Gly Gly Gly Val Pro Gly Val
            595                 600                 605

Gly Val Pro Gly Val Gly Val Pro Gly Gly Gly Val Pro Gly Ala Gly
        610                 615                 620

Val Pro Gly Gly Gly Val Pro Gly Trp Pro
625                 630

<210> SEQ ID NO 15
<211> LENGTH: 636
<212> TYPE: PRT
<213> ORGANISM: Artificial Sequence
<220> FEATURE:
<223> OTHER INFORMATION: MAA-VIP ELP1-120

<400> SEQUENCE: 15

Met Ala Ala His Ser Asp Ala Val Phe Thr Asp Asn Tyr Thr Arg Leu
1               5                   10                  15

Arg Lys Gln Met Ala Val Lys Lys Tyr Leu Asn Ser Ile Leu Asn Val
            20                  25                  30

-continued

```
Pro Gly Val Gly Val Pro Gly Val Gly Val Pro Gly Gly Val Pro
         35                  40                  45
Gly Ala Gly Val Pro Gly Val Gly Val Pro Gly Val Gly Val Pro Gly
         50                  55                  60
Val Gly Val Pro Gly Gly Gly Val Pro Gly Ala Gly Val Pro Gly Gly
 65                  70                  75                  80
Gly Val Pro Gly Val Gly Val Pro Gly Val Gly Val Pro Gly Gly Gly
                 85                  90                  95
Val Pro Gly Ala Gly Val Pro Gly Val Gly Val Pro Gly Val Gly Val
                100                 105                 110
Pro Gly Val Gly Val Pro Gly Gly Val Pro Gly Ala Gly Val Pro
                115                 120                 125
Gly Gly Gly Val Pro Gly Val Gly Val Pro Gly Val Gly Val Pro Gly
                130                 135                 140
Gly Gly Val Pro Gly Ala Gly Val Pro Gly Val Gly Val Pro Gly Val
145                 150                 155                 160
Gly Val Pro Gly Val Gly Val Pro Gly Gly Gly Val Pro Gly Ala Gly
                165                 170                 175
Val Pro Gly Gly Gly Val Pro Gly Val Gly Val Pro Gly Val Gly Val
                180                 185                 190
Pro Gly Gly Gly Val Pro Gly Ala Gly Val Pro Gly Val Gly Val Pro
                195                 200                 205
Gly Val Gly Val Pro Gly Val Gly Val Pro Gly Gly Val Pro Gly
                210                 215                 220
Ala Gly Val Pro Gly Gly Gly Val Pro Gly Val Gly Val Pro Gly Val
225                 230                 235                 240
Gly Val Pro Gly Gly Gly Val Pro Gly Ala Gly Val Pro Gly Val Gly
                245                 250                 255
Val Pro Gly Val Gly Val Pro Gly Val Gly Val Pro Gly Gly Gly Val
                260                 265                 270
Pro Gly Ala Gly Val Pro Gly Gly Gly Val Pro Gly Val Gly Val Pro
                275                 280                 285
Gly Val Gly Val Pro Gly Gly Gly Val Pro Gly Ala Gly Val Pro Gly
                290                 295                 300
Val Gly Val Pro Gly Val Gly Val Pro Gly Val Gly Val Pro Gly Gly
305                 310                 315                 320
Gly Val Pro Gly Ala Gly Val Pro Gly Gly Gly Val Pro Gly Val Gly
                325                 330                 335
Val Pro Gly Val Gly Val Pro Gly Gly Gly Val Pro Gly Ala Gly Val
                340                 345                 350
Pro Gly Val Gly Val Pro Gly Val Gly Val Pro Gly Val Gly Val Pro
                355                 360                 365
Gly Gly Gly Val Pro Gly Ala Gly Val Pro Gly Gly Gly Val Pro Gly
                370                 375                 380
Val Gly Val Pro Gly Val Gly Val Pro Gly Gly Gly Val Pro Gly Ala
385                 390                 395                 400
Gly Val Pro Gly Val Gly Val Pro Gly Val Gly Val Pro Gly Val Gly
                405                 410                 415
Val Pro Gly Gly Gly Val Pro Gly Ala Gly Val Pro Gly Gly Gly Val
                420                 425                 430
Pro Gly Val Gly Val Pro Gly Val Gly Val Pro Gly Gly Gly Val Pro
                435                 440                 445
Gly Ala Gly Val Pro Gly Val Gly Val Pro Gly Val Gly Val Pro Gly
```

Val Gly Val Pro Gly Gly Val Pro Gly Ala Gly Val Pro Gly Gly
465                 470                 475                 480

Gly Val Pro Gly Val Gly Val Pro Gly Val Gly Val Pro Gly Gly Gly
                485                 490                 495

Val Pro Gly Ala Gly Val Pro Gly Val Gly Val Pro Gly Val Gly Val
                500                 505                 510

Pro Gly Val Gly Val Pro Gly Gly Gly Val Pro Gly Ala Gly Val Pro
            515                 520                 525

Gly Gly Gly Val Pro Gly Val Gly Val Pro Gly Val Gly Val Pro Gly
        530                 535                 540

Gly Gly Val Pro Gly Ala Gly Val Pro Gly Val Gly Val Pro Gly Val
545                 550                 555                 560

Gly Val Pro Gly Val Gly Val Pro Gly Gly Gly Val Pro Gly Ala Gly
                565                 570                 575

Val Pro Gly Gly Gly Val Pro Gly Val Gly Val Pro Gly Val Gly Val
                580                 585                 590

Pro Gly Gly Gly Val Pro Gly Ala Gly Val Pro Gly Val Gly Val Pro
            595                 600                 605

Gly Val Gly Val Pro Gly Val Gly Val Pro Gly Gly Gly Val Pro Gly
        610                 615                 620

Ala Gly Val Pro Gly Gly Gly Val Pro Gly Trp Pro
625                 630                 635

<210> SEQ ID NO 16
<211> LENGTH: 60
<212> TYPE: DNA
<213> ORGANISM: Artificial Sequence
<220> FEATURE:
<223> OTHER INFORMATION: Primer P0045

<400> SEQUENCE: 16
aattctctag aataatttt gtttaacttt aagaaggaga tatacatatg cactctgacg    60

<210> SEQ ID NO 17
<211> LENGTH: 76
<212> TYPE: DNA
<213> ORGANISM: Artificial Sequence
<220> FEATURE:
<223> OTHER INFORMATION: Primer P0048

<400> SEQUENCE: 17
gtagttgtca gtgaaaacag cgtcagagtg catatgtata tctccttctt aaagttaaac    60
aaaattattt ctagag                                                   76

<210> SEQ ID NO 18
<211> LENGTH: 54
<212> TYPE: DNA
<213> ORGANISM: Artificial Sequence
<220> FEATURE:
<223> OTHER INFORMATION: Primer P0065

<400> SEQUENCE: 18
gttcaggata gagttcaggt acttttttaac agccatctgt ttacgcagac gagt         54

<210> SEQ ID NO 19
<211> LENGTH: 60
<212> TYPE: DNA
<213> ORGANISM: Artificial Sequence
<220> FEATURE:

<223> OTHER INFORMATION: Primer P0066

<400> SEQUENCE: 19
ctagaaataa ttttgtttaa ctttaagaag gagatataca tatggcggcc cactctgacg    60

<210> SEQ ID NO 20
<211> LENGTH: 78
<212> TYPE: DNA
<213> ORGANISM: Artificial Sequence
<220> FEATURE:
<223> OTHER INFORMATION: Primer P0064

<400> SEQUENCE: 20
ctgttttcac tgacaactac actcgtctgc gtaaacagat ggctgttaaa aagtacctga    60
actctatcct gaacgtac                                                  78

<210> SEQ ID NO 21
<211> LENGTH: 76
<212> TYPE: DNA
<213> ORGANISM: Artificial Sequence
<220> FEATURE:
<223> OTHER INFORMATION: Primer P0067

<400> SEQUENCE: 21
gtagttgtca gtgaaaacag cgtcagagtg ggccgccata tgtatatctc cttcttaaag    60
ttaaacaaaa ttattt                                                    76

<210> SEQ ID NO 22
<211> LENGTH: 28
<212> TYPE: PRT
<213> ORGANISM: Homo sapiens

<400> SEQUENCE: 22

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 23
<211> LENGTH: 50
<212> TYPE: PRT
<213> ORGANISM: Artificial Sequence
<220> FEATURE:
<223> OTHER INFORMATION: M-VIP-ELP1-120

<400> SEQUENCE: 23

Met His Ser Asp Ala Val Phe Thr Asp Asn Tyr Thr Arg Leu Arg Lys
1               5                   10                  15

Gln Met Ala Val Lys Lys Tyr Leu Asn Ser Ile Leu Asn Val Pro Gly
            20                  25                  30

Val Gly Val Pro Gly Val Gly Val Pro Gly Gly Val Pro Gly Ala
        35                  40                  45

Gly Val
    50

<210> SEQ ID NO 24
<211> LENGTH: 50
<212> TYPE: PRT
<213> ORGANISM: Artificial Sequence
<220> FEATURE:
<223> OTHER INFORMATION: MAA-VIP-ELP1-120

<400> SEQUENCE: 24

Met Ala Ala His Ser Asp Ala Val Phe Thr Asp Asn Tyr Thr Arg Leu
1               5                   10                  15

Arg Lys Gln Met Ala Val Lys Lys Tyr Leu Asn Ser Ile Leu Asn Val
            20                  25                  30

Pro Gly Val Gly Val Pro Gly Val Gly Val Pro Gly Gly Gly Val Pro
        35                  40                  45

Gly Ala
    50

<210> SEQ ID NO 25
<211> LENGTH: 240
<212> TYPE: DNA
<213> ORGANISM: Artificial Sequence
<220> FEATURE:
<223> OTHER INFORMATION: pPB1046-mVIP-ELP 1-120 fusion sequence

<400> SEQUENCE: 25
taatacgact cactataggg gaattgtgag cggataacaa ttcccctcta gaaataattt      60
tgtttaactt taagaaggag atatacatat gcactctgac gctgttttca ctgacaacta     120
cactcgtctg cgtaaacaga tggctgttaa aaagtacctg aactctatcc tgaacgtacc     180
gggcgtgggt gttccgggcg tgggtgttcc gggtggcggt gtgccgggcg caggtgttcc     240

<210> SEQ ID NO 26
<211> LENGTH: 240
<212> TYPE: DNA
<213> ORGANISM: Artificial Sequence
<220> FEATURE:
<223> OTHER INFORMATION: pPB1047 mVIP-ELP 1-120 fusion sequence

<400> SEQUENCE: 26
taatacgact cactataggg gaattgtgag cggataacaa ttcccctcta gaaataattt      60
tgtttaactt taagaaggag atatacatat ggcggcccac tctgacgctg ttttcactga     120
caactacact cgtctgcgta aacagatggc tgttaaaaag tacctgaact ctatcctgaa     180
cgtaccgggc gtgggtgttc cgggcgtggg tgttccgggt ggcggtgtgc cgggcgcagg     240

<210> SEQ ID NO 27
<211> LENGTH: 10000
<212> TYPE: PRT
<213> ORGANISM: Artificial Sequence
<220> FEATURE:
<223> OTHER INFORMATION: Bioelastic polymer
<220> FEATURE:
<221> NAME/KEY: MISC_FEATURE
<222> LOCATION: (1)..(10000)
<223> OTHER INFORMATION: Xaa may be any natural or non-natural amino
      acid residue
<220> FEATURE:
<221> NAME/KEY: REPEAT
<222> LOCATION: (1)..(10000)
<223> OTHER INFORMATION: Val Pro Gly Xaa Gly sequence may be repeated
      from 20 to 2000 times

<400> SEQUENCE: 27

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa

```
                    50                  55                  60
Gly Val Pro Gly Xaa Gly Val Pro Gly Xaa Gly Val Pro Gly Xaa Gly
 65                  70                  75                  80

Val Pro Gly Xaa Gly Val Pro Gly Xaa Gly Val Pro Gly Xaa Gly Val
                 85                  90                  95

Pro Gly Xaa Gly Val Pro Gly Xaa Gly Val Pro Gly Xaa Gly Val Pro
                100                 105                 110

Gly Xaa Gly Val Pro Gly Xaa Gly Val Pro Gly Xaa Gly Val Pro Gly
            115                 120                 125

Xaa Gly Val Pro Gly Xaa Gly Val Pro Gly Xaa Gly Val Pro Gly Xaa
    130                 135                 140

Gly Val Pro Gly Xaa Gly Val Pro Gly Xaa Gly Val Pro Gly Xaa Gly
145                 150                 155                 160

Val Pro Gly Xaa Gly Val Pro Gly Xaa Gly Val Pro Gly Xaa Gly Val
                165                 170                 175

Pro Gly Xaa Gly Val Pro Gly Xaa Gly Val Pro Gly Xaa Gly Val Pro
                180                 185                 190

Gly Xaa Gly Val Pro Gly Xaa Gly Val Pro Gly Xaa Gly Val Pro Gly
            195                 200                 205

Xaa Gly Val Pro Gly Xaa Gly Val Pro Gly Xaa Gly Val Pro Gly Xaa
    210                 215                 220

Gly Val Pro Gly Xaa Gly Val Pro Gly Xaa Gly Val Pro Gly Xaa Gly
225                 230                 235                 240

Val Pro Gly Xaa Gly Val Pro Gly Xaa Gly Val Pro Gly Xaa Gly Val
                245                 250                 255

Pro Gly Xaa Gly Val Pro Gly Xaa Gly Val Pro Gly Xaa Gly Val Pro
                260                 265                 270

Gly Xaa Gly Val Pro Gly Xaa Gly Val Pro Gly Xaa Gly Val Pro Gly
            275                 280                 285

Xaa Gly Val Pro Gly Xaa Gly Val Pro Gly Xaa Gly Val Pro Gly Xaa
    290                 295                 300

Gly Val Pro Gly Xaa Gly Val Pro Gly Xaa Gly Val Pro Gly Xaa Gly
305                 310                 315                 320

Val Pro Gly Xaa Gly Val Pro Gly Xaa Gly Val Pro Gly Xaa Gly Val
                325                 330                 335

Pro Gly Xaa Gly Val Pro Gly Xaa Gly Val Pro Gly Xaa Gly Val Pro
                340                 345                 350

Gly Xaa Gly Val Pro Gly Xaa Gly Val Pro Gly Xaa Gly Val Pro Gly
            355                 360                 365

Xaa Gly Val Pro Gly Xaa Gly Val Pro Gly Xaa Gly Val Pro Gly Xaa
    370                 375                 380

Gly Val Pro Gly Xaa Gly Val Pro Gly Xaa Gly Val Pro Gly Xaa Gly
385                 390                 395                 400

Val Pro Gly Xaa Gly Val Pro Gly Xaa Gly Val Pro Gly Xaa Gly Val
                405                 410                 415

Pro Gly Xaa Gly Val Pro Gly Xaa Gly Val Pro Gly Xaa Gly Val Pro
                420                 425                 430

Gly Xaa Gly Val Pro Gly Xaa Gly Val Pro Gly Xaa Gly Val Pro Gly
            435                 440                 445

Xaa Gly Val Pro Gly Xaa Gly Val Pro Gly Xaa Gly Val Pro Gly Xaa
    450                 455                 460

Gly Val Pro Gly Xaa Gly Val Pro Gly Xaa Gly Val Pro Gly Xaa Gly
465                 470                 475                 480
```

```
Val Pro Gly Xaa Gly Val Pro Gly Xaa Gly Val Pro Gly Xaa Gly Val
            485                 490                 495

Pro Gly Xaa Gly Val Pro Gly Xaa Gly Val Pro Gly Xaa Gly Val Pro
        500                 505                 510

Gly Xaa Gly Val Pro Gly Xaa Gly Val Pro Gly Xaa Gly Val Pro Gly
    515                 520                 525

Xaa Gly Val Pro Gly Xaa Gly Val Pro Gly Xaa Gly Val Pro Gly Xaa
530                 535                 540

Gly Val Pro Gly Xaa Gly Val Pro Gly Xaa Gly Val Pro Gly Xaa Gly
545                 550                 555                 560

Val Pro Gly Xaa Gly Val Pro Gly Xaa Gly Val Pro Gly Xaa Gly Val
            565                 570                 575

Pro Gly Xaa Gly Val Pro Gly Xaa Gly Val Pro Gly Xaa Gly Val Pro
        580                 585                 590

Gly Xaa Gly Val Pro Gly Xaa Gly Val Pro Gly Xaa Gly Val Pro Gly
    595                 600                 605

Xaa Gly Val Pro Gly Xaa Gly Val Pro Gly Xaa Gly Val Pro Gly Xaa
610                 615                 620

Gly Val Pro Gly Xaa Gly Val Pro Gly Xaa Gly Val Pro Gly Xaa Gly
625                 630                 635                 640

Val Pro Gly Xaa Gly Val Pro Gly Xaa Gly Val Pro Gly Xaa Gly Val
            645                 650                 655

Pro Gly Xaa Gly Val Pro Gly Xaa Gly Val Pro Gly Xaa Gly Val Pro
        660                 665                 670

Gly Xaa Gly Val Pro Gly Xaa Gly Val Pro Gly Xaa Gly Val Pro Gly
    675                 680                 685

Xaa Gly Val Pro Gly Xaa Gly Val Pro Gly Xaa Gly Val Pro Gly Xaa
690                 695                 700

Gly Val Pro Gly Xaa Gly Val Pro Gly Xaa Gly Val Pro Gly Xaa Gly
705                 710                 715                 720

Val Pro Gly Xaa Gly Val Pro Gly Xaa Gly Val Pro Gly Xaa Gly Val
            725                 730                 735

Pro Gly Xaa Gly Val Pro Gly Xaa Gly Val Pro Gly Xaa Gly Val Pro
        740                 745                 750

Gly Xaa Gly Val Pro Gly Xaa Gly Val Pro Gly Xaa Gly Val Pro Gly
    755                 760                 765

Xaa Gly Val Pro Gly Xaa Gly Val Pro Gly Xaa Gly Val Pro Gly Xaa
770                 775                 780

Gly Val Pro Gly Xaa Gly Val Pro Gly Xaa Gly Val Pro Gly Xaa Gly
785                 790                 795                 800

Val Pro Gly Xaa Gly Val Pro Gly Xaa Gly Val Pro Gly Xaa Gly Val
            805                 810                 815

Pro Gly Xaa Gly Val Pro Gly Xaa Gly Val Pro Gly Xaa Gly Val Pro
        820                 825                 830

Gly Xaa Gly Val Pro Gly Xaa Gly Val Pro Gly Xaa Gly Val Pro Gly
    835                 840                 845

Xaa Gly Val Pro Gly Xaa Gly Val Pro Gly Xaa Gly Val Pro Gly Xaa
850                 855                 860

Gly Val Pro Gly Xaa Gly Val Pro Gly Xaa Gly Val Pro Gly Xaa Gly
865                 870                 875                 880

Val Pro Gly Xaa Gly Val Pro Gly Xaa Gly Val Pro Gly Xaa Gly Val
            885                 890                 895
```

-continued

Pro Gly Xaa Gly Val Pro Gly Xaa Gly Val Pro Gly Xaa Gly Val Pro
            900                 905                 910

Gly Xaa Gly Val Pro Gly Xaa Gly Val Pro Gly Xaa Gly Val Pro Gly
        915                 920                 925

Xaa Gly Val Pro Gly Xaa Gly Val Pro Gly Xaa Gly Val Pro Gly Xaa
    930                 935                 940

Gly Val Pro Gly Xaa Gly Val Pro Gly Xaa Gly Val Pro Gly Xaa Gly
945                 950                 955                 960

Val Pro Gly Xaa Gly Val Pro Gly Xaa Gly Val Pro Gly Xaa Gly Val
                965                 970                 975

Pro Gly Xaa Gly Val Pro Gly Xaa Gly Val Pro Gly Xaa Gly Val Pro
            980                 985                 990

Gly Xaa Gly Val Pro Gly Xaa Gly Val Pro Gly Xaa Gly Val Pro Gly
        995                 1000                1005

Xaa Gly Val Pro Gly Xaa Gly Val Pro Gly Xaa Gly Val Pro Gly
    1010                1015                1020

Xaa Gly Val Pro Gly Xaa Gly Val Pro Gly Xaa Gly Val Pro Gly
    1025                1030                1035

Xaa Gly Val Pro Gly Xaa Gly Val Pro Gly Xaa Gly Val Pro Gly
    1040                1045                1050

Xaa Gly Val Pro Gly Xaa Gly Val Pro Gly Xaa Gly Val Pro Gly
    1055                1060                1065

Xaa Gly Val Pro Gly Xaa Gly Val Pro Gly Xaa Gly Val Pro Gly
    1070                1075                1080

Xaa Gly Val Pro Gly Xaa Gly Val Pro Gly Xaa Gly Val Pro Gly
    1085                1090                1095

Xaa Gly Val Pro Gly Xaa Gly Val Pro Gly Xaa Gly Val Pro Gly
    1100                1105                1110

Xaa Gly Val Pro Gly Xaa Gly Val Pro Gly Xaa Gly Val Pro Gly
    1115                1120                1125

Xaa Gly Val Pro Gly Xaa Gly Val Pro Gly Xaa Gly Val Pro Gly
    1130                1135                1140

Xaa Gly Val Pro Gly Xaa Gly Val Pro Gly Xaa Gly Val Pro Gly
    1145                1150                1155

Xaa Gly Val Pro Gly Xaa Gly Val Pro Gly Xaa Gly Val Pro Gly
    1160                1165                1170

Xaa Gly Val Pro Gly Xaa Gly Val Pro Gly Xaa Gly Val Pro Gly
    1175                1180                1185

Xaa Gly Val Pro Gly Xaa Gly Val Pro Gly Xaa Gly Val Pro Gly
    1190                1195                1200

Xaa Gly Val Pro Gly Xaa Gly Val Pro Gly Xaa Gly Val Pro Gly
    1205                1210                1215

Xaa Gly Val Pro Gly Xaa Gly Val Pro Gly Xaa Gly Val Pro Gly
    1220                1225                1230

Xaa Gly Val Pro Gly Xaa Gly Val Pro Gly Xaa Gly Val Pro Gly
    1235                1240                1245

Xaa Gly Val Pro Gly Xaa Gly Val Pro Gly Xaa Gly Val Pro Gly
    1250                1255                1260

Xaa Gly Val Pro Gly Xaa Gly Val Pro Gly Xaa Gly Val Pro Gly
    1265                1270                1275

Xaa Gly Val Pro Gly Xaa Gly Val Pro Gly Xaa Gly Val Pro Gly
    1280                1285                1290

Xaa Gly Val Pro Gly Xaa Gly Val Pro Gly Xaa Gly Val Pro Gly

-continued

```
            1295                1300                1305

Xaa Gly Val Pro Gly Xaa Gly Val Pro Gly Xaa Gly Val Pro Gly
    1310                1315                1320

Xaa Gly Val Pro Gly Xaa Gly Val Pro Gly Xaa Gly Val Pro Gly
    1325                1330                1335

Xaa Gly Val Pro Gly Xaa Gly Val Pro Gly Xaa Gly Val Pro Gly
    1340                1345                1350

Xaa Gly Val Pro Gly Xaa Gly Val Pro Gly Xaa Gly Val Pro Gly
    1355                1360                1365

Xaa Gly Val Pro Gly Xaa Gly Val Pro Gly Xaa Gly Val Pro Gly
    1370                1375                1380

Xaa Gly Val Pro Gly Xaa Gly Val Pro Gly Xaa Gly Val Pro Gly
    1385                1390                1395

Xaa Gly Val Pro Gly Xaa Gly Val Pro Gly Xaa Gly Val Pro Gly
    1400                1405                1410

Xaa Gly Val Pro Gly Xaa Gly Val Pro Gly Xaa Gly Val Pro Gly
    1415                1420                1425

Xaa Gly Val Pro Gly Xaa Gly Val Pro Gly Xaa Gly Val Pro Gly
    1430                1435                1440

Xaa Gly Val Pro Gly Xaa Gly Val Pro Gly Xaa Gly Val Pro Gly
    1445                1450                1455

Xaa Gly Val Pro Gly Xaa Gly Val Pro Gly Xaa Gly Val Pro Gly
    1460                1465                1470

Xaa Gly Val Pro Gly Xaa Gly Val Pro Gly Xaa Gly Val Pro Gly
    1475                1480                1485

Xaa Gly Val Pro Gly Xaa Gly Val Pro Gly Xaa Gly Val Pro Gly
    1490                1495                1500

Xaa Gly Val Pro Gly Xaa Gly Val Pro Gly Xaa Gly Val Pro Gly
    1505                1510                1515

Xaa Gly Val Pro Gly Xaa Gly Val Pro Gly Xaa Gly Val Pro Gly
    1520                1525                1530

Xaa Gly Val Pro Gly Xaa Gly Val Pro Gly Xaa Gly Val Pro Gly
    1535                1540                1545

Xaa Gly Val Pro Gly Xaa Gly Val Pro Gly Xaa Gly Val Pro Gly
    1550                1555                1560

Xaa Gly Val Pro Gly Xaa Gly Val Pro Gly Xaa Gly Val Pro Gly
    1565                1570                1575

Xaa Gly Val Pro Gly Xaa Gly Val Pro Gly Xaa Gly Val Pro Gly
    1580                1585                1590

Xaa Gly Val Pro Gly Xaa Gly Val Pro Gly Xaa Gly Val Pro Gly
    1595                1600                1605

Xaa Gly Val Pro Gly Xaa Gly Val Pro Gly Xaa Gly Val Pro Gly
    1610                1615                1620

Xaa Gly Val Pro Gly Xaa Gly Val Pro Gly Xaa Gly Val Pro Gly
    1625                1630                1635

Xaa Gly Val Pro Gly Xaa Gly Val Pro Gly Xaa Gly Val Pro Gly
    1640                1645                1650

Xaa Gly Val Pro Gly Xaa Gly Val Pro Gly Xaa Gly Val Pro Gly
    1655                1660                1665

Xaa Gly Val Pro Gly Xaa Gly Val Pro Gly Xaa Gly Val Pro Gly
    1670                1675                1680

Xaa Gly Val Pro Gly Xaa Gly Val Pro Gly Xaa Gly Val Pro Gly
    1685                1690                1695
```

```
Xaa Gly Val Pro Gly Xaa Gly Val Pro Gly Xaa Gly Val Pro Gly
    1700                1705                1710

Xaa Gly Val Pro Gly Xaa Gly Val Pro Gly Xaa Gly Val Pro Gly
    1715                1720                1725

Xaa Gly Val Pro Gly Xaa Gly Val Pro Gly Xaa Gly Val Pro Gly
    1730                1735                1740

Xaa Gly Val Pro Gly Xaa Gly Val Pro Gly Xaa Gly Val Pro Gly
    1745                1750                1755

Xaa Gly Val Pro Gly Xaa Gly Val Pro Gly Xaa Gly Val Pro Gly
    1760                1765                1770

Xaa Gly Val Pro Gly Xaa Gly Val Pro Gly Xaa Gly Val Pro Gly
    1775                1780                1785

Xaa Gly Val Pro Gly Xaa Gly Val Pro Gly Xaa Gly Val Pro Gly
    1790                1795                1800

Xaa Gly Val Pro Gly Xaa Gly Val Pro Gly Xaa Gly Val Pro Gly
    1805                1810                1815

Xaa Gly Val Pro Gly Xaa Gly Val Pro Gly Xaa Gly Val Pro Gly
    1820                1825                1830

Xaa Gly Val Pro Gly Xaa Gly Val Pro Gly Xaa Gly Val Pro Gly
    1835                1840                1845

Xaa Gly Val Pro Gly Xaa Gly Val Pro Gly Xaa Gly Val Pro Gly
    1850                1855                1860

Xaa Gly Val Pro Gly Xaa Gly Val Pro Gly Xaa Gly Val Pro Gly
    1865                1870                1875

Xaa Gly Val Pro Gly Xaa Gly Val Pro Gly Xaa Gly Val Pro Gly
    1880                1885                1890

Xaa Gly Val Pro Gly Xaa Gly Val Pro Gly Xaa Gly Val Pro Gly
    1895                1900                1905

Xaa Gly Val Pro Gly Xaa Gly Val Pro Gly Xaa Gly Val Pro Gly
    1910                1915                1920

Xaa Gly Val Pro Gly Xaa Gly Val Pro Gly Xaa Gly Val Pro Gly
    1925                1930                1935

Xaa Gly Val Pro Gly Xaa Gly Val Pro Gly Xaa Gly Val Pro Gly
    1940                1945                1950

Xaa Gly Val Pro Gly Xaa Gly Val Pro Gly Xaa Gly Val Pro Gly
    1955                1960                1965

Xaa Gly Val Pro Gly Xaa Gly Val Pro Gly Xaa Gly Val Pro Gly
    1970                1975                1980

Xaa Gly Val Pro Gly Xaa Gly Val Pro Gly Xaa Gly Val Pro Gly
    1985                1990                1995

Xaa Gly Val Pro Gly Xaa Gly Val Pro Gly Xaa Gly Val Pro Gly
    2000                2005                2010

Xaa Gly Val Pro Gly Xaa Gly Val Pro Gly Xaa Gly Val Pro Gly
    2015                2020                2025

Xaa Gly Val Pro Gly Xaa Gly Val Pro Gly Xaa Gly Val Pro Gly
    2030                2035                2040

Xaa Gly Val Pro Gly Xaa Gly Val Pro Gly Xaa Gly Val Pro Gly
    2045                2050                2055

Xaa Gly Val Pro Gly Xaa Gly Val Pro Gly Xaa Gly Val Pro Gly
    2060                2065                2070

Xaa Gly Val Pro Gly Xaa Gly Val Pro Gly Xaa Gly Val Pro Gly
    2075                2080                2085
```

Xaa Gly Val Pro Gly Xaa Gly Val Pro Gly Xaa Gly Val Pro Gly
    2090                2095                2100

Xaa Gly Val Pro Gly Xaa Gly Val Pro Gly Xaa Gly Val Pro Gly
    2105                2110                2115

Xaa Gly Val Pro Gly Xaa Gly Val Pro Gly Xaa Gly Val Pro Gly
    2120                2125                2130

Xaa Gly Val Pro Gly Xaa Gly Val Pro Gly Xaa Gly Val Pro Gly
    2135                2140                2145

Xaa Gly Val Pro Gly Xaa Gly Val Pro Gly Xaa Gly Val Pro Gly
    2150                2155                2160

Xaa Gly Val Pro Gly Xaa Gly Val Pro Gly Xaa Gly Val Pro Gly
    2165                2170                2175

Xaa Gly Val Pro Gly Xaa Gly Val Pro Gly Xaa Gly Val Pro Gly
    2180                2185                2190

Xaa Gly Val Pro Gly Xaa Gly Val Pro Gly Xaa Gly Val Pro Gly
    2195                2200                2205

Xaa Gly Val Pro Gly Xaa Gly Val Pro Gly Xaa Gly Val Pro Gly
    2210                2215                2220

Xaa Gly Val Pro Gly Xaa Gly Val Pro Gly Xaa Gly Val Pro Gly
    2225                2230                2235

Xaa Gly Val Pro Gly Xaa Gly Val Pro Gly Xaa Gly Val Pro Gly
    2240                2245                2250

Xaa Gly Val Pro Gly Xaa Gly Val Pro Gly Xaa Gly Val Pro Gly
    2255                2260                2265

Xaa Gly Val Pro Gly Xaa Gly Val Pro Gly Xaa Gly Val Pro Gly
    2270                2275                2280

Xaa Gly Val Pro Gly Xaa Gly Val Pro Gly Xaa Gly Val Pro Gly
    2285                2290                2295

Xaa Gly Val Pro Gly Xaa Gly Val Pro Gly Xaa Gly Val Pro Gly
    2300                2305                2310

Xaa Gly Val Pro Gly Xaa Gly Val Pro Gly Xaa Gly Val Pro Gly
    2315                2320                2325

Xaa Gly Val Pro Gly Xaa Gly Val Pro Gly Xaa Gly Val Pro Gly
    2330                2335                2340

Xaa Gly Val Pro Gly Xaa Gly Val Pro Gly Xaa Gly Val Pro Gly
    2345                2350                2355

Xaa Gly Val Pro Gly Xaa Gly Val Pro Gly Xaa Gly Val Pro Gly
    2360                2365                2370

Xaa Gly Val Pro Gly Xaa Gly Val Pro Gly Xaa Gly Val Pro Gly
    2375                2380                2385

Xaa Gly Val Pro Gly Xaa Gly Val Pro Gly Xaa Gly Val Pro Gly
    2390                2395                2400

Xaa Gly Val Pro Gly Xaa Gly Val Pro Gly Xaa Gly Val Pro Gly
    2405                2410                2415

Xaa Gly Val Pro Gly Xaa Gly Val Pro Gly Xaa Gly Val Pro Gly
    2420                2425                2430

Xaa Gly Val Pro Gly Xaa Gly Val Pro Gly Xaa Gly Val Pro Gly
    2435                2440                2445

Xaa Gly Val Pro Gly Xaa Gly Val Pro Gly Xaa Gly Val Pro Gly
    2450                2455                2460

Xaa Gly Val Pro Gly Xaa Gly Val Pro Gly Xaa Gly Val Pro Gly
    2465                2470                2475

Xaa Gly Val Pro Gly Xaa Gly Val Pro Gly Xaa Gly Val Pro Gly

-continued

```
                2480                2485                2490

Xaa Gly Val Pro Gly Xaa Gly Val Pro Gly Xaa Gly Val Pro Gly
    2495                2500                2505

Xaa Gly Val Pro Gly Xaa Gly Val Pro Gly Xaa Gly Val Pro Gly
    2510                2515                2520

Xaa Gly Val Pro Gly Xaa Gly Val Pro Gly Xaa Gly Val Pro Gly
    2525                2530                2535

Xaa Gly Val Pro Gly Xaa Gly Val Pro Gly Xaa Gly Val Pro Gly
    2540                2545                2550

Xaa Gly Val Pro Gly Xaa Gly Val Pro Gly Xaa Gly Val Pro Gly
    2555                2560                2565

Xaa Gly Val Pro Gly Xaa Gly Val Pro Gly Xaa Gly Val Pro Gly
    2570                2575                2580

Xaa Gly Val Pro Gly Xaa Gly Val Pro Gly Xaa Gly Val Pro Gly
    2585                2590                2595

Xaa Gly Val Pro Gly Xaa Gly Val Pro Gly Xaa Gly Val Pro Gly
    2600                2605                2610

Xaa Gly Val Pro Gly Xaa Gly Val Pro Gly Xaa Gly Val Pro Gly
    2615                2620                2625

Xaa Gly Val Pro Gly Xaa Gly Val Pro Gly Xaa Gly Val Pro Gly
    2630                2635                2640

Xaa Gly Val Pro Gly Xaa Gly Val Pro Gly Xaa Gly Val Pro Gly
    2645                2650                2655

Xaa Gly Val Pro Gly Xaa Gly Val Pro Gly Xaa Gly Val Pro Gly
    2660                2665                2670

Xaa Gly Val Pro Gly Xaa Gly Val Pro Gly Xaa Gly Val Pro Gly
    2675                2680                2685

Xaa Gly Val Pro Gly Xaa Gly Val Pro Gly Xaa Gly Val Pro Gly
    2690                2695                2700

Xaa Gly Val Pro Gly Xaa Gly Val Pro Gly Xaa Gly Val Pro Gly
    2705                2710                2715

Xaa Gly Val Pro Gly Xaa Gly Val Pro Gly Xaa Gly Val Pro Gly
    2720                2725                2730

Xaa Gly Val Pro Gly Xaa Gly Val Pro Gly Xaa Gly Val Pro Gly
    2735                2740                2745

Xaa Gly Val Pro Gly Xaa Gly Val Pro Gly Xaa Gly Val Pro Gly
    2750                2755                2760

Xaa Gly Val Pro Gly Xaa Gly Val Pro Gly Xaa Gly Val Pro Gly
    2765                2770                2775

Xaa Gly Val Pro Gly Xaa Gly Val Pro Gly Xaa Gly Val Pro Gly
    2780                2785                2790

Xaa Gly Val Pro Gly Xaa Gly Val Pro Gly Xaa Gly Val Pro Gly
    2795                2800                2805

Xaa Gly Val Pro Gly Xaa Gly Val Pro Gly Xaa Gly Val Pro Gly
    2810                2815                2820

Xaa Gly Val Pro Gly Xaa Gly Val Pro Gly Xaa Gly Val Pro Gly
    2825                2830                2835

Xaa Gly Val Pro Gly Xaa Gly Val Pro Gly Xaa Gly Val Pro Gly
    2840                2845                2850

Xaa Gly Val Pro Gly Xaa Gly Val Pro Gly Xaa Gly Val Pro Gly
    2855                2860                2865

Xaa Gly Val Pro Gly Xaa Gly Val Pro Gly Xaa Gly Val Pro Gly
    2870                2875                2880
```

Xaa Gly Val Pro Gly Xaa Gly Val Pro Gly Xaa Gly Val Pro Gly
    2885                2890                2895

Xaa Gly Val Pro Gly Xaa Gly Val Pro Gly Xaa Gly Val Pro Gly
    2900                2905                2910

Xaa Gly Val Pro Gly Xaa Gly Val Pro Gly Xaa Gly Val Pro Gly
    2915                2920                2925

Xaa Gly Val Pro Gly Xaa Gly Val Pro Gly Xaa Gly Val Pro Gly
    2930                2935                2940

Xaa Gly Val Pro Gly Xaa Gly Val Pro Gly Xaa Gly Val Pro Gly
    2945                2950                2955

Xaa Gly Val Pro Gly Xaa Gly Val Pro Gly Xaa Gly Val Pro Gly
    2960                2965                2970

Xaa Gly Val Pro Gly Xaa Gly Val Pro Gly Xaa Gly Val Pro Gly
    2975                2980                2985

Xaa Gly Val Pro Gly Xaa Gly Val Pro Gly Xaa Gly Val Pro Gly
    2990                2995                3000

Xaa Gly Val Pro Gly Xaa Gly Val Pro Gly Xaa Gly Val Pro Gly
    3005                3010                3015

Xaa Gly Val Pro Gly Xaa Gly Val Pro Gly Xaa Gly Val Pro Gly
    3020                3025                3030

Xaa Gly Val Pro Gly Xaa Gly Val Pro Gly Xaa Gly Val Pro Gly
    3035                3040                3045

Xaa Gly Val Pro Gly Xaa Gly Val Pro Gly Xaa Gly Val Pro Gly
    3050                3055                3060

Xaa Gly Val Pro Gly Xaa Gly Val Pro Gly Xaa Gly Val Pro Gly
    3065                3070                3075

Xaa Gly Val Pro Gly Xaa Gly Val Pro Gly Xaa Gly Val Pro Gly
    3080                3085                3090

Xaa Gly Val Pro Gly Xaa Gly Val Pro Gly Xaa Gly Val Pro Gly
    3095                3100                3105

Xaa Gly Val Pro Gly Xaa Gly Val Pro Gly Xaa Gly Val Pro Gly
    3110                3115                3120

Xaa Gly Val Pro Gly Xaa Gly Val Pro Gly Xaa Gly Val Pro Gly
    3125                3130                3135

Xaa Gly Val Pro Gly Xaa Gly Val Pro Gly Xaa Gly Val Pro Gly
    3140                3145                3150

Xaa Gly Val Pro Gly Xaa Gly Val Pro Gly Xaa Gly Val Pro Gly
    3155                3160                3165

Xaa Gly Val Pro Gly Xaa Gly Val Pro Gly Xaa Gly Val Pro Gly
    3170                3175                3180

Xaa Gly Val Pro Gly Xaa Gly Val Pro Gly Xaa Gly Val Pro Gly
    3185                3190                3195

Xaa Gly Val Pro Gly Xaa Gly Val Pro Gly Xaa Gly Val Pro Gly
    3200                3205                3210

Xaa Gly Val Pro Gly Xaa Gly Val Pro Gly Xaa Gly Val Pro Gly
    3215                3220                3225

Xaa Gly Val Pro Gly Xaa Gly Val Pro Gly Xaa Gly Val Pro Gly
    3230                3235                3240

Xaa Gly Val Pro Gly Xaa Gly Val Pro Gly Xaa Gly Val Pro Gly
    3245                3250                3255

Xaa Gly Val Pro Gly Xaa Gly Val Pro Gly Xaa Gly Val Pro Gly
    3260                3265                3270

-continued

```
Xaa Gly Val Pro Gly Xaa Gly Val Pro Gly Xaa Gly Val Pro Gly
    3275                3280                3285

Xaa Gly Val Pro Gly Xaa Gly Val Pro Gly Xaa Gly Val Pro Gly
    3290                3295                3300

Xaa Gly Val Pro Gly Xaa Gly Val Pro Gly Xaa Gly Val Pro Gly
    3305                3310                3315

Xaa Gly Val Pro Gly Xaa Gly Val Pro Gly Xaa Gly Val Pro Gly
    3320                3325                3330

Xaa Gly Val Pro Gly Xaa Gly Val Pro Gly Xaa Gly Val Pro Gly
    3335                3340                3345

Xaa Gly Val Pro Gly Xaa Gly Val Pro Gly Xaa Gly Val Pro Gly
    3350                3355                3360

Xaa Gly Val Pro Gly Xaa Gly Val Pro Gly Xaa Gly Val Pro Gly
    3365                3370                3375

Xaa Gly Val Pro Gly Xaa Gly Val Pro Gly Xaa Gly Val Pro Gly
    3380                3385                3390

Xaa Gly Val Pro Gly Xaa Gly Val Pro Gly Xaa Gly Val Pro Gly
    3395                3400                3405

Xaa Gly Val Pro Gly Xaa Gly Val Pro Gly Xaa Gly Val Pro Gly
    3410                3415                3420

Xaa Gly Val Pro Gly Xaa Gly Val Pro Gly Xaa Gly Val Pro Gly
    3425                3430                3435

Xaa Gly Val Pro Gly Xaa Gly Val Pro Gly Xaa Gly Val Pro Gly
    3440                3445                3450

Xaa Gly Val Pro Gly Xaa Gly Val Pro Gly Xaa Gly Val Pro Gly
    3455                3460                3465

Xaa Gly Val Pro Gly Xaa Gly Val Pro Gly Xaa Gly Val Pro Gly
    3470                3475                3480

Xaa Gly Val Pro Gly Xaa Gly Val Pro Gly Xaa Gly Val Pro Gly
    3485                3490                3495

Xaa Gly Val Pro Gly Xaa Gly Val Pro Gly Xaa Gly Val Pro Gly
    3500                3505                3510

Xaa Gly Val Pro Gly Xaa Gly Val Pro Gly Xaa Gly Val Pro Gly
    3515                3520                3525

Xaa Gly Val Pro Gly Xaa Gly Val Pro Gly Xaa Gly Val Pro Gly
    3530                3535                3540

Xaa Gly Val Pro Gly Xaa Gly Val Pro Gly Xaa Gly Val Pro Gly
    3545                3550                3555

Xaa Gly Val Pro Gly Xaa Gly Val Pro Gly Xaa Gly Val Pro Gly
    3560                3565                3570

Xaa Gly Val Pro Gly Xaa Gly Val Pro Gly Xaa Gly Val Pro Gly
    3575                3580                3585

Xaa Gly Val Pro Gly Xaa Gly Val Pro Gly Xaa Gly Val Pro Gly
    3590                3595                3600

Xaa Gly Val Pro Gly Xaa Gly Val Pro Gly Xaa Gly Val Pro Gly
    3605                3610                3615

Xaa Gly Val Pro Gly Xaa Gly Val Pro Gly Xaa Gly Val Pro Gly
    3620                3625                3630

Xaa Gly Val Pro Gly Xaa Gly Val Pro Gly Xaa Gly Val Pro Gly
    3635                3640                3645

Xaa Gly Val Pro Gly Xaa Gly Val Pro Gly Xaa Gly Val Pro Gly
    3650                3655                3660

Xaa Gly Val Pro Gly Xaa Gly Val Pro Gly Xaa Gly Val Pro Gly
```

-continued

```
            3665            3670            3675

Xaa Gly Val Pro Gly Xaa Gly Val Pro Gly Xaa Gly Val Pro Gly
    3680            3685            3690

Xaa Gly Val Pro Gly Xaa Gly Val Pro Gly Xaa Gly Val Pro Gly
    3695            3700            3705

Xaa Gly Val Pro Gly Xaa Gly Val Pro Gly Xaa Gly Val Pro Gly
    3710            3715            3720

Xaa Gly Val Pro Gly Xaa Gly Val Pro Gly Xaa Gly Val Pro Gly
    3725            3730            3735

Xaa Gly Val Pro Gly Xaa Gly Val Pro Gly Xaa Gly Val Pro Gly
    3740            3745            3750

Xaa Gly Val Pro Gly Xaa Gly Val Pro Gly Xaa Gly Val Pro Gly
    3755            3760            3765

Xaa Gly Val Pro Gly Xaa Gly Val Pro Gly Xaa Gly Val Pro Gly
    3770            3775            3780

Xaa Gly Val Pro Gly Xaa Gly Val Pro Gly Xaa Gly Val Pro Gly
    3785            3790            3795

Xaa Gly Val Pro Gly Xaa Gly Val Pro Gly Xaa Gly Val Pro Gly
    3800            3805            3810

Xaa Gly Val Pro Gly Xaa Gly Val Pro Gly Xaa Gly Val Pro Gly
    3815            3820            3825

Xaa Gly Val Pro Gly Xaa Gly Val Pro Gly Xaa Gly Val Pro Gly
    3830            3835            3840

Xaa Gly Val Pro Gly Xaa Gly Val Pro Gly Xaa Gly Val Pro Gly
    3845            3850            3855

Xaa Gly Val Pro Gly Xaa Gly Val Pro Gly Xaa Gly Val Pro Gly
    3860            3865            3870

Xaa Gly Val Pro Gly Xaa Gly Val Pro Gly Xaa Gly Val Pro Gly
    3875            3880            3885

Xaa Gly Val Pro Gly Xaa Gly Val Pro Gly Xaa Gly Val Pro Gly
    3890            3895            3900

Xaa Gly Val Pro Gly Xaa Gly Val Pro Gly Xaa Gly Val Pro Gly
    3905            3910            3915

Xaa Gly Val Pro Gly Xaa Gly Val Pro Gly Xaa Gly Val Pro Gly
    3920            3925            3930

Xaa Gly Val Pro Gly Xaa Gly Val Pro Gly Xaa Gly Val Pro Gly
    3935            3940            3945

Xaa Gly Val Pro Gly Xaa Gly Val Pro Gly Xaa Gly Val Pro Gly
    3950            3955            3960

Xaa Gly Val Pro Gly Xaa Gly Val Pro Gly Xaa Gly Val Pro Gly
    3965            3970            3975

Xaa Gly Val Pro Gly Xaa Gly Val Pro Gly Xaa Gly Val Pro Gly
    3980            3985            3990

Xaa Gly Val Pro Gly Xaa Gly Val Pro Gly Xaa Gly Val Pro Gly
    3995            4000            4005

Xaa Gly Val Pro Gly Xaa Gly Val Pro Gly Xaa Gly Val Pro Gly
    4010            4015            4020

Xaa Gly Val Pro Gly Xaa Gly Val Pro Gly Xaa Gly Val Pro Gly
    4025            4030            4035

Xaa Gly Val Pro Gly Xaa Gly Val Pro Gly Xaa Gly Val Pro Gly
    4040            4045            4050

Xaa Gly Val Pro Gly Xaa Gly Val Pro Gly Xaa Gly Val Pro Gly
    4055            4060            4065
```

-continued

Xaa Gly Val Pro Gly Xaa Gly Val Pro Gly Xaa Gly Val Pro Gly
    4070                4075                4080

Xaa Gly Val Pro Gly Xaa Gly Val Pro Gly Xaa Gly Val Pro Gly
    4085                4090                4095

Xaa Gly Val Pro Gly Xaa Gly Val Pro Gly Xaa Gly Val Pro Gly
    4100                4105                4110

Xaa Gly Val Pro Gly Xaa Gly Val Pro Gly Xaa Gly Val Pro Gly
    4115                4120                4125

Xaa Gly Val Pro Gly Xaa Gly Val Pro Gly Xaa Gly Val Pro Gly
    4130                4135                4140

Xaa Gly Val Pro Gly Xaa Gly Val Pro Gly Xaa Gly Val Pro Gly
    4145                4150                4155

Xaa Gly Val Pro Gly Xaa Gly Val Pro Gly Xaa Gly Val Pro Gly
    4160                4165                4170

Xaa Gly Val Pro Gly Xaa Gly Val Pro Gly Xaa Gly Val Pro Gly
    4175                4180                4185

Xaa Gly Val Pro Gly Xaa Gly Val Pro Gly Xaa Gly Val Pro Gly
    4190                4195                4200

Xaa Gly Val Pro Gly Xaa Gly Val Pro Gly Xaa Gly Val Pro Gly
    4205                4210                4215

Xaa Gly Val Pro Gly Xaa Gly Val Pro Gly Xaa Gly Val Pro Gly
    4220                4225                4230

Xaa Gly Val Pro Gly Xaa Gly Val Pro Gly Xaa Gly Val Pro Gly
    4235                4240                4245

Xaa Gly Val Pro Gly Xaa Gly Val Pro Gly Xaa Gly Val Pro Gly
    4250                4255                4260

Xaa Gly Val Pro Gly Xaa Gly Val Pro Gly Xaa Gly Val Pro Gly
    4265                4270                4275

Xaa Gly Val Pro Gly Xaa Gly Val Pro Gly Xaa Gly Val Pro Gly
    4280                4285                4290

Xaa Gly Val Pro Gly Xaa Gly Val Pro Gly Xaa Gly Val Pro Gly
    4295                4300                4305

Xaa Gly Val Pro Gly Xaa Gly Val Pro Gly Xaa Gly Val Pro Gly
    4310                4315                4320

Xaa Gly Val Pro Gly Xaa Gly Val Pro Gly Xaa Gly Val Pro Gly
    4325                4330                4335

Xaa Gly Val Pro Gly Xaa Gly Val Pro Gly Xaa Gly Val Pro Gly
    4340                4345                4350

Xaa Gly Val Pro Gly Xaa Gly Val Pro Gly Xaa Gly Val Pro Gly
    4355                4360                4365

Xaa Gly Val Pro Gly Xaa Gly Val Pro Gly Xaa Gly Val Pro Gly
    4370                4375                4380

Xaa Gly Val Pro Gly Xaa Gly Val Pro Gly Xaa Gly Val Pro Gly
    4385                4390                4395

Xaa Gly Val Pro Gly Xaa Gly Val Pro Gly Xaa Gly Val Pro Gly
    4400                4405                4410

Xaa Gly Val Pro Gly Xaa Gly Val Pro Gly Xaa Gly Val Pro Gly
    4415                4420                4425

Xaa Gly Val Pro Gly Xaa Gly Val Pro Gly Xaa Gly Val Pro Gly
    4430                4435                4440

Xaa Gly Val Pro Gly Xaa Gly Val Pro Gly Xaa Gly Val Pro Gly
    4445                4450                4455

-continued

Xaa Gly Val Pro Gly Xaa Gly Val Pro Gly Xaa Gly Val Pro Gly
    4460                4465                4470

Xaa Gly Val Pro Gly Xaa Gly Val Pro Gly Xaa Gly Val Pro Gly
    4475                4480                4485

Xaa Gly Val Pro Gly Xaa Gly Val Pro Gly Xaa Gly Val Pro Gly
    4490                4495                4500

Xaa Gly Val Pro Gly Xaa Gly Val Pro Gly Xaa Gly Val Pro Gly
    4505                4510                4515

Xaa Gly Val Pro Gly Xaa Gly Val Pro Gly Xaa Gly Val Pro Gly
    4520                4525                4530

Xaa Gly Val Pro Gly Xaa Gly Val Pro Gly Xaa Gly Val Pro Gly
    4535                4540                4545

Xaa Gly Val Pro Gly Xaa Gly Val Pro Gly Xaa Gly Val Pro Gly
    4550                4555                4560

Xaa Gly Val Pro Gly Xaa Gly Val Pro Gly Xaa Gly Val Pro Gly
    4565                4570                4575

Xaa Gly Val Pro Gly Xaa Gly Val Pro Gly Xaa Gly Val Pro Gly
    4580                4585                4590

Xaa Gly Val Pro Gly Xaa Gly Val Pro Gly Xaa Gly Val Pro Gly
    4595                4600                4605

Xaa Gly Val Pro Gly Xaa Gly Val Pro Gly Xaa Gly Val Pro Gly
    4610                4615                4620

Xaa Gly Val Pro Gly Xaa Gly Val Pro Gly Xaa Gly Val Pro Gly
    4625                4630                4635

Xaa Gly Val Pro Gly Xaa Gly Val Pro Gly Xaa Gly Val Pro Gly
    4640                4645                4650

Xaa Gly Val Pro Gly Xaa Gly Val Pro Gly Xaa Gly Val Pro Gly
    4655                4660                4665

Xaa Gly Val Pro Gly Xaa Gly Val Pro Gly Xaa Gly Val Pro Gly
    4670                4675                4680

Xaa Gly Val Pro Gly Xaa Gly Val Pro Gly Xaa Gly Val Pro Gly
    4685                4690                4695

Xaa Gly Val Pro Gly Xaa Gly Val Pro Gly Xaa Gly Val Pro Gly
    4700                4705                4710

Xaa Gly Val Pro Gly Xaa Gly Val Pro Gly Xaa Gly Val Pro Gly
    4715                4720                4725

Xaa Gly Val Pro Gly Xaa Gly Val Pro Gly Xaa Gly Val Pro Gly
    4730                4735                4740

Xaa Gly Val Pro Gly Xaa Gly Val Pro Gly Xaa Gly Val Pro Gly
    4745                4750                4755

Xaa Gly Val Pro Gly Xaa Gly Val Pro Gly Xaa Gly Val Pro Gly
    4760                4765                4770

Xaa Gly Val Pro Gly Xaa Gly Val Pro Gly Xaa Gly Val Pro Gly
    4775                4780                4785

Xaa Gly Val Pro Gly Xaa Gly Val Pro Gly Xaa Gly Val Pro Gly
    4790                4795                4800

Xaa Gly Val Pro Gly Xaa Gly Val Pro Gly Xaa Gly Val Pro Gly
    4805                4810                4815

Xaa Gly Val Pro Gly Xaa Gly Val Pro Gly Xaa Gly Val Pro Gly
    4820                4825                4830

Xaa Gly Val Pro Gly Xaa Gly Val Pro Gly Xaa Gly Val Pro Gly
    4835                4840                4845

Xaa Gly Val Pro Gly Xaa Gly Val Pro Gly Xaa Gly Val Pro Gly

-continued

```
                4850                4855                4860

Xaa Gly Val Pro Gly Xaa Gly Val Pro Gly Xaa Gly Val Pro Gly
        4865                4870                4875

Xaa Gly Val Pro Gly Xaa Gly Val Pro Gly Xaa Gly Val Pro Gly
        4880                4885                4890

Xaa Gly Val Pro Gly Xaa Gly Val Pro Gly Xaa Gly Val Pro Gly
        4895                4900                4905

Xaa Gly Val Pro Gly Xaa Gly Val Pro Gly Xaa Gly Val Pro Gly
        4910                4915                4920

Xaa Gly Val Pro Gly Xaa Gly Val Pro Gly Xaa Gly Val Pro Gly
        4925                4930                4935

Xaa Gly Val Pro Gly Xaa Gly Val Pro Gly Xaa Gly Val Pro Gly
        4940                4945                4950

Xaa Gly Val Pro Gly Xaa Gly Val Pro Gly Xaa Gly Val Pro Gly
        4955                4960                4965

Xaa Gly Val Pro Gly Xaa Gly Val Pro Gly Xaa Gly Val Pro Gly
        4970                4975                4980

Xaa Gly Val Pro Gly Xaa Gly Val Pro Gly Xaa Gly Val Pro Gly
        4985                4990                4995

Xaa Gly Val Pro Gly Xaa Gly Val Pro Gly Xaa Gly Val Pro Gly
        5000                5005                5010

Xaa Gly Val Pro Gly Xaa Gly Val Pro Gly Xaa Gly Val Pro Gly
        5015                5020                5025

Xaa Gly Val Pro Gly Xaa Gly Val Pro Gly Xaa Gly Val Pro Gly
        5030                5035                5040

Xaa Gly Val Pro Gly Xaa Gly Val Pro Gly Xaa Gly Val Pro Gly
        5045                5050                5055

Xaa Gly Val Pro Gly Xaa Gly Val Pro Gly Xaa Gly Val Pro Gly
        5060                5065                5070

Xaa Gly Val Pro Gly Xaa Gly Val Pro Gly Xaa Gly Val Pro Gly
        5075                5080                5085

Xaa Gly Val Pro Gly Xaa Gly Val Pro Gly Xaa Gly Val Pro Gly
        5090                5095                5100

Xaa Gly Val Pro Gly Xaa Gly Val Pro Gly Xaa Gly Val Pro Gly
        5105                5110                5115

Xaa Gly Val Pro Gly Xaa Gly Val Pro Gly Xaa Gly Val Pro Gly
        5120                5125                5130

Xaa Gly Val Pro Gly Xaa Gly Val Pro Gly Xaa Gly Val Pro Gly
        5135                5140                5145

Xaa Gly Val Pro Gly Xaa Gly Val Pro Gly Xaa Gly Val Pro Gly
        5150                5155                5160

Xaa Gly Val Pro Gly Xaa Gly Val Pro Gly Xaa Gly Val Pro Gly
        5165                5170                5175

Xaa Gly Val Pro Gly Xaa Gly Val Pro Gly Xaa Gly Val Pro Gly
        5180                5185                5190

Xaa Gly Val Pro Gly Xaa Gly Val Pro Gly Xaa Gly Val Pro Gly
        5195                5200                5205

Xaa Gly Val Pro Gly Xaa Gly Val Pro Gly Xaa Gly Val Pro Gly
        5210                5215                5220

Xaa Gly Val Pro Gly Xaa Gly Val Pro Gly Xaa Gly Val Pro Gly
        5225                5230                5235

Xaa Gly Val Pro Gly Xaa Gly Val Pro Gly Xaa Gly Val Pro Gly
        5240                5245                5250
```

Xaa Gly Val Pro Gly Xaa Gly Val Pro Gly Xaa Gly Val Pro Gly
5255                5260                5265

Xaa Gly Val Pro Gly Xaa Gly Val Pro Gly Xaa Gly Val Pro Gly
5270                5275                5280

Xaa Gly Val Pro Gly Xaa Gly Val Pro Gly Xaa Gly Val Pro Gly
5285                5290                5295

Xaa Gly Val Pro Gly Xaa Gly Val Pro Gly Xaa Gly Val Pro Gly
5300                5305                5310

Xaa Gly Val Pro Gly Xaa Gly Val Pro Gly Xaa Gly Val Pro Gly
5315                5320                5325

Xaa Gly Val Pro Gly Xaa Gly Val Pro Gly Xaa Gly Val Pro Gly
5330                5335                5340

Xaa Gly Val Pro Gly Xaa Gly Val Pro Gly Xaa Gly Val Pro Gly
5345                5350                5355

Xaa Gly Val Pro Gly Xaa Gly Val Pro Gly Xaa Gly Val Pro Gly
5360                5365                5370

Xaa Gly Val Pro Gly Xaa Gly Val Pro Gly Xaa Gly Val Pro Gly
5375                5380                5385

Xaa Gly Val Pro Gly Xaa Gly Val Pro Gly Xaa Gly Val Pro Gly
5390                5395                5400

Xaa Gly Val Pro Gly Xaa Gly Val Pro Gly Xaa Gly Val Pro Gly
5405                5410                5415

Xaa Gly Val Pro Gly Xaa Gly Val Pro Gly Xaa Gly Val Pro Gly
5420                5425                5430

Xaa Gly Val Pro Gly Xaa Gly Val Pro Gly Xaa Gly Val Pro Gly
5435                5440                5445

Xaa Gly Val Pro Gly Xaa Gly Val Pro Gly Xaa Gly Val Pro Gly
5450                5455                5460

Xaa Gly Val Pro Gly Xaa Gly Val Pro Gly Xaa Gly Val Pro Gly
5465                5470                5475

Xaa Gly Val Pro Gly Xaa Gly Val Pro Gly Xaa Gly Val Pro Gly
5480                5485                5490

Xaa Gly Val Pro Gly Xaa Gly Val Pro Gly Xaa Gly Val Pro Gly
5495                5500                5505

Xaa Gly Val Pro Gly Xaa Gly Val Pro Gly Xaa Gly Val Pro Gly
5510                5515                5520

Xaa Gly Val Pro Gly Xaa Gly Val Pro Gly Xaa Gly Val Pro Gly
5525                5530                5535

Xaa Gly Val Pro Gly Xaa Gly Val Pro Gly Xaa Gly Val Pro Gly
5540                5545                5550

Xaa Gly Val Pro Gly Xaa Gly Val Pro Gly Xaa Gly Val Pro Gly
5555                5560                5565

Xaa Gly Val Pro Gly Xaa Gly Val Pro Gly Xaa Gly Val Pro Gly
5570                5575                5580

Xaa Gly Val Pro Gly Xaa Gly Val Pro Gly Xaa Gly Val Pro Gly
5585                5590                5595

Xaa Gly Val Pro Gly Xaa Gly Val Pro Gly Xaa Gly Val Pro Gly
5600                5605                5610

Xaa Gly Val Pro Gly Xaa Gly Val Pro Gly Xaa Gly Val Pro Gly
5615                5620                5625

Xaa Gly Val Pro Gly Xaa Gly Val Pro Gly Xaa Gly Val Pro Gly
5630                5635                5640

Xaa Gly Val Pro Gly Xaa Gly Val Pro Gly Xaa Gly Val Pro Gly
    5645                5650                5655

Xaa Gly Val Pro Gly Xaa Gly Val Pro Gly Xaa Gly Val Pro Gly
    5660                5665                5670

Xaa Gly Val Pro Gly Xaa Gly Val Pro Gly Xaa Gly Val Pro Gly
    5675                5680                5685

Xaa Gly Val Pro Gly Xaa Gly Val Pro Gly Xaa Gly Val Pro Gly
    5690                5695                5700

Xaa Gly Val Pro Gly Xaa Gly Val Pro Gly Xaa Gly Val Pro Gly
    5705                5710                5715

Xaa Gly Val Pro Gly Xaa Gly Val Pro Gly Xaa Gly Val Pro Gly
    5720                5725                5730

Xaa Gly Val Pro Gly Xaa Gly Val Pro Gly Xaa Gly Val Pro Gly
    5735                5740                5745

Xaa Gly Val Pro Gly Xaa Gly Val Pro Gly Xaa Gly Val Pro Gly
    5750                5755                5760

Xaa Gly Val Pro Gly Xaa Gly Val Pro Gly Xaa Gly Val Pro Gly
    5765                5770                5775

Xaa Gly Val Pro Gly Xaa Gly Val Pro Gly Xaa Gly Val Pro Gly
    5780                5785                5790

Xaa Gly Val Pro Gly Xaa Gly Val Pro Gly Xaa Gly Val Pro Gly
    5795                5800                5805

Xaa Gly Val Pro Gly Xaa Gly Val Pro Gly Xaa Gly Val Pro Gly
    5810                5815                5820

Xaa Gly Val Pro Gly Xaa Gly Val Pro Gly Xaa Gly Val Pro Gly
    5825                5830                5835

Xaa Gly Val Pro Gly Xaa Gly Val Pro Gly Xaa Gly Val Pro Gly
    5840                5845                5850

Xaa Gly Val Pro Gly Xaa Gly Val Pro Gly Xaa Gly Val Pro Gly
    5855                5860                5865

Xaa Gly Val Pro Gly Xaa Gly Val Pro Gly Xaa Gly Val Pro Gly
    5870                5875                5880

Xaa Gly Val Pro Gly Xaa Gly Val Pro Gly Xaa Gly Val Pro Gly
    5885                5890                5895

Xaa Gly Val Pro Gly Xaa Gly Val Pro Gly Xaa Gly Val Pro Gly
    5900                5905                5910

Xaa Gly Val Pro Gly Xaa Gly Val Pro Gly Xaa Gly Val Pro Gly
    5915                5920                5925

Xaa Gly Val Pro Gly Xaa Gly Val Pro Gly Xaa Gly Val Pro Gly
    5930                5935                5940

Xaa Gly Val Pro Gly Xaa Gly Val Pro Gly Xaa Gly Val Pro Gly
    5945                5950                5955

Xaa Gly Val Pro Gly Xaa Gly Val Pro Gly Xaa Gly Val Pro Gly
    5960                5965                5970

Xaa Gly Val Pro Gly Xaa Gly Val Pro Gly Xaa Gly Val Pro Gly
    5975                5980                5985

Xaa Gly Val Pro Gly Xaa Gly Val Pro Gly Xaa Gly Val Pro Gly
    5990                5995                6000

Xaa Gly Val Pro Gly Xaa Gly Val Pro Gly Xaa Gly Val Pro Gly
    6005                6010                6015

Xaa Gly Val Pro Gly Xaa Gly Val Pro Gly Xaa Gly Val Pro Gly
    6020                6025                6030

Xaa Gly Val Pro Gly Xaa Gly Val Pro Gly Xaa Gly Val Pro Gly 6035                6040                6045

Xaa Gly Val Pro Gly Xaa Gly Val Pro Gly Xaa Gly Val Pro Gly
            6050                6055                6060

Xaa Gly Val Pro Gly Xaa Gly Val Pro Gly Xaa Gly Val Pro Gly
            6065                6070                6075

Xaa Gly Val Pro Gly Xaa Gly Val Pro Gly Xaa Gly Val Pro Gly
            6080                6085                6090

Xaa Gly Val Pro Gly Xaa Gly Val Pro Gly Xaa Gly Val Pro Gly
            6095                6100                6105

Xaa Gly Val Pro Gly Xaa Gly Val Pro Gly Xaa Gly Val Pro Gly
            6110                6115                6120

Xaa Gly Val Pro Gly Xaa Gly Val Pro Gly Xaa Gly Val Pro Gly
            6125                6130                6135

Xaa Gly Val Pro Gly Xaa Gly Val Pro Gly Xaa Gly Val Pro Gly
            6140                6145                6150

Xaa Gly Val Pro Gly Xaa Gly Val Pro Gly Xaa Gly Val Pro Gly
            6155                6160                6165

Xaa Gly Val Pro Gly Xaa Gly Val Pro Gly Xaa Gly Val Pro Gly
            6170                6175                6180

Xaa Gly Val Pro Gly Xaa Gly Val Pro Gly Xaa Gly Val Pro Gly
            6185                6190                6195

Xaa Gly Val Pro Gly Xaa Gly Val Pro Gly Xaa Gly Val Pro Gly
            6200                6205                6210

Xaa Gly Val Pro Gly Xaa Gly Val Pro Gly Xaa Gly Val Pro Gly
            6215                6220                6225

Xaa Gly Val Pro Gly Xaa Gly Val Pro Gly Xaa Gly Val Pro Gly
            6230                6235                6240

Xaa Gly Val Pro Gly Xaa Gly Val Pro Gly Xaa Gly Val Pro Gly
            6245                6250                6255

Xaa Gly Val Pro Gly Xaa Gly Val Pro Gly Xaa Gly Val Pro Gly
            6260                6265                6270

Xaa Gly Val Pro Gly Xaa Gly Val Pro Gly Xaa Gly Val Pro Gly
            6275                6280                6285

Xaa Gly Val Pro Gly Xaa Gly Val Pro Gly Xaa Gly Val Pro Gly
            6290                6295                6300

Xaa Gly Val Pro Gly Xaa Gly Val Pro Gly Xaa Gly Val Pro Gly
            6305                6310                6315

Xaa Gly Val Pro Gly Xaa Gly Val Pro Gly Xaa Gly Val Pro Gly
            6320                6325                6330

Xaa Gly Val Pro Gly Xaa Gly Val Pro Gly Xaa Gly Val Pro Gly
            6335                6340                6345

Xaa Gly Val Pro Gly Xaa Gly Val Pro Gly Xaa Gly Val Pro Gly
            6350                6355                6360

Xaa Gly Val Pro Gly Xaa Gly Val Pro Gly Xaa Gly Val Pro Gly
            6365                6370                6375

Xaa Gly Val Pro Gly Xaa Gly Val Pro Gly Xaa Gly Val Pro Gly
            6380                6385                6390

Xaa Gly Val Pro Gly Xaa Gly Val Pro Gly Xaa Gly Val Pro Gly
            6395                6400                6405

Xaa Gly Val Pro Gly Xaa Gly Val Pro Gly Xaa Gly Val Pro Gly
            6410                6415                6420

Xaa Gly Val Pro Gly Xaa Gly Val Pro Gly Xaa Gly Val Pro Gly
            6425                6430                6435

```
Xaa Gly Val Pro Gly Xaa Gly Val Pro Gly Xaa Gly Val Pro Gly
    6440                6445                6450

Xaa Gly Val Pro Gly Xaa Gly Val Pro Gly Xaa Gly Val Pro Gly
    6455                6460                6465

Xaa Gly Val Pro Gly Xaa Gly Val Pro Gly Xaa Gly Val Pro Gly
    6470                6475                6480

Xaa Gly Val Pro Gly Xaa Gly Val Pro Gly Xaa Gly Val Pro Gly
    6485                6490                6495

Xaa Gly Val Pro Gly Xaa Gly Val Pro Gly Xaa Gly Val Pro Gly
    6500                6505                6510

Xaa Gly Val Pro Gly Xaa Gly Val Pro Gly Xaa Gly Val Pro Gly
    6515                6520                6525

Xaa Gly Val Pro Gly Xaa Gly Val Pro Gly Xaa Gly Val Pro Gly
    6530                6535                6540

Xaa Gly Val Pro Gly Xaa Gly Val Pro Gly Xaa Gly Val Pro Gly
    6545                6550                6555

Xaa Gly Val Pro Gly Xaa Gly Val Pro Gly Xaa Gly Val Pro Gly
    6560                6565                6570

Xaa Gly Val Pro Gly Xaa Gly Val Pro Gly Xaa Gly Val Pro Gly
    6575                6580                6585

Xaa Gly Val Pro Gly Xaa Gly Val Pro Gly Xaa Gly Val Pro Gly
    6590                6595                6600

Xaa Gly Val Pro Gly Xaa Gly Val Pro Gly Xaa Gly Val Pro Gly
    6605                6610                6615

Xaa Gly Val Pro Gly Xaa Gly Val Pro Gly Xaa Gly Val Pro Gly
    6620                6625                6630

Xaa Gly Val Pro Gly Xaa Gly Val Pro Gly Xaa Gly Val Pro Gly
    6635                6640                6645

Xaa Gly Val Pro Gly Xaa Gly Val Pro Gly Xaa Gly Val Pro Gly
    6650                6655                6660

Xaa Gly Val Pro Gly Xaa Gly Val Pro Gly Xaa Gly Val Pro Gly
    6665                6670                6675

Xaa Gly Val Pro Gly Xaa Gly Val Pro Gly Xaa Gly Val Pro Gly
    6680                6685                6690

Xaa Gly Val Pro Gly Xaa Gly Val Pro Gly Xaa Gly Val Pro Gly
    6695                6700                6705

Xaa Gly Val Pro Gly Xaa Gly Val Pro Gly Xaa Gly Val Pro Gly
    6710                6715                6720

Xaa Gly Val Pro Gly Xaa Gly Val Pro Gly Xaa Gly Val Pro Gly
    6725                6730                6735

Xaa Gly Val Pro Gly Xaa Gly Val Pro Gly Xaa Gly Val Pro Gly
    6740                6745                6750

Xaa Gly Val Pro Gly Xaa Gly Val Pro Gly Xaa Gly Val Pro Gly
    6755                6760                6765

Xaa Gly Val Pro Gly Xaa Gly Val Pro Gly Xaa Gly Val Pro Gly
    6770                6775                6780

Xaa Gly Val Pro Gly Xaa Gly Val Pro Gly Xaa Gly Val Pro Gly
    6785                6790                6795

Xaa Gly Val Pro Gly Xaa Gly Val Pro Gly Xaa Gly Val Pro Gly
    6800                6805                6810

Xaa Gly Val Pro Gly Xaa Gly Val Pro Gly Xaa Gly Val Pro Gly
    6815                6820                6825
```

-continued

Xaa Gly Val Pro Gly Xaa Gly Val Pro Gly Xaa Gly Val Pro Gly
    6830              6835              6840

Xaa Gly Val Pro Gly Xaa Gly Val Pro Gly Xaa Gly Val Pro Gly
    6845              6850              6855

Xaa Gly Val Pro Gly Xaa Gly Val Pro Gly Xaa Gly Val Pro Gly
    6860              6865              6870

Xaa Gly Val Pro Gly Xaa Gly Val Pro Gly Xaa Gly Val Pro Gly
    6875              6880              6885

Xaa Gly Val Pro Gly Xaa Gly Val Pro Gly Xaa Gly Val Pro Gly
    6890              6895              6900

Xaa Gly Val Pro Gly Xaa Gly Val Pro Gly Xaa Gly Val Pro Gly
    6905              6910              6915

Xaa Gly Val Pro Gly Xaa Gly Val Pro Gly Xaa Gly Val Pro Gly
    6920              6925              6930

Xaa Gly Val Pro Gly Xaa Gly Val Pro Gly Xaa Gly Val Pro Gly
    6935              6940              6945

Xaa Gly Val Pro Gly Xaa Gly Val Pro Gly Xaa Gly Val Pro Gly
    6950              6955              6960

Xaa Gly Val Pro Gly Xaa Gly Val Pro Gly Xaa Gly Val Pro Gly
    6965              6970              6975

Xaa Gly Val Pro Gly Xaa Gly Val Pro Gly Xaa Gly Val Pro Gly
    6980              6985              6990

Xaa Gly Val Pro Gly Xaa Gly Val Pro Gly Xaa Gly Val Pro Gly
    6995              7000              7005

Xaa Gly Val Pro Gly Xaa Gly Val Pro Gly Xaa Gly Val Pro Gly
    7010              7015              7020

Xaa Gly Val Pro Gly Xaa Gly Val Pro Gly Xaa Gly Val Pro Gly
    7025              7030              7035

Xaa Gly Val Pro Gly Xaa Gly Val Pro Gly Xaa Gly Val Pro Gly
    7040              7045              7050

Xaa Gly Val Pro Gly Xaa Gly Val Pro Gly Xaa Gly Val Pro Gly
    7055              7060              7065

Xaa Gly Val Pro Gly Xaa Gly Val Pro Gly Xaa Gly Val Pro Gly
    7070              7075              7080

Xaa Gly Val Pro Gly Xaa Gly Val Pro Gly Xaa Gly Val Pro Gly
    7085              7090              7095

Xaa Gly Val Pro Gly Xaa Gly Val Pro Gly Xaa Gly Val Pro Gly
    7100              7105              7110

Xaa Gly Val Pro Gly Xaa Gly Val Pro Gly Xaa Gly Val Pro Gly
    7115              7120              7125

Xaa Gly Val Pro Gly Xaa Gly Val Pro Gly Xaa Gly Val Pro Gly
    7130              7135              7140

Xaa Gly Val Pro Gly Xaa Gly Val Pro Gly Xaa Gly Val Pro Gly
    7145              7150              7155

Xaa Gly Val Pro Gly Xaa Gly Val Pro Gly Xaa Gly Val Pro Gly
    7160              7165              7170

Xaa Gly Val Pro Gly Xaa Gly Val Pro Gly Xaa Gly Val Pro Gly
    7175              7180              7185

Xaa Gly Val Pro Gly Xaa Gly Val Pro Gly Xaa Gly Val Pro Gly
    7190              7195              7200

Xaa Gly Val Pro Gly Xaa Gly Val Pro Gly Xaa Gly Val Pro Gly
    7205              7210              7215

Xaa Gly Val Pro Gly Xaa Gly Val Pro Gly Xaa Gly Val Pro Gly

```
            7220                7225                7230

Xaa Gly Val Pro Gly Xaa Gly Val Pro Gly Xaa Gly Val Pro Gly
            7235                7240                7245

Xaa Gly Val Pro Gly Xaa Gly Val Pro Gly Xaa Gly Val Pro Gly
            7250                7255                7260

Xaa Gly Val Pro Gly Xaa Gly Val Pro Gly Xaa Gly Val Pro Gly
            7265                7270                7275

Xaa Gly Val Pro Gly Xaa Gly Val Pro Gly Xaa Gly Val Pro Gly
            7280                7285                7290

Xaa Gly Val Pro Gly Xaa Gly Val Pro Gly Xaa Gly Val Pro Gly
            7295                7300                7305

Xaa Gly Val Pro Gly Xaa Gly Val Pro Gly Xaa Gly Val Pro Gly
            7310                7315                7320

Xaa Gly Val Pro Gly Xaa Gly Val Pro Gly Xaa Gly Val Pro Gly
            7325                7330                7335

Xaa Gly Val Pro Gly Xaa Gly Val Pro Gly Xaa Gly Val Pro Gly
            7340                7345                7350

Xaa Gly Val Pro Gly Xaa Gly Val Pro Gly Xaa Gly Val Pro Gly
            7355                7360                7365

Xaa Gly Val Pro Gly Xaa Gly Val Pro Gly Xaa Gly Val Pro Gly
            7370                7375                7380

Xaa Gly Val Pro Gly Xaa Gly Val Pro Gly Xaa Gly Val Pro Gly
            7385                7390                7395

Xaa Gly Val Pro Gly Xaa Gly Val Pro Gly Xaa Gly Val Pro Gly
            7400                7405                7410

Xaa Gly Val Pro Gly Xaa Gly Val Pro Gly Xaa Gly Val Pro Gly
            7415                7420                7425

Xaa Gly Val Pro Gly Xaa Gly Val Pro Gly Xaa Gly Val Pro Gly
            7430                7435                7440

Xaa Gly Val Pro Gly Xaa Gly Val Pro Gly Xaa Gly Val Pro Gly
            7445                7450                7455

Xaa Gly Val Pro Gly Xaa Gly Val Pro Gly Xaa Gly Val Pro Gly
            7460                7465                7470

Xaa Gly Val Pro Gly Xaa Gly Val Pro Gly Xaa Gly Val Pro Gly
            7475                7480                7485

Xaa Gly Val Pro Gly Xaa Gly Val Pro Gly Xaa Gly Val Pro Gly
            7490                7495                7500

Xaa Gly Val Pro Gly Xaa Gly Val Pro Gly Xaa Gly Val Pro Gly
            7505                7510                7515

Xaa Gly Val Pro Gly Xaa Gly Val Pro Gly Xaa Gly Val Pro Gly
            7520                7525                7530

Xaa Gly Val Pro Gly Xaa Gly Val Pro Gly Xaa Gly Val Pro Gly
            7535                7540                7545

Xaa Gly Val Pro Gly Xaa Gly Val Pro Gly Xaa Gly Val Pro Gly
            7550                7555                7560

Xaa Gly Val Pro Gly Xaa Gly Val Pro Gly Xaa Gly Val Pro Gly
            7565                7570                7575

Xaa Gly Val Pro Gly Xaa Gly Val Pro Gly Xaa Gly Val Pro Gly
            7580                7585                7590

Xaa Gly Val Pro Gly Xaa Gly Val Pro Gly Xaa Gly Val Pro Gly
            7595                7600                7605

Xaa Gly Val Pro Gly Xaa Gly Val Pro Gly Xaa Gly Val Pro Gly
            7610                7615                7620
```

Xaa Gly Val Pro Gly Xaa Gly Val Pro Gly Xaa Gly Val Pro Gly
    7625                7630                7635

Xaa Gly Val Pro Gly Xaa Gly Val Pro Gly Xaa Gly Val Pro Gly
    7640                7645                7650

Xaa Gly Val Pro Gly Xaa Gly Val Pro Gly Xaa Gly Val Pro Gly
    7655                7660                7665

Xaa Gly Val Pro Gly Xaa Gly Val Pro Gly Xaa Gly Val Pro Gly
    7670                7675                7680

Xaa Gly Val Pro Gly Xaa Gly Val Pro Gly Xaa Gly Val Pro Gly
    7685                7690                7695

Xaa Gly Val Pro Gly Xaa Gly Val Pro Gly Xaa Gly Val Pro Gly
    7700                7705                7710

Xaa Gly Val Pro Gly Xaa Gly Val Pro Gly Xaa Gly Val Pro Gly
    7715                7720                7725

Xaa Gly Val Pro Gly Xaa Gly Val Pro Gly Xaa Gly Val Pro Gly
    7730                7735                7740

Xaa Gly Val Pro Gly Xaa Gly Val Pro Gly Xaa Gly Val Pro Gly
    7745                7750                7755

Xaa Gly Val Pro Gly Xaa Gly Val Pro Gly Xaa Gly Val Pro Gly
    7760                7765                7770

Xaa Gly Val Pro Gly Xaa Gly Val Pro Gly Xaa Gly Val Pro Gly
    7775                7780                7785

Xaa Gly Val Pro Gly Xaa Gly Val Pro Gly Xaa Gly Val Pro Gly
    7790                7795                7800

Xaa Gly Val Pro Gly Xaa Gly Val Pro Gly Xaa Gly Val Pro Gly
    7805                7810                7815

Xaa Gly Val Pro Gly Xaa Gly Val Pro Gly Xaa Gly Val Pro Gly
    7820                7825                7830

Xaa Gly Val Pro Gly Xaa Gly Val Pro Gly Xaa Gly Val Pro Gly
    7835                7840                7845

Xaa Gly Val Pro Gly Xaa Gly Val Pro Gly Xaa Gly Val Pro Gly
    7850                7855                7860

Xaa Gly Val Pro Gly Xaa Gly Val Pro Gly Xaa Gly Val Pro Gly
    7865                7870                7875

Xaa Gly Val Pro Gly Xaa Gly Val Pro Gly Xaa Gly Val Pro Gly
    7880                7885                7890

Xaa Gly Val Pro Gly Xaa Gly Val Pro Gly Xaa Gly Val Pro Gly
    7895                7900                7905

Xaa Gly Val Pro Gly Xaa Gly Val Pro Gly Xaa Gly Val Pro Gly
    7910                7915                7920

Xaa Gly Val Pro Gly Xaa Gly Val Pro Gly Xaa Gly Val Pro Gly
    7925                7930                7935

Xaa Gly Val Pro Gly Xaa Gly Val Pro Gly Xaa Gly Val Pro Gly
    7940                7945                7950

Xaa Gly Val Pro Gly Xaa Gly Val Pro Gly Xaa Gly Val Pro Gly
    7955                7960                7965

Xaa Gly Val Pro Gly Xaa Gly Val Pro Gly Xaa Gly Val Pro Gly
    7970                7975                7980

Xaa Gly Val Pro Gly Xaa Gly Val Pro Gly Xaa Gly Val Pro Gly
    7985                7990                7995

Xaa Gly Val Pro Gly Xaa Gly Val Pro Gly Xaa Gly Val Pro Gly
    8000                8005                8010

Xaa Gly Val Pro Gly Xaa Gly Val Pro Gly Xaa Gly Val Pro Gly
    8015                8020                8025

Xaa Gly Val Pro Gly Xaa Gly Val Pro Gly Xaa Gly Val Pro Gly
    8030                8035                8040

Xaa Gly Val Pro Gly Xaa Gly Val Pro Gly Xaa Gly Val Pro Gly
    8045                8050                8055

Xaa Gly Val Pro Gly Xaa Gly Val Pro Gly Xaa Gly Val Pro Gly
    8060                8065                8070

Xaa Gly Val Pro Gly Xaa Gly Val Pro Gly Xaa Gly Val Pro Gly
    8075                8080                8085

Xaa Gly Val Pro Gly Xaa Gly Val Pro Gly Xaa Gly Val Pro Gly
    8090                8095                8100

Xaa Gly Val Pro Gly Xaa Gly Val Pro Gly Xaa Gly Val Pro Gly
    8105                8110                8115

Xaa Gly Val Pro Gly Xaa Gly Val Pro Gly Xaa Gly Val Pro Gly
    8120                8125                8130

Xaa Gly Val Pro Gly Xaa Gly Val Pro Gly Xaa Gly Val Pro Gly
    8135                8140                8145

Xaa Gly Val Pro Gly Xaa Gly Val Pro Gly Xaa Gly Val Pro Gly
    8150                8155                8160

Xaa Gly Val Pro Gly Xaa Gly Val Pro Gly Xaa Gly Val Pro Gly
    8165                8170                8175

Xaa Gly Val Pro Gly Xaa Gly Val Pro Gly Xaa Gly Val Pro Gly
    8180                8185                8190

Xaa Gly Val Pro Gly Xaa Gly Val Pro Gly Xaa Gly Val Pro Gly
    8195                8200                8205

Xaa Gly Val Pro Gly Xaa Gly Val Pro Gly Xaa Gly Val Pro Gly
    8210                8215                8220

Xaa Gly Val Pro Gly Xaa Gly Val Pro Gly Xaa Gly Val Pro Gly
    8225                8230                8235

Xaa Gly Val Pro Gly Xaa Gly Val Pro Gly Xaa Gly Val Pro Gly
    8240                8245                8250

Xaa Gly Val Pro Gly Xaa Gly Val Pro Gly Xaa Gly Val Pro Gly
    8255                8260                8265

Xaa Gly Val Pro Gly Xaa Gly Val Pro Gly Xaa Gly Val Pro Gly
    8270                8275                8280

Xaa Gly Val Pro Gly Xaa Gly Val Pro Gly Xaa Gly Val Pro Gly
    8285                8290                8295

Xaa Gly Val Pro Gly Xaa Gly Val Pro Gly Xaa Gly Val Pro Gly
    8300                8305                8310

Xaa Gly Val Pro Gly Xaa Gly Val Pro Gly Xaa Gly Val Pro Gly
    8315                8320                8325

Xaa Gly Val Pro Gly Xaa Gly Val Pro Gly Xaa Gly Val Pro Gly
    8330                8335                8340

Xaa Gly Val Pro Gly Xaa Gly Val Pro Gly Xaa Gly Val Pro Gly
    8345                8350                8355

Xaa Gly Val Pro Gly Xaa Gly Val Pro Gly Xaa Gly Val Pro Gly
    8360                8365                8370

Xaa Gly Val Pro Gly Xaa Gly Val Pro Gly Xaa Gly Val Pro Gly
    8375                8380                8385

Xaa Gly Val Pro Gly Xaa Gly Val Pro Gly Xaa Gly Val Pro Gly
    8390                8395                8400

Xaa Gly Val Pro Gly Xaa Gly Val Pro Gly Xaa Gly Val Pro Gly

-continued

```
            8405                8410                8415

Xaa Gly  Val Pro Gly Xaa Gly  Val Pro Gly Xaa Gly  Val Pro Gly
    8420                8425                8430

Xaa Gly  Val Pro Gly Xaa Gly  Val Pro Gly Xaa Gly  Val Pro Gly
    8435                8440                8445

Xaa Gly  Val Pro Gly Xaa Gly  Val Pro Gly Xaa Gly  Val Pro Gly
    8450                8455                8460

Xaa Gly  Val Pro Gly Xaa Gly  Val Pro Gly Xaa Gly  Val Pro Gly
    8465                8470                8475

Xaa Gly  Val Pro Gly Xaa Gly  Val Pro Gly Xaa Gly  Val Pro Gly
    8480                8485                8490

Xaa Gly  Val Pro Gly Xaa Gly  Val Pro Gly Xaa Gly  Val Pro Gly
    8495                8500                8505

Xaa Gly  Val Pro Gly Xaa Gly  Val Pro Gly Xaa Gly  Val Pro Gly
    8510                8515                8520

Xaa Gly  Val Pro Gly Xaa Gly  Val Pro Gly Xaa Gly  Val Pro Gly
    8525                8530                8535

Xaa Gly  Val Pro Gly Xaa Gly  Val Pro Gly Xaa Gly  Val Pro Gly
    8540                8545                8550

Xaa Gly  Val Pro Gly Xaa Gly  Val Pro Gly Xaa Gly  Val Pro Gly
    8555                8560                8565

Xaa Gly  Val Pro Gly Xaa Gly  Val Pro Gly Xaa Gly  Val Pro Gly
    8570                8575                8580

Xaa Gly  Val Pro Gly Xaa Gly  Val Pro Gly Xaa Gly  Val Pro Gly
    8585                8590                8595

Xaa Gly  Val Pro Gly Xaa Gly  Val Pro Gly Xaa Gly  Val Pro Gly
    8600                8605                8610

Xaa Gly  Val Pro Gly Xaa Gly  Val Pro Gly Xaa Gly  Val Pro Gly
    8615                8620                8625

Xaa Gly  Val Pro Gly Xaa Gly  Val Pro Gly Xaa Gly  Val Pro Gly
    8630                8635                8640

Xaa Gly  Val Pro Gly Xaa Gly  Val Pro Gly Xaa Gly  Val Pro Gly
    8645                8650                8655

Xaa Gly  Val Pro Gly Xaa Gly  Val Pro Gly Xaa Gly  Val Pro Gly
    8660                8665                8670

Xaa Gly  Val Pro Gly Xaa Gly  Val Pro Gly Xaa Gly  Val Pro Gly
    8675                8680                8685

Xaa Gly  Val Pro Gly Xaa Gly  Val Pro Gly Xaa Gly  Val Pro Gly
    8690                8695                8700

Xaa Gly  Val Pro Gly Xaa Gly  Val Pro Gly Xaa Gly  Val Pro Gly
    8705                8710                8715

Xaa Gly  Val Pro Gly Xaa Gly  Val Pro Gly Xaa Gly  Val Pro Gly
    8720                8725                8730

Xaa Gly  Val Pro Gly Xaa Gly  Val Pro Gly Xaa Gly  Val Pro Gly
    8735                8740                8745

Xaa Gly  Val Pro Gly Xaa Gly  Val Pro Gly Xaa Gly  Val Pro Gly
    8750                8755                8760

Xaa Gly  Val Pro Gly Xaa Gly  Val Pro Gly Xaa Gly  Val Pro Gly
    8765                8770                8775

Xaa Gly  Val Pro Gly Xaa Gly  Val Pro Gly Xaa Gly  Val Pro Gly
    8780                8785                8790

Xaa Gly  Val Pro Gly Xaa Gly  Val Pro Gly Xaa Gly  Val Pro Gly
    8795                8800                8805
```

-continued

Xaa Gly Val Pro Gly Xaa Gly Val Pro Gly Xaa Gly Val Pro Gly
    8810                8815                8820

Xaa Gly Val Pro Gly Xaa Gly Val Pro Gly Xaa Gly Val Pro Gly
    8825                8830                8835

Xaa Gly Val Pro Gly Xaa Gly Val Pro Gly Xaa Gly Val Pro Gly
    8840                8845                8850

Xaa Gly Val Pro Gly Xaa Gly Val Pro Gly Xaa Gly Val Pro Gly
    8855                8860                8865

Xaa Gly Val Pro Gly Xaa Gly Val Pro Gly Xaa Gly Val Pro Gly
    8870                8875                8880

Xaa Gly Val Pro Gly Xaa Gly Val Pro Gly Xaa Gly Val Pro Gly
    8885                8890                8895

Xaa Gly Val Pro Gly Xaa Gly Val Pro Gly Xaa Gly Val Pro Gly
    8900                8905                8910

Xaa Gly Val Pro Gly Xaa Gly Val Pro Gly Xaa Gly Val Pro Gly
    8915                8920                8925

Xaa Gly Val Pro Gly Xaa Gly Val Pro Gly Xaa Gly Val Pro Gly
    8930                8935                8940

Xaa Gly Val Pro Gly Xaa Gly Val Pro Gly Xaa Gly Val Pro Gly
    8945                8950                8955

Xaa Gly Val Pro Gly Xaa Gly Val Pro Gly Xaa Gly Val Pro Gly
    8960                8965                8970

Xaa Gly Val Pro Gly Xaa Gly Val Pro Gly Xaa Gly Val Pro Gly
    8975                8980                8985

Xaa Gly Val Pro Gly Xaa Gly Val Pro Gly Xaa Gly Val Pro Gly
    8990                8995                9000

Xaa Gly Val Pro Gly Xaa Gly Val Pro Gly Xaa Gly Val Pro Gly
    9005                9010                9015

Xaa Gly Val Pro Gly Xaa Gly Val Pro Gly Xaa Gly Val Pro Gly
    9020                9025                9030

Xaa Gly Val Pro Gly Xaa Gly Val Pro Gly Xaa Gly Val Pro Gly
    9035                9040                9045

Xaa Gly Val Pro Gly Xaa Gly Val Pro Gly Xaa Gly Val Pro Gly
    9050                9055                9060

Xaa Gly Val Pro Gly Xaa Gly Val Pro Gly Xaa Gly Val Pro Gly
    9065                9070                9075

Xaa Gly Val Pro Gly Xaa Gly Val Pro Gly Xaa Gly Val Pro Gly
    9080                9085                9090

Xaa Gly Val Pro Gly Xaa Gly Val Pro Gly Xaa Gly Val Pro Gly
    9095                9100                9105

Xaa Gly Val Pro Gly Xaa Gly Val Pro Gly Xaa Gly Val Pro Gly
    9110                9115                9120

Xaa Gly Val Pro Gly Xaa Gly Val Pro Gly Xaa Gly Val Pro Gly
    9125                9130                9135

Xaa Gly Val Pro Gly Xaa Gly Val Pro Gly Xaa Gly Val Pro Gly
    9140                9145                9150

Xaa Gly Val Pro Gly Xaa Gly Val Pro Gly Xaa Gly Val Pro Gly
    9155                9160                9165

Xaa Gly Val Pro Gly Xaa Gly Val Pro Gly Xaa Gly Val Pro Gly
    9170                9175                9180

Xaa Gly Val Pro Gly Xaa Gly Val Pro Gly Xaa Gly Val Pro Gly
    9185                9190                9195

```
Xaa Gly  Val Pro Gly Xaa Gly  Val Pro Gly Xaa Gly  Val Pro Gly
    9200                 9205                 9210

Xaa Gly  Val Pro Gly Xaa Gly  Val Pro Gly Xaa Gly  Val Pro Gly
    9215                 9220                 9225

Xaa Gly  Val Pro Gly Xaa Gly  Val Pro Gly Xaa Gly  Val Pro Gly
    9230                 9235                 9240

Xaa Gly  Val Pro Gly Xaa Gly  Val Pro Gly Xaa Gly  Val Pro Gly
    9245                 9250                 9255

Xaa Gly  Val Pro Gly Xaa Gly  Val Pro Gly Xaa Gly  Val Pro Gly
    9260                 9265                 9270

Xaa Gly  Val Pro Gly Xaa Gly  Val Pro Gly Xaa Gly  Val Pro Gly
    9275                 9280                 9285

Xaa Gly  Val Pro Gly Xaa Gly  Val Pro Gly Xaa Gly  Val Pro Gly
    9290                 9295                 9300

Xaa Gly  Val Pro Gly Xaa Gly  Val Pro Gly Xaa Gly  Val Pro Gly
    9305                 9310                 9315

Xaa Gly  Val Pro Gly Xaa Gly  Val Pro Gly Xaa Gly  Val Pro Gly
    9320                 9325                 9330

Xaa Gly  Val Pro Gly Xaa Gly  Val Pro Gly Xaa Gly  Val Pro Gly
    9335                 9340                 9345

Xaa Gly  Val Pro Gly Xaa Gly  Val Pro Gly Xaa Gly  Val Pro Gly
    9350                 9355                 9360

Xaa Gly  Val Pro Gly Xaa Gly  Val Pro Gly Xaa Gly  Val Pro Gly
    9365                 9370                 9375

Xaa Gly  Val Pro Gly Xaa Gly  Val Pro Gly Xaa Gly  Val Pro Gly
    9380                 9385                 9390

Xaa Gly  Val Pro Gly Xaa Gly  Val Pro Gly Xaa Gly  Val Pro Gly
    9395                 9400                 9405

Xaa Gly  Val Pro Gly Xaa Gly  Val Pro Gly Xaa Gly  Val Pro Gly
    9410                 9415                 9420

Xaa Gly  Val Pro Gly Xaa Gly  Val Pro Gly Xaa Gly  Val Pro Gly
    9425                 9430                 9435

Xaa Gly  Val Pro Gly Xaa Gly  Val Pro Gly Xaa Gly  Val Pro Gly
    9440                 9445                 9450

Xaa Gly  Val Pro Gly Xaa Gly  Val Pro Gly Xaa Gly  Val Pro Gly
    9455                 9460                 9465

Xaa Gly  Val Pro Gly Xaa Gly  Val Pro Gly Xaa Gly  Val Pro Gly
    9470                 9475                 9480

Xaa Gly  Val Pro Gly Xaa Gly  Val Pro Gly Xaa Gly  Val Pro Gly
    9485                 9490                 9495

Xaa Gly  Val Pro Gly Xaa Gly  Val Pro Gly Xaa Gly  Val Pro Gly
    9500                 9505                 9510

Xaa Gly  Val Pro Gly Xaa Gly  Val Pro Gly Xaa Gly  Val Pro Gly
    9515                 9520                 9525

Xaa Gly  Val Pro Gly Xaa Gly  Val Pro Gly Xaa Gly  Val Pro Gly
    9530                 9535                 9540

Xaa Gly  Val Pro Gly Xaa Gly  Val Pro Gly Xaa Gly  Val Pro Gly
    9545                 9550                 9555

Xaa Gly  Val Pro Gly Xaa Gly  Val Pro Gly Xaa Gly  Val Pro Gly
    9560                 9565                 9570

Xaa Gly  Val Pro Gly Xaa Gly  Val Pro Gly Xaa Gly  Val Pro Gly
    9575                 9580                 9585

Xaa Gly  Val Pro Gly Xaa Gly  Val Pro Gly Xaa Gly  Val Pro Gly
```

-continued

```
              9590            9595            9600

Xaa Gly Val Pro Gly Xaa Gly Val Pro Gly Xaa Gly Val Pro Gly
      9605            9610            9615

Xaa Gly Val Pro Gly Xaa Gly Val Pro Gly Xaa Gly Val Pro Gly
      9620            9625            9630

Xaa Gly Val Pro Gly Xaa Gly Val Pro Gly Xaa Gly Val Pro Gly
      9635            9640            9645

Xaa Gly Val Pro Gly Xaa Gly Val Pro Gly Xaa Gly Val Pro Gly
      9650            9655            9660

Xaa Gly Val Pro Gly Xaa Gly Val Pro Gly Xaa Gly Val Pro Gly
      9665            9670            9675

Xaa Gly Val Pro Gly Xaa Gly Val Pro Gly Xaa Gly Val Pro Gly
      9680            9685            9690

Xaa Gly Val Pro Gly Xaa Gly Val Pro Gly Xaa Gly Val Pro Gly
      9695            9700            9705

Xaa Gly Val Pro Gly Xaa Gly Val Pro Gly Xaa Gly Val Pro Gly
      9710            9715            9720

Xaa Gly Val Pro Gly Xaa Gly Val Pro Gly Xaa Gly Val Pro Gly
      9725            9730            9735

Xaa Gly Val Pro Gly Xaa Gly Val Pro Gly Xaa Gly Val Pro Gly
      9740            9745            9750

Xaa Gly Val Pro Gly Xaa Gly Val Pro Gly Xaa Gly Val Pro Gly
      9755            9760            9765

Xaa Gly Val Pro Gly Xaa Gly Val Pro Gly Xaa Gly Val Pro Gly
      9770            9775            9780

Xaa Gly Val Pro Gly Xaa Gly Val Pro Gly Xaa Gly Val Pro Gly
      9785            9790            9795

Xaa Gly Val Pro Gly Xaa Gly Val Pro Gly Xaa Gly Val Pro Gly
      9800            9805            9810

Xaa Gly Val Pro Gly Xaa Gly Val Pro Gly Xaa Gly Val Pro Gly
      9815            9820            9825

Xaa Gly Val Pro Gly Xaa Gly Val Pro Gly Xaa Gly Val Pro Gly
      9830            9835            9840

Xaa Gly Val Pro Gly Xaa Gly Val Pro Gly Xaa Gly Val Pro Gly
      9845            9850            9855

Xaa Gly Val Pro Gly Xaa Gly Val Pro Gly Xaa Gly Val Pro Gly
      9860            9865            9870

Xaa Gly Val Pro Gly Xaa Gly Val Pro Gly Xaa Gly Val Pro Gly
      9875            9880            9885

Xaa Gly Val Pro Gly Xaa Gly Val Pro Gly Xaa Gly Val Pro Gly
      9890            9895            9900

Xaa Gly Val Pro Gly Xaa Gly Val Pro Gly Xaa Gly Val Pro Gly
      9905            9910            9915

Xaa Gly Val Pro Gly Xaa Gly Val Pro Gly Xaa Gly Val Pro Gly
      9920            9925            9930

Xaa Gly Val Pro Gly Xaa Gly Val Pro Gly Xaa Gly Val Pro Gly
      9935            9940            9945

Xaa Gly Val Pro Gly Xaa Gly Val Pro Gly Xaa Gly Val Pro Gly
      9950            9955            9960

Xaa Gly Val Pro Gly Xaa Gly Val Pro Gly Xaa Gly Val Pro Gly
      9965            9970            9975
```

```
Xaa Gly  Val Pro Gly Xaa Gly  Val Pro Gly Xaa Gly  Val Pro Gly
    9980                 9985                 9990

Xaa Gly  Val Pro Gly Xaa Gly
    9995                10000
```